(12) United States Patent
Kapeller-Libermann

(10) Patent No.: US 7,241,585 B2
(45) Date of Patent: Jul. 10, 2007

(54) 14171 PROTEIN KINASE, A NOVEL HUMAN PROTEIN KINASE AND USES THEREOF

(75) Inventor: Rosana Kapeller-Libermann, Chestnut Hill, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 140 days.

(21) Appl. No.: 10/658,904

(22) Filed: Sep. 10, 2003

(65) Prior Publication Data

US 2004/0048305 A1  Mar. 11, 2004

Related U.S. Application Data

(63) Continuation-in-part of application No. 09/781,882, filed on Feb. 12, 2001, now Pat. No. 6,630,335.

(60) Provisional application No. 60/182,096, filed on Feb. 11, 2000.

(51) Int. Cl.
*C12Q 1/48* (2006.01)
*C12N 1/20* (2006.01)
*C12N 15/00* (2006.01)
*C12N 9/20* (2006.01)
*C07K 1/00* (2006.01)

(52) U.S. Cl. ............... 435/15; 435/194; 435/252.3; 435/320.1; 530/350

(58) Field of Classification Search ............... 530/350; 435/194, 320.1, 252.3, 6, 15; 514/12
See application file for complete search history.

(56) References Cited

FOREIGN PATENT DOCUMENTS

| | | | |
|---|---|---|---|
| EP | 1074617 A2 | 2/2001 | |
| WO | 99/04265 | * | 1/1999 |
| WO | WO 99/55865 A1 | 11/1999 | |
| WO | WO 00/08177 A2 | 2/2000 | |
| WO | WO 00/08178 A2 | 2/2000 | |
| WO | WO 01/38503 A2 | 5/2001 | |
| WO | WO 01/57186 A2 | 8/2001 | |
| WO | WO 01/81383 A1 | 11/2001 | |

OTHER PUBLICATIONS

Thome, M. et al., Identification of CARDIAK, a RIP-like Kinase that Associates with Caspase-1, Current Biology, vol. 8(15)1988.
Holland, Pamela M. et al., "RIP4 is an Ankyrin Repeat-Containing Kinase Essential for Keratinocyte Differentiation" *Current Biology* vol. 12, (Aug. 20, 2002), pp. 1424-1428.
Bähr, Corinna et al., "DIK, A Novel Protein Kinase that Interacts with Protein Kinase Cδ" *The Journal of Biological Chemistry* vol. 275, (Nov. 17, 2000), pp. 36350-36357.
Hattori, M. et. al., "The DNA Sequence of Human Chromosome 21" *Nature* vol. 405 (May 18, 2000), pp. 311-319.
Bloecker, H. et al., "*Homo sapiens* mRNA; cDNA DKFZp434B2328 (from clone DKFZp434B2328); partial cds." Feb. 18, 2000 (sequence) GenBank [online] Bethesda, MD, USA: National Center for Biotechnology Information [retrieved on Sep. 5, 2002]. Retrieved from the Internet: <URL: http://www.ncbi.nlm.nih.gov/>. GenBank Accession No. AL137448.

* cited by examiner

*Primary Examiner*—Maryam Monshipouri
(74) *Attorney, Agent, or Firm*—Millennium Pharmaceuticals, Inc.

(57) ABSTRACT

The invention relates to a novel kinase nucleic acid sequence and protein. Also provided are vectors, host cells, and recombinant methods for making and using the novel molecules.

14 Claims, 2 Drawing Sheets

14171 PROTEIN KINASE, A NOVEL HUMAN PROTEIN KINASE AND USES THEREOF

CROSS-REFERENCE TO RELATED APPLICATION

This application is a continuation-in-part of U.S. application Ser. No. 09/781,882, filed Feb. 12, 2001, now U.S. Pat. No. 6,630,335. which claims the benefit of U.S. Provisional Application No. 60/182,096, filed Feb. 11, 2000, each of which is hereby incorporated in its entirety by reference.

FIELD OF THE INVENTION

The invention relates to a novel protein kinase nucleic acid sequence and protein. Also provided are vectors, host cells, and recombinant methods for making and using the novel molecules.

BACKGROUND OF THE INVENTION

Protein Kinases

The tight association of phosphate with a molecule, e.g., a protein, has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated molecules, e.g., proteins, implies the existence of one or more kinases, e.g., protein kinases, capable of phosphorylating various molecules, e.g., amino acid residues on proteins, and also of phosphatases, e.g., protein phosphatases, capable of hydrolyzing various phosphorylated molecules, e.g., phosphorylated amino acid residues on proteins.

Protein kinases play critical roles in the regulation of biochemical and morphological changes associated with cellular growth and division (D'Urso et al. (1990) Science 250:786-791; Birchmeier et al. (1993) Bioessays 15:185-189). They serve as growth factor receptors and signal transducers and have been implicated in cellular transformation and malignancy (Hunter et al. (1992) Cell 70:375-387; Posada et al. (1992) Mol. Biol. Cell 3:583-592; Hunter et al. (1994) Cell 79:573-582). For example, protein kinases have been shown to participate in the transmission of signals from growth-factor receptors (Sturgill et al. (1988) Nature 344:715-718; Gomez et al. (1991) Nature 353:170173), control of entry of cells into mitosis (Nurse (1990) Nature 344:503-508; Maller (1991) Curr. Opin. Cell Biol. 3:269-275) and regulation of actin bundling (Husain-Chishti et al. (1988) Nature 334:718-721). Protein kinases serve as growth factor receptors and signal transducers and have been implicated in cellular transformation and malignancy (Hunter et al. (1992) Cell 70:375-387; Posada et al. (1992) Mol. Biol. Cell 3:583-592; Hunter et al. (1994) Cell 79:573-582). Alterations in kinase genes and their products can lead to deregulated cell proliferation, a hallmark of cancer. Modulation of these genes and their regulatory activities may permit the control of tumor cell proliferation and invasion.

Protein kinases can be divided into different groups based on either amino acid sequence similarity or specificity for either serine/threonine or tyrosine residues. A small number of dual-specificity kinases have also been described. Within the broad classification, kinases can be further subdivided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks et al. (1988) Science 241:42-52).

Extracellular-signal-regulated kinases/microtubule-associated protein kinases (Erk\MAPKs) and cyclin-directed kinases (Cdks) represent two large families of serinethreonine kinases (see Songyang et al., (1996) Mol. Cell. Biol. 16:6486-6493). Both types of kinases function in cell growth, cell division, and cell differentiation, in response to extracellular stimulae. The Erk\MAPK family members are critical participants in intracellular signaling pathways. Upstream activators as well as the Erk\MAPK components are phosphorylated following contact of cells with growth factors or hormones or after cellular stressors, for example, heat, ultraviolet light, and inflammatory cytokines. Cdks regulate transitions between successive stages of the cell cycle. The activity of these molecules is controlled by phosphorylation events and by association with cyclin. Cdk activity is negatively regulated by the association of small inhibitory molecules (Dynlacht, (1997) Nature 389:148-152).

Members of the tumor necrosis factor receptor superfamily have an important role in the induction of cellular signals resulting in cell growth, differentiation, and death. See Smith et al. (1994) Cell 76:959-962. Tumor necrosis factor receptor-1 recruits and assembles a signaling complex containing a number of death domain-containing proteins and a serine/threonine kinase, RIP, which mediates tumor necrosis factor-induced activation of nuclear factor-κB. See Stanger et al. (1995) Cell 81:513-523 and Kelliher et al. (1998) Immunity 8:297-303. Recently, another RIP-like kinase has been characterized, designated "CARDIAK," which contains a serine/threonine kinase domain as well as a carboxy-terminal caspase recruiting domain (CARD) (Thome, et al. (1998) Current Biology 8:885888). Overexpression of this serine/threonine kinase induced the activation of both nuclear factor-κB and Jun N-terminal kinase. This kinase also interacted with the tumor necrosis factor receptor-associated factors TRAF-1 and TRAF-2. A dominant negative form of TRAF-2 inhibited CARDIAK-induced nuclear factor-κb activation. The data in the report suggested that CARDIAK is involved in nuclear factor-κB/Jun N-terminal kinase signaling.

Protein kinases play critical roles in cellular growth. Therefore, novel protein kinase polynucleotides and proteins are useful for modulating cellular growth, differentiation and/or development.

Programmed Cell Death

In multicellular organisms, homeostasis is maintained by balancing the rate of cell proliferation against the rate of cell death. Cell proliferation is influenced by numerous growth factors and the expression of proto-oncogenes, which typically encourage progression through the cell cycle. In contrast, numerous events, including the expression of tumor suppressor genes, can lead to an arrest of cellular proliferation.

In differentiated cells, a particular type of cell death called apoptosis occurs when an internal suicide program is activated. This program can be initiated by a variety of external signals as well as signals that are generated within the cell in response to, for example, genetic damage. Dying cells are eliminated by phagocytes, without an inflammatory response.

Programmed cell death is a highly regulated process (Wilson (1998) *Biochem. Cell. Biol.* 76:573-582). The death signal is then transduced through various signaling pathways that converge on caspase-mediated degradative cascades resulting in the activation of late effectors of morphological and physiological aspects of apoptosis, including DNA fragmentation and cytoplasmic condensation. In addition, regulation of programmed cell death may be integrated with regulation of energy, redox- and ion homeostasis in the mitochondria (reviewed by (Kroemer, 1998)), and/or cell-cycle control in the nucleus and cytoplasm (reviewed by (Choisy-Rossi and Yonish-Rouach, 1998; Dang, 1999; Kasten and Giordano, 1998)). Many mammalian genes regulating apoptosis have been identified as homologs of genes originally identified genetically in *Caenorhabditis elegans* or *Drosophila melanogaster*, or as human oncogenes. Other programmed cell death genes have been found by domain homology to known motifs, such as death domains, that mediate protein-protein interactions within the programmed cell death pathway.

The mechanisms that mediate apoptosis include, but are not limited to, the activation of endogenous proteases, loss of mitochondrial function, and structural changes, such as disruption of the cytoskeleton, cell shrinkage, membrane blebbing, and nuclear condensation due to degradation of DNA. The various signals that trigger apoptosis may bring about these events by converging on a common cell death pathway that is regulated by the expression of genes that are highly conserved. Caspases (cysteine proteases having specificity for aspartate at the substrate cleavage site) are central to the apoptotic program. These proteases are responsible for degradation of cellular proteins that lead to the morphological changes seen in cells undergoing apoptosis.

Thus, programmed cell death (apoptosis) is a normal physiological activity necessary to proper and differentiation in all vertebrates. Defects in apoptosis programs result in disorders including, but not limited to, neurodegenerative disorders, cancer, immunodeficiency, heart disease and autoimmune diseases (Thompson et al. (1995) *Science* 267: 1456).

Accordingly, genes involved in apoptosis are important targets for therapeutic intervention. It is important, therefore, to identify novel genes involved in apoptosis or to discover whether known genes function in this process.

SUMMARY OF THE INVENTION

The present invention is based, in part, on the discovery of a novel protein kinase family member, referred to herein as "14171," "protein kinase" or "14171 protein kinase." An isolated nucleic acid molecule corresponding to a 14171 protein kinase nucleic acid sequence is provided. Additionally an amino acid sequence corresponding to the polynucleotide is encompassed. In particular, the present invention provides for an isolated nucleic acid molecule (SEQ ID NO:1) comprising the nucleotide sequence encoding the amino acid sequence shown in SEQ ID NO:2. Further provided is a 14171 protein kinase polypeptide having an amino acid sequence encoded by the nucleic acid molecule described herein. The coding sequence for human 14171 is shown in SEQ ID NO:3.

Accordingly, in one aspect, the invention features a nucleic acid molecule which encodes a 14171 protein or polypeptide, e.g., a biologically active portion of the 14171 protein. In a preferred embodiment, the isolated nucleic acid molecule encodes a polypeptide having the amino acid sequence of SEQ ID NO:2. In other embodiments, the invention provides isolated 14171 nucleic acid molecules having the nucleotide sequence shown in SEQ ID NO:1 or SEQ ID NO:3. In still other embodiments, the invention provides nucleic acid molecules that are substantially identical (e.g., naturally occurring allelic variants) to the nucleotide sequence shown in SEQ ID NO:1 or SEQ ID NO:3. In other embodiments, the invention provides a nucleic acid molecule which hybridizes under a stringent hybridization condition as described herein to a nucleic acid molecule comprising the nucleotide sequence of SEQ ID NO:1 or SEQ ID NO:3, wherein the nucleic acid encodes a full length 14171 protein or an active fragment thereof.

In a related aspect, the invention further provides nucleic acid constructs which include a 14171 nucleic acid molecule described herein. In certain embodiments, the nucleic acid molecules of the invention are operatively linked to native or heterologous regulatory sequences. The present invention also provides vectors and host cells for recombinant expression of the 14171 nucleic acid molecule described herein, as well as methods of making such vectors and host cells and for using them for production of the polypeptide or peptides of the invention by recombinant techniques.

The 14171 protein kinase molecule of the present invention is useful for modulating cellular growth and/or cellular metabolic pathways particularly for regulating one or more proteins involved in growth and metabolism. Accordingly, in one aspect, this invention provides an isolated nucleic acid molecule encoding a 14171 protein kinase protein or biologically active portions thereof, as well as nucleic acid fragments suitable as primers or hybridization probes for the detection of protein kinase-encoding nucleic acids. In still another related aspect, isolated nucleic acid molecules that are antisense to a 14171 encoding nucleic acid molecule are provided.

Another aspect of this invention features an isolated or recombinant 14171 kinase protein and polypeptide, and biologically active or antigenic fragments thereof that are useful, e.g., as reagents or targets in assays applicable to treatment and diagnosis of kinase-associated or other 14171-associated disorders. In another embodiment, the invention provides 14171 polypeptides having a 14171 activity. Preferred protein kinase proteins and polypeptides include at least one kinase domain, and, preferably, possess at least one biological activity, e.g., a kinase activity (e.g., phosphorylation of a threonine followed by a proline in a polypeptide, e.g., a 42-45 kDa polypeptide), possessed by naturally-occurring 14171 protein kinase.

In other embodiments, the invention provides 14171 polypeptides, e.g., a 14171 polypeptide having the amino acid sequence shown in SEQ ID NO:2; an amino acid sequence that is substantially identical to the amino acid sequence shown in SEQ ID NO:2; or an amino acid sequence encoded by a nucleic acid molecule having a nucleotide sequence which hybridizes under a stringent hybridization condition as described herein to a nucleic acid molecule comprising the nucleotide sequence of SEQ ID NO:1 or SEQ ID NO:3, wherein the nucleic acid encodes a full length 14171 protein or an active fragment thereof.

Variant nucleic acid molecules and polypeptides substantially homologous to the 14171 nucleotide and amino acid sequence set forth in the sequence listing are encompassed by the present invention. Additionally, fragments and substantially homologous fragments of the 14171 nucleotide and amino acid sequence are provided.

In a related aspect, the invention provides 14171 polypeptides or fragments operatively linked to non-14171 polypeptides to form fusion proteins.

Antibodies and antibody fragments that selectively bind the 14171 protein kinase polypeptide and fragments are provided. Such antibodies are useful in detecting the 14171 protein kinase polypeptide as well as in modulating its activity, e.g., cellular growth or apoptosis, e.g., in epithelial cells or in tumor cells; or in the treatment of, e.g., inflammatory disorders or cancer.

In another aspect, the present invention provides a method for detecting the presence of 14171 protein kinase activity or expression in a biological sample by contacting the biological sample with an agent capable of detecting an indicator of 14171 protein kinase activity such that the presence of 14171 protein kinase activity is detected in the biological sample.

In yet another aspect, the invention provides a method for modulating 14171 protein kinase nucleic acid expression or kinase activity comprising contacting a cell, e.g., an epithelial cell, with an agent that modulates (inhibits or stimulates) protein kinase activity or expression such that 14171 protein kinase activity or expression in the cell is modulated. In one embodiment, the agent is an antibody that specifically binds to kinase protein. In another embodiment, the agent modulates expression of 14171 protein kinase protein by modulating transcription of a protein kinase gene, splicing of a protein kinase mRNA, or translation of a protein kinase mRNA. In another embodiment, the agent is a nucleic acid molecule having a nucleotide sequence that is antisense to the coding strand of the 14171 protein kinase mRNA or the 14171 protein kinase gene. In another embodiment, the agent is an siRNA specific for the 14171 protein kinase mRNA. In yet another embodiment, the agent is a compound identified in screening assays described herein.

In one embodiment, the methods of the present invention are used to treat a subject having a disorder, e.g., a cell growth or differentiation disorder (e.g., a cancer), an apoptotic disorder, a viral disorder, an inflammatory disorder, a kidney disorder, or a prostate disorder characterized by aberrant 14171 protein kinase protein activity or aberrant 14171 nucleic acid expression by administering an agent that is a 14171 protein kinase modulator to the subject. In one embodiment, the 14171 protein kinase modulator is a 14171 protein kinase protein. In another embodiment, the 14171 protein kinase modulator is a 14171 protein kinase nucleic acid molecule. In other embodiments, the 14171 protein kinase modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding a 14171 protein kinase protein; (2) misregulation of a gene encoding a 14171 protein kinase protein; and (3) aberrant post-translational modification of a 14171 protein kinase protein, wherein a wildtype form of the gene encodes a protein with a 14171 protein kinase activity.

In another aspect, the invention provides a method for identifying a compound that binds to or modulates the activity of a 14171 protein kinase protein. In general, such methods entail measuring a biological activity of a 14171 protein kinase protein in the presence and absence of a test compound and identifying those compounds that alter the activity of the 14171 protein kinase protein.

The invention also features methods for identifying a compound that modulates the expression of the 14171 protein kinase gene by measuring the expression of the 14171 protein kinase sequence in the presence and absence of the compound.

The invention also provides compounds identified by the screening methods described herein.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 14171 molecule. In one embodiment, the capture probe is a nucleic acid, e.g., a probe complementary to a 14171 nucleic acid sequence. In another embodiment, the capture probe is a polypeptide, e.g., an antibody specific for 14171 polypeptides. Also featured is a method of analyzing a sample by contacting the sample to the aforementioned array and detecting binding of the sample to the array.

Other features and advantages of the invention will be apparent from the following detailed description and claims.

DETAILED DESCRIPTION OF THE INVENTION

Figure 1:
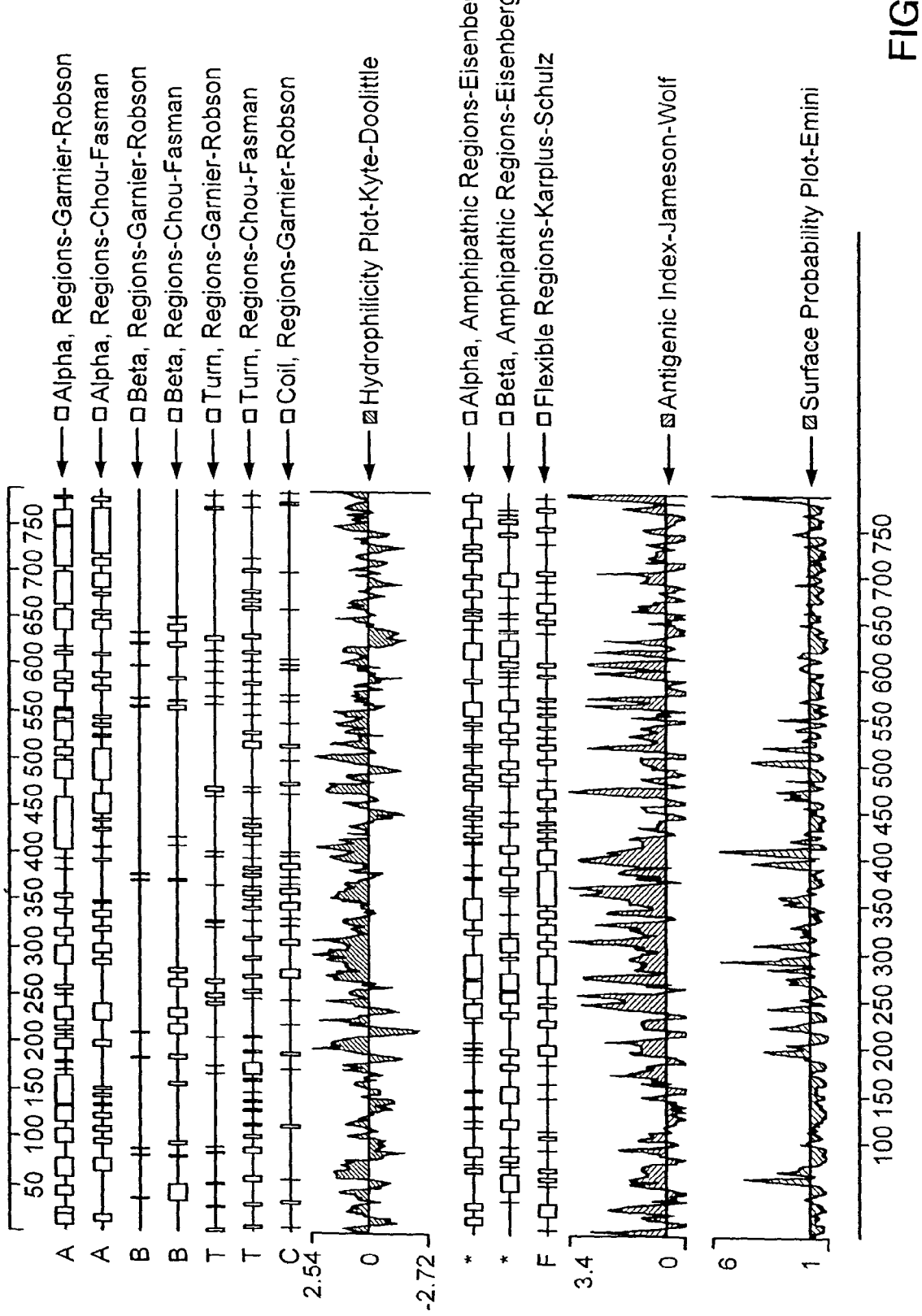
FIG. 1 shows an analysis of the 14171 amino acid sequence: αβ turn and coil regions; hydrophilicity; amphipathic regions; flexible regions; antigenic index; and surface probability.

The present invention is based, at least in part, on the identification of a novel molecule, 14171, which is a protein kinase. When referring to the 14171 protein kinase, the term "kinase" is intended to mean a protein having protein kinase activity or to a nucleic acid encoding the protein, or a fragment thereof. The kinase nucleic acid and polypeptide molecules of the invention play a role in, or function in, signaling pathways associated with cellular growth and/or cellular metabolic pathways, e.g., in epithelial cells or in tumor cells, and, in the present case, is also involved in a productive viral infection, in inflammatory disorders and cancer. These growth and metabolic pathways are described in Lodish et al. (1995) *Molecular Cell Biology* (Scientific American Books Inc., New York, N.Y.) and Stryer Biochemistry, (W. H. Freeman, New York), the contents of which are incorporated herein by reference. In particular, the 14171 protein kinase is involved in the nuclear factor-kappaB (NF-κB) signaling pathway and 14171 expression can be regulated by the p53 tumor suppressor. In one embodiment, the kinase molecule modulates the activity of one or more proteins involved in viral infection, cellular growth, or differentiation, e.g., in hepatitis B virus (HBV)-infected cells. In another embodiment, the kinase molecule of the present invention is capable of modulating the phosphorylation state of a kinase molecule or the phosphorylation state of one or more proteins involved in apoptosis, viral infection, inflammation, cellular growth, or differentiation, e.g., HBV-infected cells, epithelial cells or cells in the kidney. The 14171 protein kinase can activate NF-κB. The ability or availability of 14171 for kinase activity can be regulated, e.g., downregulated, by p53. See also Lodish et al. and Stryer, supra. In addition, kinases of the present invention are targets of drugs described in Goodman and Gilman (1996), *The Pharmacological Basis of Therapeutics* (9$^{th}$ ed.) Hartman & Limbard Editors, the contents of which are incorporated herein by reference. Particularly, the kinase of the invention modulates phosphorylation in HBV virus-infected tissues and cells, such as liver, in tissues and cells affected by inflammatory disorders, such as the lung, in tissues and cells affected by cancer, such as lung, colon, prostate, ovary and breast, and in tissues and cells of the kidney and in epithelial cells, e.g., of the prostate and lung.

The kinase of the invention contains domains or motifs, identified by routine homology searching procedures, for example Pfam and Prosite analysis. Such analysis has identified six or ten ankyrin motifs and homology to various ankyrin proteins from humans and other species and to ankyrin-like proteins. Birkenmeier et al. ((1998) *Genomics* 50:79-88) has shown an erythroid ankyrin gene producing an isoform containing an amino terminal membrane anchor. Kordeli et al. ((1998) *J. Cell Sci.* 111:2197-2207) has shown that ankyrin G is associated with the post-synaptic membrane and sarcoplasmic reticulum in skeletal muscle fiber. Zhang et al. ((1998) *J. Biol. Chem.* 273:18681-18684) has shown the structure of the ankyrin binding domain of α-sodium potassium ATPase. Miraglia et al. ((1998) *J. Pediat.* 132:117-120) has shown a high frequency of spontaneous mutations in the ankyrin gene in children with heredity spherocytosis. Randon et al. ((1997) *Br. J. Haematol.* 96:500-506) has shown frequent spontaneous mutations of the ankyrin gene mimicking a recessive mode of transmission in heredity spherocytosis and described three new ankyrin variants. Accordingly, the 14171 protein kinase of the invention, containing an ankyrin motif, contains, in addition to kinase activity, functions of the ankyrin protein including, but not limited to, those discussed in the references above, incorporated herein by reference for these functions and for assays for detecting such functions. The ankyrin repeat domains can mediate interactions of 14171 with other proteins and/or can confer a membrane association on the polypeptides of the invention.

The 14171 protein kinase of the invention also contains a kinase motif for serine/threonine kinase activity. The serine/threonine kinase, RIP, (Stanger et al. (1995) *Cell* 81:513-523) mediates tumor necrosis factor-induced nuclear factor-κB activation, as discussed above. In fact, the protein kinase of the invention, having a kinase domain at the 5' end and the ten ankyrin repeats at the 3' end shows similarity of the kinase to RIP. Recently the serine/threonine kinase CARDIAK has been shown to induce activation of both nuclear factor-κB and Jun N-terminal kinase. The gene was shown to induce apoptosis in 293T cells. It was shown to function via the nuclear factor κB signal pathway by means of a luciferase reporter with nuclear factor-κB binding sites in 293T cells. The gene was also shown to interact through binding to TRAF-1 and TRAF-2. Accordingly, the serine/threonine kinase of the invention, shown by BLAST homology searching to contain homology to a human RIP-like kinase, has been found to activate NF-κB, is likely to function in this signal pathway, including the phosphorylation and activation of these substrates as well as interactions with other molecules of the pathway, such as the TRAF family. In addition, the expression of 14171 can be regulated by p53. Further, like CARDIAK, the kinase of the invention is capable of autophosphorylation activity. A recent publication, (Bahr et al. (2000) *J. Biol. Chem.* 275:36350-36357) describes protein kinase C delta interacting kinase (DIK), a splice variant of 14171.

The gene encoding the protein kinase of the invention maps to human chromosome 21 with a syntenic chromosome, possibly mo10, 17, or 16. Flanking markers include WI-5330 (7.1cR) WI-3679 (4.7 cR). Nearby mutations/loci include DFNB8, deafness, neurosensory, autosomal recessive 8; DSCR Down's Syndrome critical region, included; KNO, knobloch syndrome. Nearby known genes include PAPPA, FRG1, WHITE1, TFF3, MX1, TFF2, PDE9A, CBS, PDXK, C21ORF2, ES1, PFKL, TRPC7, ADARB1, ITGB2, COL18A1, SLC19A1, LSS, HRTM1L1.

As used herein, a protein kinase includes a protein or polypeptide that is capable of modulating its own phosphorylation state or the phosphorylation state of a different protein or polypeptide. Such a change comprises alteration of any of the various bonds, oxidation, reduction of the molecule, to effect the addition of phosphate. Protein kinases can have a specificity for (i.e., a specificity to phosphorylate) serine/threonine residues, tyrosine residues, or both serine/threonine and tyrosine residues, e.g., the dual-specificity protein kinases. As referred to herein, protein kinases, preferably include a catalytic domain of about 200-400 amino acid residues in length, preferably about 200-300 amino acid residues in length, or more preferably about 250-300 amino acid residues in length, which includes preferably 5-20, more preferably 5-15, or most preferably 11 highly conserved motifs or subdomains separated by sequences of amino acids with reduced or minimal conservation. Specificity of a protein kinase for phosphorylation of either tyrosine or serine/threonine can be predicted by the sequence of two of the subdomains (VIb and VIII) in which different residues are conserved in each class (as described in, for example, Hanks et al. (1988) *Science* 241:42-52, the contents of which are incorporated herein by reference). These subdomains are also described in further detail herein.

In one embodiment, a 14171 protein kinase has specificity for phosphorylation of a threonine residue. In a preferred embodiment, a 14171 protein kinase has specificity for phosphorylation of a threonine residue which is followed by a proline residue in the amino acid sequence (i.e., phosphorylation of a threonine a T-P motif). In this embodiment, a 14171 protein kinase acts as an intracellular signal transduction kinase, e.g., as a mitogen-activated protein kinase/cyclin-dependent kinase (MAPK/CDK). In one embodiment, a substrate for a 14171 protein kinase is a polypeptide with a T-P motif. In another embodiment, a substrate for a 14171 protein kinase is myelin basic protein, or a peptide fragment thereof or myristoylated alanine-rich C kin ase substrate, or a peptide fragment thereof, e.g., peptide 3 (e.g., SEQ ID NO:20). In a preferred embodiment, a substrate for a 14171 protein kinase is a cell-associated (e.g., an intracellular cytosolic, nuclear or membrane-bound polypeptide) with a T-P motif and a molecular weight, as estimated by SDS-PAGE of about 42-45 kDa (e.g., having between about 300, 310, 320, 330, 340, preferably about 350 amino acid residues and about 400, 410, 420, 430 440 or 450, preferably about 409 amino acid residues).

Protein kinases play a role in signaling pathways associated with cellular growth. For example, protein kinases are involved in the regulation of signal transmission from cellular receptors, e.g., growth-factor receptors, entry of cells into mitosis, and the regulation of cytoskeleton function, e.g., actin bundling.

Assays for measuring protein kinase activity are well known in the art depending on the particular protein kinase. Specific assay protocols are available in standard sources known to the ordinarily skilled artisan. For example, see "Kinases" in Ausubel et al., eds. (1994-1998) *Current Protocols in Molecular Biology* (3) and references cited therein.

Further, apoptosis-specific assays may be used to identify modulators of any of the target nucleic acids or proteins of the present invention, which proteins and/or nucleic acids are related to apoptosis. Accordingly, an agent that modulates the level or activity of any of these nucleic acids or proteins can be identified by means of apoptosis-specific assays. For example, high throughput screens exist to identify apoptotic cells by the use of chromatin or cytoplasmic-specific dyes. Thus, hallmarks of apoptosis, cytoplasmic condensation and chromosome fragmentation, can be used as a marker to identify modulators of any of the gene related to programmed-cell death described herein. Other assays include, but are not limited to, the activation of specific endogenous proteases, loss of mitochondrial function, cytoskeletal disruption, cell shrinkage, membrane blebbing, and nuclear condensation due to degradation of DNA.

Apoptosis can be actively induced in animal cells by a diverse array of triggers that range from ionizing radiation to hypothermia to viral infections to immune reactions. Majno et al. (1995) *Amer. J. Pathol.* 146:3-15; Hockenberry et al. (1995) *Bio Essays* 17:631-638; Thompson et al. (1995) *Science* 267:1456-1462.

Apoptosis can be triggered by the addition of apoptosis-promoting ligands to a cell in culture or in vivo. Apoptosis can also be triggered by decreasing or removing an apoptosis-inhibiting or survival-promoting ligand. Accordingly, apoptosis is triggered in view of the fact that the cell lacks a signal from a cell surface survival factor receptor. Ligands include, but are not limited to, FasL. Death-inhibiting ligands include, but are not limited to, IL-2. See Hetts et al. (1998) *JAMA* 279:300-307 (incorporated by reference in its entirety for teaching of ligands involved in active and passive apoptosis pathways). Central in the pathway, and also serving as potential molecules for inducing (or releasing from inhibition) apoptosis pathways include FADD, caspases, human CED4 homolog (also called apoptotic protease activating factor 1), the Bcl-2 family of genes including, but not limited to, apoptosis promoting (for example, Bax and Bad) and apoptosis inhibiting (for example, Bcl-2 and Bcl-$x_1$) molecules. See Hetts et al., above.

Multiple caspases upstream of caspase-3 can be inhibited by viral proteins such as cowpox, CrmiA, and baculovirus, p35. Synthetic tripeptides and tetrapeptides inhibit caspase-3 specifically (Hetts, above).

Accordingly, cellular and animal models also exist for studying expression or function of the kinase protein sequences in apoptosis and with regard to their effect on apoptosis. Such model systems can be applied in the context of the assays described herein below, for example the effect of specific mutations in the kinase protein, the effect of compounds on the kinase protein, and any of the other assays in which the effect of altered expression or activity of the kinase protein is within the context of effects on apoptosis.

The 14171 molecules of the invention can play a role in cells or tissues where its expression or activity is regulated relative to normal cells or tissues. Accordingly, the 14171 molecules of the invention can play a role in the disorders or diseases of these cells or tissues. For example, 14171 mRNA levels showed regulation in bronchial epithelial cells, under conditions which simulate asthma or allergic rhinitis. Furthermore, 14171 mRNA levels were elevated relative to normal levels in tissues displaying the disorders of asthma, bronchitis, cystic fibrosis, idiopathic pulmonary fibrosis and chronic obstructive pulmonary disease. Thus, regulation of the expression or activity of the 14171 molecules of the invention can be used to treat and/or diagnose lung diseases, e.g., inflammatory lung disorders (e.g., asthma, allergic rhinitis, bronchitis, cystic fibrosis, idiopathic pulmonary fibrosis and chronic obstructive pulmonary disease). Another example of regulated expression of 14171 mRNA was found in tumor tissues, which showed higher 14171 expression than the corresponding normal tissue from the same organ. These tissues included tumors from lung, colon, prostate, breast, ovary, including clear cell ovarian tumor tissues and primary serous ovarian cancer tissues. When the tumor suppressor gene, p53 is induced in tumor cells, the tumor cells reduce the expression of 14171 mRNA. Thus, regulation of the expression or activity of the 14171 molecules of the invention can be used to treat and/or diagnose tumors or cancerous conditions, e.g., cellular growth related-disorders (e.g., cancer of the lung, colon, prostate, breast, and ovary). Additionally, the 14171 molecules of the invention can be involved in diseases resulting from aberrant expression or activity of p53. A further example of the regulated expression of 14171 mRNA was found in virus-infected cells. 14171 RNA was found to be more abundant in HBV-infected HepG2 cells than in uninfected HepG2 cells. Thus, regulation of the expression or activity of the 14171 molecules of the invention can be used to treat and/or diagnose viral infection, such as DNA virus infection, including but not limited to HBV infection.

The 14171 molecules of the invention can modulate the activities of cells in tissues where they are expressed. For example, 14171 mRNA has high levels of expression in the kidney and in prostate epithelial cells. Accordingly, the 14171 molecules of the invention can act as therapeutic or diagnostic agents for renal diseases and prostate diseases.

The 14171 molecules of the invention can participate in signaling through NF-κB. Extracellular signals which induce the activation of NF-κB include cytokines, reactive oxygen species, bacterial infection and others. Active NF-κB can induce the transcription of many genes, including cytokines, chemokines, receptors, enzymes (reviewed in Chen et al. (2001) *Am. J. Pathol.* 159:387-397 and in Yamamoto and Gaynor (2001) *J. Clin. Invest* 107:135-142). After the expression of genes induced by NF-κB, cell cycle progression can be regulated, cells can undergo apoptosis or cells can be protected from apoptosis, depending on cell type and the activity of other molecules. Regulation of NF-κB is involved in many diseases, including inflammatory diseases, such as asthma, rheumatoid arthritis, and inflammatory bowel disease, such as Crohn's disease and ulcerative colitis; lung diseases, such as acute respiratory distress syndrome, sepsis, asthma, viral infections or responses to pollutants (reviewed in Christman et al. (2000) *Chest* 117:1482-1487); atherosclerosis, hypertensive diseases, including chronic renal disease and heart diseases, neurodegenerative diseases, such as Alzheimer's disease; cancers; and diabetes. Expression of 14171 molecules of the invention in cells induced the activation of NF-κB. Thus, regulation of the expression or activity of the 14171 molecules of the invention can be used to treat and/or diagnose conditions, described above, caused by aberrant regulation of NF-κB activity or expression.

Further details of diseases and disorders involving tissues, organs and conditions where the 14171 protein kinase molecules of the invention are expressed, have regulated expression, or can regulate the expression or activity of another molecule are described below.

Inhibition or over-stimulation of the activity of kinases involved in signaling pathways associated with cellular growth can lead to perturbed cellular growth, which can in turn lead to cellular growth related-disorders. As used herein, a "cellular growth-related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy. Examples of cellular growth related disorders include cardiovascular disorders such as heart failure, hypertension, atrial fibrillation, dilated cardiomyopathy, idiopathic cardiomyopathy, or angina; proliferative disorders or differentiative disorders such as cancer, e.g., liver cancer, melanoma, prostate cancer, cervical cancer, breast cancer, colon cancer, or sarcoma.

The disclosed invention accordingly relates to methods and compositions for the modulation, diagnosis, and treatment of disorders associated with, caused by, or related to viral infection. These disorders can manifest as immune, inflammatory, respiratory, hematological, cardiovascular, and other disorders including, but not limited to, AIDS, virus associated leukemias, lymphomas, sarcomas, and carcinomas, herpetic infections and collateral symptoms, EBV infection, including mononucleosis, hepatitis virus infection, including A, B, C, and D viruses, with virally induced liver cancer and viral pneumonias.

Viruses include, but are not limited to, those identified with carcinogenesis, including hepatitis B virus (HBV) and liver cancer, Epstein-Barr virus (EBV), and lymphoma, human T-cell lymphotrophic virus Type I (HTLV-1) and leukemia, and human Herpes virus 8 (HHV-8) and Kaposi sarcoma. Virus families to which the invention pertains include but are not limited to Adenoviridae, Picornaviridae, Coronaviridae, Orthomyxoviridae, Paramyxoviridae, Reoviridae, Caliciviridae, Hepadnaviridae, Viroidlike, Flaviviridae, Norwalk-like, Togaviridae, Parvoviridae, Poxyiridae, Herpesviridae, Retroviridae, Reoviridae (Orbivirus), Arenaviridae, Bunyaviridae, Filoviridae, Hantavirus, and Papovaviridae. Respiratory diseases have been associated with Adenovirus, Echovirus, Rhinovirus, Coxsackievirus, Coronavirus, Influenza viruses A, B, Parainfluenza virus 1-4, and Respiratory syncytial virus. Viral diseases of the respiratory system include, but are not limited to, lower respiratory tract infections, conjunctivitis, diarrhea; upper respiratory tract infections, pharyngitis, rash; pleurodynia, herpangina, hand-foot-and-mouth disease; influenza, croup, bronchiolitis, and pneumonia. Digestive diseases have been associated with Mumps virus, Rotavirus, Norwalk agent, Hepatitis A Virus, Hepatitis B Virus, Hepatitis D Virus, Hepatitis C Virus, and Hepatitis E Virus. These include but are not limited to mumps, pancreatitis, orchitis; childhood diarrhea; gastroenteritis; acute viral hepatitis; acute or chronic hepatitis; with HBV, acute or chronic hepatitis; and enterically transmitted hepatitis. Systemic viral pathogens associated with skin eruptions include, but are not limited to, Measles virus, Rubella virus, Parvovirus, Vaccinia virus, Varicella-zoster virus, Herpes simplex virus 1, and Herpes simplex virus 2. Disease expression includes, but is not limited to, Measles (rubeola); German measles (rubella); Erythema infectiosum, aplastic anemia; smallpox; chickenpox, shingles; "cold sore"; and genital herpes. Systemic viral pathogens associated with hematopoietic disorders include Cytomegalovirus, EpsteinBarr virus, HTLV-I, HTLV-II, HIV-1 and HIV-2. Disease expression includes, but is not limited to, Cytomegalic inclusion disease; infectious mononucleosis; adult T-cell leukemia; tropical spastic paraparesis; and AIDS. Viral pathogens associated with Arboviral and Hemorrhagic fevers include, but are not limited, Dengue virus 1-4, yellow fever virus, Colorado tick fever virus, and regional hemorrhagic fever viruses. Disease expression includes, but is not limited to, Dengue, hemorrhagic fever; yellow fever; Colorado tick fever; Bolivian, Argentinian, Lassa fever; Crimean-Congo, Hantaan, sandfly fever; Ebola, Marburg disease; Korean, U.S. pneumonia. Viral pathogens associated with warty growths include Papillomavirus and molluscum virus. Disease expression includes, but is not limited to, condyloma; cervical carcinoma; and molluscum contagiosum. Viral pathogens associated with diseases of the central nervous system include, but are not limited to, Poliovirus, Rabiesvirus, JC virus, and Arboviral encephalitis viruses. Disease expression includes, but is not limited to, Poliomyelitis; Rabies; progressive multifocal leukoencephalopathy (opportunistic); Eastern, Western, Venezuelan, St. Louis, Calif. group.

Other especially relevant disorders include those that are associated with programmed cell death. These include, but are not limited to, those described herein and also in the references above, that are incorporated herein by reference for disclosure of disorders associated with programmed cell death.

As used herein, "programmed cell death" refers to a genetically regulated process involved in the normal development of multicellular organisms. This process occurs in cells destined for removal in a variety of normal situations, including larval development of the nematode C. elegans, insect metamorphosis, development in mammalian embryos, including the nephrogenic zone in the developing kidney, and regression or atrophy (e.g., in the prostate after castration). Programmed cell death can occur following the withdrawal of growth and trophic factors in many cells, nutritional deprivation, hormone treatment, ultraviolet irradiation, and exposure to toxic and infectious agents including reactive oxygen species and phosphatase inhibitors, e.g., okadaic acid, calcium ionophores, and a number of cancer chemotherapeutic agents. See Wilson (1998) *Biochem. Cell Biol.* 76:573-582 and Hetts (1998) *JAMA* 279:300-307, the contents of which are incorporated herein by reference. Thus, the protein of the invention can modulate a programmed cell death pathway activity and provide a novel diagnostic target and therapeutic agents for disorders characterized by deregulated programmed cell death, particularly in cells that express the protein.

In vertebrate species, neuronal programmed cell death mechanisms have been associated with a variety of developmental roles, including the removal of neuronal precursors which fail to establish appropriate synaptic connections (Oppenheim et al. (i991) *Annual Rev. Neuroscience* 14:453-501), the quantitative matching of pre- and post-synaptic population sizes (Herrup et al. (1987) *J. Neurosci.* 7:829-836), and sculpting of neuronal circuits, both during development and in the adult (Bottjer et al. (1992) *J. Neurobiol.* 23:1172-1191).

As used herein, a "disorder characterized by deregulated programmed cell death" refers to a disorder, disease or condition which is characterized by a deregulation, e.g., an upregulation or a downregulation, of programmed cell death. Programmed cell death deregulation can lead to deregulation of cellular proliferation and/or cell cycle progression. Examples of disorders characterized by deregulated programmed cell death include, but are not limited to, neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, Jakob-Creutzfieldt disease, or AIDS related dementias; myelodysplastic syndromes, e.g., aplastic anemia; ischemic injury, e.g., myocardial infarction, stroke, or reperfusion injury; autoimmune disorders, e.g., systemic lupus erythematosus, or immune-mediated glomerulonephritis; or profilerative disorders, e.g., cancer, such as follicular lymphomas, carcinomas with p53 mutations, or hormonedependent tumors, e.g., breast cancer, prostate cancer, or ovarian cancer). Clinical manifestations of faulty apoptosis are also seen in stroke and in rheumatoid arthritis (Wilson (1998) *Biochem. Cell. Biol.* 76:573-582).

Many disorders can be classified based on whether they are associated with abnormally high or abnormally low apoptosis. Thompson (1995) *Science* 267:1456-1462. Apoptosis may be involved in acute trauma, myocardial infarction, stroke, and infectious diseases, such as viral hepatitis and acquired immunodeficiency syndrome.

Failure to remove autoimmune cells that arise during development or that develop as a result of somatic mutation during an immune response can result in autoimmune disease. One of the molecules that plays a critical role in regulating cell death in lymphocytes is the cell surface receptor for Fas. Apoptosis deficiencies of lymphoproliferation and autoimmunity include, but are not limited to, Canale-Smith syndrome.

Viral infections, such as those caused by herpesviruses, poxviruses, and adenoviruses, may result in aberrant apoptosis. Populations of cells are often depleted in the event of viral infection, with perhaps the most dramatic example being the cell depletion caused by the human immunodeficiency virus (HIV). Most T cells that die during HIV infections do not appear to be infected with HIV. Stimulation of the CD4 receptor may result in the enhanced susceptibility of uninfected T cells to undergo apoptosis.

Primary apoptosis deficiencies include graft rejection. Accordingly, the invention is relevant to the identification of genes useful in inhibiting graft rejection. Primary apoptosis deficiencies also include autoimmune diabetes. Accordingly, the invention is relevant to genes involved in autoimmune diabetes and accordingly, to the identification of agents that act on these targets to modulate the expression of these genes and hence, to treat or diagnose this disorder. Further, it has been suggested that all autoimmune disorders can be viewed as primary deficiencies of apoptosis (Hetts, above). Accordingly, the invention is relevant for screening for gene expression and transcriptional profiling in any autoimmune disorder and for screening for agents that affect the expression or transcriptional profile of the kinase genes.

Primary apoptosis deficiencies also include cancer. For example, p53 induces apoptosis by acting as a transcription factor that activates expression of various apoptosis-mediating genes or by upregulating apoptosis-mediating genes such as Bax. Another example is that several "oncogenes" are in fact involved in apoptosis, such as in the Bcl family.

Additional apoptotic disorders involving p53 include, but are not limited to, lymphoproliferative disorders, aspects of neurodegenerative disorders, such as Huntington's disease, Alzheimer's disease, Parkinson's disease, and ischemic brain disease resulting from trauma or stroke Primary apoptosis excesses are associated with neurodegenerative disorders including Alzheimer's disease, Parkinson's disease, spinal muscular atrophy, and amyotrophic lateral sclerosis. A wide variety of neurological diseases are characterized by the gradual loss of specific sets of neurons. Such disorders include Alzheimer's disease, Parkinson's disease, amyotrophic lateral sclerosis (ALS), retinitis pigmentosa, spinal muscular atrophy, and various forms of cerebellar degeneration. The cell loss in these diseases does not induce an inflammatory response, and apoptosis appears to be the mechanism of cell death. Primary apoptosis deficiencies also include local self reactive disorders, such as Hashimoto thyroiditis.

Primary apoptosis excesses are also associated with heart disease including idiopathic dilated cardiomyopathy, ischemic cardiomyopathy, and valvular heart disease. Evidence has also been shown of apoptosis in heart failure resulting from arrhythmogenic right ventricular dysplasia. For all these disorders, see Hetts, above. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses.

Disorders involving the kidney include, but are not limited to, congenital anomalies including, but not limited to, cystic diseases of the kidney, that include but are not limited to, cystic renal dysplasia, polycystic kidney diseases, and cystic diseases of renal medulla; glomerular diseases including pathologies of glomerular injury that include, but are not limited to, in situ immune complex deposition, that includes, but is not limited to, anti-GBM nephritis, Heymann nephritis and other nephritis conditions, glomerulonephritis conditions, minimal change disease (lipoid nephrosis), focal segmental glomerulosclerosis, IgA nephropathy (Berger disease); glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, hemolytic-uremic syndromes, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders involving the prostate include, but are not limited to, an abnormal condition occurring in the male pelvic region characterized by, e.g., male sexual dysfunction and/or urinary symptoms, inflammations, including genitourinary inflammation, benign enlargement, for example, nodular hyperplasia (benign prostatic hypertrophy or hyperplasia), prostatitis, and tumors such as carcinoma or adenocarcinoma.

As used herein, "differential expression" or differentially expressed" includes both quantitative and qualitative differences in the temporal and/or cellular expression pattern of a gene, e.g., the protein kinase gene disclosed herein, among, for example, normal cells and cells undergoing programmed cell death, cell division or cell cycle progression. Genes which are differentially expressed can be used as part of a prognostic or diagnostic marker for the evaluation of subjects at risk for developing a disorder characterized by deregulated programmed cell death, cell division or cell cycle progression. Depending on the expression level of the gene, such as the level of 14171 expression, the progression state of the disorder can also be evaluated.

The present invention is based, at least in part, on the identification of a novel kinase protein and nucleic acid molecule that comprises a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence identity as defined herein. Such family members can be naturally or non-naturally occurring and can be from either the same or different species. For example, a family can contain a first protein of human origin, as well as other, distinct proteins of human origin or alternatively, can contain homologs of non-human origin. Members of a family may also have common functional characteristics.

One embodiment of the invention features a 14171 protein kinase nucleic acid molecule, preferably a human protein kinase molecule, identified based on a consensus motif or protein domain characteristic of a protein kinase family of proteins, specifically, a serine/threonine protein kinase also containing ankyrin function, or a RIP kinase.

Novel Protein Kinase Sequence

The protein kinase gene of the invention was identified in a human primary osteoblast cDNA library. The 14171 clone set forth in SEQ ID NO:1 is approximately 3860 nucleotides long including untranslated regions and comprises a corresponding cDNA sequence set forth in SEQ ID NO:3. This transcript has a nucleotide open reading frame encoding an amino acid of about 784 amino acids, set forth in SEQ ID NO:2. The methionine-initiated coding sequence of about 2355 nucleotides (nucleotides 17-2371 of SEQ ID NO:1) for 14171 is shown in SEQ ID NO:3.

Analysis of the 14171 polypeptide reveals one protein kinase domain and ten ankyrin repeats, as described further below; a spacer region, rich in serine and threonine residues, phosphorylation of which can lead to regulation of activity of a 14171 protein kinase, at about amino acids 289 to 437 of SEQ ID NO:2; three glycosylation sites (Prosite PS00001) at about amino acids 465 to 468, 527 to 530, and 703 to 706 of SEQ ID NO:2; a glycosaminoglycan attachment site (Prosite PS00002) at about amino acids 365 to 368 of SEQ ID NO:2; four cAMP and cGMP dependent protein kinase phosphorylation sites (Prosite PS00004) at about amino acids 319 to 322, 369 to 372, 469 to 472, and 493 to 496 of SEQ ID NO:2; ten protein kinase C phosphorylation sites (Prosite PS00005) at about amino acids 218 to 220, 367 to 369, 382 to 384, 402 to 404, 419 to 421, 467 to 469, 519 to 521, 652 to 654, 685 to 687, and 765 to 767 of SEQ ID NO:2; twelve casein kinase II phosphorylation sites (Prosite PS00006) at about amino acids 23 to 26, 202 to 205, 275 to 278, 281 to 284, 297 to 300, 305 to 308, 331 to 334, 337 to 340, 356 to 359, 375 to 378, 396 to 399, and 529 to 532 of SEQ ID NO:2; nine N-myristoylation sites (Prosite PS00008) at about amino acids 6 to 11, 163 to 168, 169 to 174, 180 to 185, 342 to 347, 449 to 454, 560 to 565, 594 to 599, and 758 to 763 of SEQ ID NO:2; an amidation site (Prosite PS00009) at about amino acids 367 to 370 of SEQ ID NO:2; a protein kinase ATP binding region signature (Prosite PS00107, SEQ ID NO:5) at about amino acids 28 to 51 of SEQ ID NO:2; a serine/threonine protein kinase active site signature (Prosite PS00108, SEQ ID NO:6) at about amino acids 139 to 151 of SEQ ID NO:2; and a eukaryotic and viral aspartyl protease active site (Prosite PS00141, SEQ ID NO:7) at about amino acids 433 to 444 of SEQ ID NO:2. In the case of glycosylation, the actual modified residue is the first amino acid of the indicated site. In the case of cAMP and cGMP dependent protein kinase phosphorylation, the actual modified residue is the last amino acid in the indicated site. In the case of protein kinase C phosphorylation, the actual modified residue is the first amino acid in the indicated sites. In the case of casein kinase II phosphorylation, the actual modified residue is the first amino acid in the indicated sites. In the case of N-myristoylation, the actual modified residue is the first amino acid in the indicated site. In one embodiment, the 14171 kinase is phosphorylated.

For general information regarding PFAM identifiers, PS prefix and PF prefix domain identification numbers, refer to Sonnhammer et al. (1997) *Protein* 28:405-420, the Pfam website maintained in several locations, e.g. by the Sanger Institute (pfam.sanger.ac.uk), Washington University (pfam.wustl.edu), the Karolinska Institute (pfam.cgr.kr.se) or Institut de la National Recherche Agronomique (pfamjouy.inra.fr) and for Prosite (PS), the ExPASy (Expert Protein Analysis System) proteomics server of the Swiss Institute of Bioinformatics (SIB), Geneva, Switzerland.

As use herein, the term "protein kinase domain" includes an amino acid sequence of about 200-400 amino acid residues in length and having a bit score for the alignment of the sequence to the protein kinase domain (HMM) of at least 8 or 100. Preferably, a protein kinase domain includes at least about 200-300 amino acids, more preferably about 250 to 300 amino acid residues, and has a bit score for the alignment of the sequence to the protein kinase domain (HMM) of at least 16, 130, 160, 185 or greater. Preferably a protein kinase domain mediates catalysis of protein phosphorylation and can mediate the interaction with other domains, e.g., cyclin domains, kinase domains or ankyrin repeat domains. The protein kinase domain (HMM) has been assigned the PFAM Accession PF00069 (SEQ ID NO:4). An alignment of the protein kinase domain (amino acids 22 to 279 of SEQ ID NO:2) of human 14171 protein kinase with a consensus amino acid sequence (SEQ ID NO:4) derived from a hidden Markov model yields a bit score of 187.5.

Eukaryotic protein kinases (described in, for example, Hanks et al. (1995) *FASEB J.* 9:576-596) are enzymes that belong to an extensive family of proteins that share a conserved catalytic core common to both serine/threonine and tyrosine protein kinases. There are a number of conserved regions in the catalytic domain of protein kinases. One of these regions, located in the N-terminal extremity of the catalytic domain, is a glycine-rich stretch of residues in the vicinity of a lysine residue, which has been shown to be involved in ATP binding. The consensus sequence for this region (Prosite PS00107) is [LIV]-G-{P}-G-{P}-[FYW-MGSTNH]-[SGA]-{PW}-[LIVCAT]-{PD}-x[GSTA-CLIVMFY]-x(5,18)-[LIVMFYWCSTAR]-[AIVP]-[LIVM-FAGCKR]-K (SEQ ID NO:5; K, the active site lysine, can bind the phosphate donor nucleotide, e.g., adenosine triphosphate). A region in the 14171 polypeptide matching this consensus can be found at about amino acids 28 to 51 of SEQ ID NO:2, and K-51 SEQ ID NO:2 can be involved in ATP binding for the 14171 polypeptide). Experiments described herein examined the substitution of K-51 to A by mutating nucleotides bases 167 and 168 of SEQ ID NO:1 from adenine to guanine and cytosine, respectively, so the codon for amino acid residue 51 of SEQ ID NO:2 is GCG instead of the wild type AAG. The results of those experiments demonstrated loss of 14171 kinase activity with A instead of K at residue 51 of SEQ ID NO:2. Thus, further embodiments of the invention are a substitution for K at residue 51 of SEQ ID NO:2 and nucleic acid sequences encoding the substitution. In the above conserved signature sequence, and other motifs or signature sequences described herein, the standard IUPAC one-letter code for the amino acids is used. Each element in the pattern is separated by a dash (–); square brackets ([ ]) indicate the particular residues that are accepted at that position; cursive brackets ({ }) indicate that the residue(s) within are not present in every sequence contributing to the consensus; x indicates that any residue is accepted at that position; and numbers in parentheses (()) indicate the number of residues represented by the accompanying amino acid.

Another region, located in the central part of the catalytic domain, contains a conserved aspartic acid residue which is important for the catalytic activity of the enzyme (Knighton et al. (1991) *Science* 253:407-414). Two signature patterns have been described for this region: one specific for serine/threonine kinases and one for tyrosine kinases. The 14171 protein kinase has a sequence more closely matching the pattern for serine/threonine kinases (Prosite PS00108), [LIVMFYC]-x-[HY]-x-D-[LIVWMFY]-K-x(2)-N-[LIVM-FYCT](3) (SEQ ID NO:6; D is an active site residue). This sequence can be found at about amino acids 139 to 151 of SEQ ID NO:2, and D-143 SEQ ID NO:2 can be the active site residue for 14171. Embodiments of the invention are a substitution for D at residue 143 of SEQ ID NO:2 and nucleic acid sequences encoding the substitution.

In a preferred embodiment human 14171 protein kinase-like polypeptide or protein has a "protein kinase domain" or a region which includes at least about 200 to 400 more preferably about 200 to 300, 250 to 300 or 250 to 260 amino acid residues and has at least about 60%, 70%, 80%, 90%, 95%, 99%, or 100% sequence identity with a "protein kinase domain," e.g., the protein kinase domain of human 14171 protein kinase-like polypeptides (e.g., amino acid residues 22 to 279 of SEQ ID NO:2).

As used herein, the term "ankyrin repeat" domain includes an amino acid sequence of about 2 to 150 amino acid residues in length and having a bit score for the alignment of the sequence to the ankyrin repeat domain (HMM) of at least 8. Preferably, an ankyrin repeat domain includes at least about 5 to 100 amino acids, more preferably about 5 to 50 amino acid residues, about 5 to 45 or about 25 to 35 amino acids and has a bit score for the alignment of the sequence to the ankyrin repeat domain (HMM) of at least 15, 16, 20, 25 or greater. The ankyrin repeat domain (HMM) has been assigned the PFAM Accession PF00023 (SEQ ID NO:8). Preferably an ankyrin repeat domain is tandemly repeated in an ankyrin repeat region which mediates interactions with other proteins, e.g., kinases, transcription factors, integrins, receptors, or channel subunits. The presence of both a protein kinase domain and ankyrin repeat domains in the 14171 polypeptide suggests that 14171 can bind itself or other proteins. The ankyrin repeats are predicted to be between amino acid residues 437-469, 470-502, 503-535, 536-568, 569-602, 603-635; 636-668; 669701; 702-730; and 734-766 of SEQ ID NO:2. Alignments of the ankyrin repeat domains of human 14171 protein kinase with a consensus amino acid sequence (SEQ ID NO:8) derived from a hidden Markov model yields a bit scores of 37.0, 34.7, 37.5, 44.0, 30.3, 44.1, 30.6, 44.6, 25.2, and 38.4, respectively.

In a preferred embodiment 14171 protein kinase-like polypeptide or protein has at least one, two, three, four, five, six, seven, eight, nine, preferably ten "ankyrin repeat domains" or regions which include at least about 2-150 more preferably about 5-100 or 5-50 amino acid residues and has at least about 60%, 70%, 80%, 90%, 95%, 99%, or 100% sequence identity with an "ankyrin repeat domain," e.g., the ankyrin repeat domains of human 14171 (e.g., amino acid residues 437-469, 470-502, 503-535, 536-568, 569-602, 603635; 636-668; 669-701; 702-730; and 734-766 of SEQ ID NO:2).

To identify the presence of an "protein kinase" or an "ankyrin repeat" domain in a 14171-like protein sequence, and make the determination that a polypeptide or protein of interest has a particular profile, the amino acid sequence of the protein can be searched against a database of HMMs (e.g., the Pfam database, release 2.1) using the default parameters (see website maintained in several locations, e.g. by the Sanger Institute (pfam.sanger.ac.uk), Washington University (pfam.wustl.edu), the Karolinska Institute (pfam-.cgr.kr.se) or Institut de la National Recherche Agronomique (pfamjouy.inra.fr)). For example, the hmmsf program, which is available as part of the HMMER package of search programs, is a family specific default program for MIL-PAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314, the contents of which are incorporated herein by reference.

Preferred kinase polypeptides of the present invention have an amino acid sequence sufficiently identical to the amino acid sequence of SEQ ID NO:2 or a domain thereof.

The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity or there are conservative substitutions of aligned amino acid residues in a second amino acid sequence such that the first and second amino acid sequences can have a common structural domain and/or common functional activity. For example, amino acid or nucleotide sequences that contain a common structural domain having at least about 60%, 65%, 70%, 75%, 80%, 85%, 90%, 95%, 96%, 97%, 98%, or 99% identity are defined herein as sufficiently identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1 or 3 are termed substantially identical.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48:444-453 algorithm which has been incorporated into the GAP program in the GCG software package (available at the bioinformatics page of the website maintained by Accelrys, Inc., San Diego, Calif., USA), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (1989) *CABIOS* 4:11-17 which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to 14171 protein kinase nucleic acid molecules of the invention. BLAST protein searches can be performed with the XBLAST program, score=50, wordlength=3 to obtain amino acid sequences homologous to 14171 protein kinase protein molecules of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used (accessible at the website maintained by National Center for Biotechnology Information, Bethesda, Md., USA (ncbi.nlm.nih.gov)).

Accordingly, another embodiment of the invention features isolated protein kinase proteins and polypeptides having a protein kinase protein activity. As used interchangeably herein, a "protein kinase protein activity", "biological activity of a protein kinase protein", or "functional activity of a protein kinase protein" refers to an activity exerted by a protein kinase protein, polypeptide, or nucleic acid molecule on a protein kinase-responsive cell as determined in vivo, or in vitro, according to standard assay techniques. A protein kinase activity can be a direct activity, such as an association with or an enzymatic activity on a second protein, such as on nuclear factor-κB or Jun N-terminal kinase, or an indirect activity, such as a cellular signaling activity mediated by interaction of the protein kinase protein with a second protein, such as the induction of cellular signals resulting in cell growth, differentiation, and death that is mediated by members of the tumor necrosis factor receptor superfamily, for example, as discussed hereinabove. In a preferred embodiment, a protein kinase activity includes at least one or more of the following activities:(1) modulating (stimulating and/or enhancing or inhibiting) cellular proliferation, growth and/or metabolism (e.g., in those cells in which the sequence is expressed, including virus-infected cells); (2) the regulation of transmission of signals from cellular receptors, e.g., growth factor receptors; (3) the modulation of the entry of cells into mitosis; (4) the modulation of cellular differentiation; (5) the modulation of cell death; and (6) the regulation of cytoskeleton function, e.g., actin bundling. Functions also include, but are not limited to, those shown for the specific functional sites described above, including ATP binding, protein phosphorylation and ankyrin function.

An "isolated" or "purified" protein kinase nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein-encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated kinase nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A kinase protein that is substantially free of cellular material includes preparations of kinase protein having less than about 30%, 20%, 10%, or 5% (by dry weight) of non-kinase protein (also referred to herein as a "contaminating protein"). When the kinase protein or biologically active portion thereof is recombinantly produced, preferably, culture medium represents less than about 30%, 20%, 10%, or 5% of the volume of the protein preparation. When kinase protein is produced by chemical synthesis, preferably the protein preparations have less than about 30%, 20%, 10%, or 5% (by dry weight) of chemical precursors or non-kinase chemicals.

Various aspects of the invention are described in further detail in the following subsections.

Isolated Nucleic Acid Molecules

One aspect of the invention pertains to an isolated nucleic acid molecule comprising a nucleotide sequence encoding a protein kinase protein or biologically active portion thereof, as well as a nucleic acid molecule sufficient for use as a hybridization probe to identify kinase-encoding nucleic acids (e.g., the kinase mRNA) and fragments for use as PCR primers for the amplification or mutation of kinase nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

In one embodiment, an isolated nucleic acid molecule of the invention includes the nucleotide sequence shown in SEQ ID NO:1, or a portion of any of this nucleotide sequence. In one embodiment, the nucleic acid molecule includes sequences encoding the human 14171 protein (i.e., "the coding region" of SEQ ID NO:1, as shown in SEQ ID NO:3), as well as 5' untranslated sequences (nucleotides 1 to 16 of SEQ ID NO:1) and 3' untranslated sequences (nucleotides 2291 to 3860 of SEQ ID NO:1). Alternatively, the nucleic acid molecule can include only the coding region of SEQ ID NO:1 (e.g., SEQ ID NO:3) and, e.g., no flanking sequences which normally accompany the subject sequence. In another embodiment, the nucleic acid molecule encodes a sequence corresponding to a fragment of the protein from about amino acid 22 to 279 of SEQ ID NO:2, or a fragment thereof, e.g., about amino acid residues 22 to 100, 101 to 190, or 191 to 279 of SEQ ID NO:2.

A nucleotide sequence encoding the kinase proteins of the present invention includes the sequences set forth in SEQ ID NO:1, SEQ ID NO:3, and the complements thereof. By "complement" is intended a nucleotide sequence that is sufficiently complementary to a given nucleotide sequence such that it can hybridize to the given nucleotide sequence to thereby form a stable duplex. The corresponding amino acid sequence for the kinase protein encoded by the nucleotide sequence is set forth in SEQ ID NO:2.

Nucleic acid molecules that are fragments of the kinase nucleotide sequence are also encompassed by the present invention. By "fragment" is intended a portion of the nucleotide sequence encoding a kinase protein of the invention. A fragment of a kinase nucleotide sequence may encode a biologically active portion of a kinase protein, or it may be a fragment that can be used as a hybridization probe or PCR primer using methods disclosed below. A biologically active portion of the kinase protein can be prepared by isolating a portion of the kinase nucleotide sequence of the invention, expressing the encoded portion of the kinase protein (e.g., by recombinant expression in vitro), and assessing the activity of the encoded portion of the kinase protein. Generally, nucleic acid molecules that are fragments of a protein kinase nucleotide sequence comprise at least 15, 20, 50, 75, 100, 325, 350, 375, 400, 425, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, or up to 3860 nucleotides present in the nucleotide sequence disclosed herein. Alternatively, a nucleic acid molecule that is a fragment of a 14171-like nucleotide sequence of the present invention comprises a nucleotide sequence consisting of nucleotides 1-100, 100-200, 200-300, 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2200, 2200-2300, 2300-2400, 2400-2500, 2500-2600, 2600-2700, 2700-2800, 2800-2900, 2900-3000, 3000-3100, 3100-3200, 3200-3300, 3300-3400, 3400-3500, 3500-3600, 3600-3700, 3700-3800, 3800-3860 of SEQ ID NO:1.

It is understood that isolated fragments include any contiguous sequence not disclosed prior to the invention as well as sequences that are substantially the same and which are not disclosed. Accordingly, if a fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences. Further, the sizes of the fragments may vary depending on the region analyzed. In the present case, fragments can include as few as 510, or 10-20 nucleotides from nucleotide 1 to approximately 962, and approximately 1700 to approximately 2518. Similarly, amino acid fragments encompassed by these regions can include as few as 4-10, 10-15, 15-20, 20-30, and 30-40 amino acids.

A nucleic acid fragment can include a sequence corresponding to a domain, region, or functional site described herein. A nucleic acid fragment can also include one or more domain, region, or functional site described herein. Thus, for example, a 14171 nucleic acid fragment can include a sequence corresponding to a protein kinase domain, at about amino acid residues 22 to 279 of SEQ ID NO:2 or to an ankyrin repeat domain, at about amino acid residues 437-469, 470-502, 503-535, 536-568, 569-602, 603-635; 636-668; 669701; 702-730; and 734-766 of SEQ ID NO:2 as described herein. In one embodiment, a fragment can be a nucleic acid comprising nucleotides 167 to 169, preferably nucleotides 98 to 169, or 77 to 181 of SEQ ID NO:1 or can be an amino acid sequence comprising residue 51, preferably amino acids 28 to 51 or 21 to 55 of SEQ ID NO:2. In another embodiment, a fragment can be a nucleic acid comprising nucleotides 443 to 445, preferably nucleotides 431 to 469, or of SEQ ID NO:1 or can be an amino acid sequence comprising residue 143, preferably amino acids 139 to 151 of SEQ ID NO:2.

Generally, a fragment of a kinase nucleotide sequence that encodes a biologically active portion of a kinase protein of the invention will encode at least 15, 25, 30, 50, 75, 100, 125, 150, 170, 200, 250, 300, 350, 400, 450, or 500 contiguous amino acids, or up to the total number of amino acids present in a full-length kinase protein of the invention. Fragments of a kinase nucleotide sequence that are useful as hybridization probes for PCR primers generally need not encode a biologically active portion of a kinase protein. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or SEQ ID NO:3, or of a naturally occurring allelic variant or mutant of SEQ ID NO:1 or SEQ ID NO:3.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: a protein kinase domain, at about amino acid residues 22 to 279 of SEQ ID NO:2 or an ankyrin repeat domain, at about amino acid residues 437-469, 470-502, 503-535, 536-568, 569-602, 603-635; 636-668; 669-701; 702-730; and 734-766 of SEQ ID NO:2. In other embodiments, primers and/or probes, e.g., comprising nucleotide sequences in SEQ ID NO:9, SEQ ID NO:10 or SEQ ID NO:11, can be used for expression analysis and/or diagnostic purposes.

In another embodiment a set of primers is provided, e.g., primers suitable for use in a PCR, which can be used to amplify a selected region of a 14171 sequence, e.g., a domain, region, site or other sequence described herein. The primers should be at least 5, 10, or 50 base pairs in length and less than 100, or less than 200, base pairs in length. The primers should be identical, or differ by one base from a sequence disclosed herein or from a naturally occurring variant. For example, primers suitable for amplifying all or a portion of any of the following regions are provided: a protein kinase domain, at about amino acid residues 22 to 279 of SEQ ID NO:2 or an ankyrin repeat domain, at about amino acid residues 437-469, 470-502, 503-535, 536-568, 569-602, 603-635; 636-668; 669-701; 702730; and 734-766 of SEQ ID NO:2. In another example, primers can be used to construct a cDNA clone and can have the sequences comprising SEQ ID NO:12 and SEQ ID NO:13.

Nucleic acid molecules that are variants of the kinase nucleotide sequence disclosed herein are also encompassed by the present invention. "Variants" of the kinase nucleotide sequence include those sequences that retain the biological activity of the protein kinase set forth in SEQ ID NO:2 but that differ conservatively because of the degeneracy of the genetic code. These naturally-occurring allelic variants can be identified with the use of well-known molecular biology techniques, such as polymerase chain reaction (PCR) and hybridization techniques as outlined below. Variant nucleotide sequences also include synthetically-derived nucleotide sequences that have been generated, for example, by using site-directed mutagenesis but which still encode the kinase protein disclosed in the present invention as discussed below. Generally, nucleotide sequence variants of the invention will have at least 60%, 65%, 70%, 75%, 80%, 85%, 90%, 91%, 92%, 93%, 94%, 95%, 96%, 97%, 98%, or 99% identity to the nucleotide sequence disclosed herein. A variant kinase nucleotide sequence will encode a protein kinase that has the amino acid sequence having at least 60%, 65%, 70%, 75%, 80%, 85%, 90%, 91%, 92%, 93%, 94%, 95%, $$ 96%, 97%, 98%, or 99% identity to the amino acid sequence of the protein kinase disclosed herein and retains the biological activity of the protein kinase.

In addition to the kinase nucleotide sequence shown in SEQ ID NO:1, it will be appreciated by those skilled in the art that DNA sequence polymorphisms that lead to changes in the amino acid sequences of the kinase protein may exist within a population (e.g., the human population). Such genetic polymorphism in a protein kinase gene of the invention may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding a protein kinase protein, preferably a mammalian protein kinase protein. As used herein, the phrase "allelic variant" refers to a nucleotide sequence that occurs at a protein kinase locus or to a polypeptide encoded by the nucleotide sequence. Such natural allelic variations can typically result in 1-5% variance in the nucleotide sequence of the kinase gene. Any and all such nucleotide variations and resulting amino acid polymorphisms or variations in a kinase sequence that are the result of natural allelic variation and that do not alter the functional activity of kinase proteins are intended to be within the scope of the invention.

Moreover, nucleic acid molecules encoding kinase protein from other species (kinase homologs), which have a nucleotide sequence differing from that of the kinase sequence disclosed herein, are intended to be within the scope of the invention. Nucleic acid molecules corresponding to natural allelic variants and homologs of the kinase cDNA of the invention can be isolated based on their identity to the kinase nucleic acid disclosed herein using the cDNA, or a portion thereof, as a hybridization probe according to standard hybridization techniques under stringent hybridization conditions as disclosed below.

In addition to naturally-occurring allelic variants of the kinase sequence that may exist in the population, the skilled artisan will further appreciate that changes can be introduced by mutation into the nucleotide sequences of the invention thereby leading to changes in the amino acid sequence of the encoded kinase protein, without altering the biological activity of the kinase protein. Thus, an isolated nucleic acid molecule encoding a protein kinase protein having a sequence that differs from that of SEQ ID NO:2 can be created by introducing one or more nucleotide substitutions, additions, or deletions into the nucleotide sequences disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a protein kinase protein (e.g., the sequence of SEQ ID NO:2) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues or for amino acid residues residing within a conserved protein domain, such as the serine/threonine protein kinase domain of the disclosed clones, where such residues are essential for protein activity.

Alternatively, variant kinase nucleotide sequences can be made by introducing mutations randomly along all or part of the kinase coding sequence, such as by saturation mutagenesis, and the resultant mutants can be screened for kinase biological activity to identify mutants that retain activity. In another alternative, specific mutations can be introduced, e.g., by site-directed mutagenesis, to change the biological activity of the 14171 molecules of the invention. For example, changes can be made in the protein kinase domain or in one, two, three, four, five, six, seven, eight, nine or ten ankyrin repeat domains of 14171 protein kinase. As an example of a change in the protein kinase domain, nucleotides in the codon encoding K 51 of SEQ ID NO:2 can be changed, e.g., changes in nucleotides 167, 168 or 169 of SEQ ID NO:1 or nucleotides 151, 152 or 153 of SEQ ID NO:3 can inhibit a biological activity, e.g., protein phosphorylation activity, of a 14171 polypeptide. As another example, nucleotides in the codon encoding D 143 of SEQ ID NO:2 can be changed, e.g., changes in nucleotides 443, 444 or 445 of SEQ ID NO:1 or nucleotides 427, 428, or 429 of SEQ ID NO:3 can inhibit a biological activity, e.g., protein phosphorylation activity, of a 14171 polypeptide. In further examples, nucleotides in regions of SEQ ID NO:1 or SEQ ID NO:3 encoding the ankyrin repeat domains, e.g., nucleotides encoding amino acid residues in regions of amino acids 437-469, 470-502, 503-535, 536-568, 569-602, 603-635; 636-668; 669-701; 702-730; and 734-766 of SEQ ID NO:2 can be changed to alter protein or membrane association activity of a 14171 polypeptide. Following mutagenesis, the encoded protein can be expressed recombinantly, and the activity of the protein can be determined using standard assay techniques.

Thus the nucleotide sequence of the invention includes the sequence disclosed herein as well as fragments and variants thereof. The kinase nucleotide sequence of the invention, and fragments and variants thereof, can be used as a probe and/or primer to identify and/or clone kinase homologs in other cell types, e.g., from other tissues, as well as kinase homologs from other mammals. Such probes can be used to detect transcripts or genomic sequences encoding the same or identical proteins. These probes can be used as part of a diagnostic test kit for identifying cells or tissues that misexpress a kinase protein, such as by measuring levels of a kinase-encoding nucleic acid in a sample of cells from a subject, e.g., detecting kinase mRNA levels or determining whether a genomic kinase gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). Kinase nucleotide sequences isolated based on their sequence identity to the kinase nucleotide sequence set forth herein or to fragments and variants thereof are encompassed by the present invention.

In a hybridization method, all or part of a known kinase nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known kinase nucleotide sequences disclosed herein. Degenerate primers designed on the basis of conserved nucleotides or amino acid residues in a known kinase nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of a kinase nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified kinase nucleic acid molecule hybridizes under stringent conditions to a probe that is a nucleic acid molecule comprising the kinase nucleotide sequence of the invention or a fragment thereof. In another embodiment, the previously unknown kinase nucleic acid molecule is at least 300, 325, 350, 375, 400, 425, 450, 500, 550, 600, 650, 700, 800, 900, 1000, 2,000, 3,000, or 4,000 nucleotides in length and hybridizes under stringent conditions to a probe that is a nucleic acid molecule comprising the kinase nucleotide sequence disclosed herein or a fragment thereof.

Accordingly, in another embodiment, an isolated previously unknown kinase nucleic acid molecule of the invention is at least 300, 325, 350, 375, 400, 425, 450, 500, 518, 550, 600, 650, 700, 800, 831, 900, 981, 1000, 1,100, 1,200, 1,300, 1,400, 1,500, 1,600, 1,700, 1,800, 1,900, 2,000, or 2,060 nucleotides in length and hybridizes under stringent conditions to a probe that is a nucleic acid molecule comprising one of the nucleotide sequences of the invention, preferably the coding sequence set forth in SEQ ID NO:1 or a complement, fragment, or variant thereof.

As used herein, the term "hybridizes under stringent conditions" is intended to describe conditions for hybridization and washing. Stringent conditions are known to those skilled in the art and can be found in *Current Protocols in Molecular Biology* John Wiley & Sons, N.Y. (1989), 6.3.1-6.3.6. Aqueous and nonaqueous methods are described in that reference and either can be used. A preferred, example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:1, or SEQ ID NO:3, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

Thus, in addition to the kinase nucleotide sequence disclosed herein and fragments and variants thereof, the isolated nucleic acid molecule of the invention also encompasses homologous DNA sequences identified and isolated from other cells and/or organisms by hybridization with entire or partial sequences obtained from the kinase nucleotide sequence disclosed herein or variants and fragments thereof.

As used herein, "heterologous" in reference to a polypeptide or amino acid sequence is a polypeptide or amino acid sequence that originates from a foreign protein, or, if from the same protein, is substantially modified from its native form in composition by deliberate human intervention. A heterologous protein may originate from a foreign species, or, if from the same species, is substantially modified from its original form by deliberate human intervention.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire kinase coding strand, or to only a portion thereof, e.g., all or part of the protein coding region (or open reading frame). An antisense nucleic acid molecule can be antisense to a noncoding region of the coding strand of a nucleotide sequence encoding a kinase protein. The noncoding regions are the 5' and 3' sequences that flank the coding region and are not translated into amino acids.

Given the coding-strand sequence encoding the kinase protein disclosed herein (e.g., SEQ ID NO:1), antisense nucleic acids of the invention can be designed according to the rules of Watson and Crick base pairing. The antisense nucleic acid molecule can be complementary to the entire coding region of kinase mRNA, but more preferably is an oligonucleotide that is antisense to only a portion of the coding or noncoding region of kinase mRNA. For example, the antisense oligonucleotide can be complementary to the region surrounding the translation start site of kinase mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids, including, but not limited to, for example, phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules of the invention are typically administered to a subject or generated in situ such that they hybridize with or bind to cellular mRNA and/or genomic DNA encoding a kinase protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific doublestranded hybrids with complementary RNA in which, contrary to the usual β-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585-591)) can be used to catalytically cleave kinase mRNA transcripts to thereby inhibit translation of kinase mRNA. A ribozyme having specificity for a kinase-encoding nucleic acid can be designed based upon the nucleotide sequence of a kinase cDNA disclosed herein (e.g., SEQ ID NO:1). See, e.g., Cech et al., U.S. Pat. No. 4,987,071; and Cech et al., U.S. Pat. No.

5,116,742. Alternatively, kinase mRNA can be used to select a catalytic RNA having a specific ribonuclease activity from a pool of RNA molecules. See, e.g., Bartel and Szostak (1993) *Science* 261:1411-1418.

The invention also encompasses nucleic acid molecules that form triple helical structures. For example, kinase gene expression can be inhibited by targeting nucleotide sequences complementary to the regulatory region of the kinase protein (e.g., the kinase promoter and/or enhancers) to form triple helical structures that prevent transcription of the kinase gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

The invention also encompasses RNA inhibitors, e.g., small interfering RNAs (siRNAs), double-stranded RNA molecules which interfere with the translation of homologous mRNAs (reviewed by Hannon, G. J. (2002) *Nature* 418:244-251). siRNAs can be devised based on sequences of about 10 to 500 nucleotides, preferably 15 to 50, or about 20 nucleotides from the coding region of a gene, e.g. SEQ ID NO:3. siRNAs can further include heterologous nucleotide, e.g., DNA or RNA sequences at the 3' ends of the strands. For example, 14171 protein kinase gene expression can be inhibited by the presence of siRNAs with homology to at least one sequence on the 14171 mRNA. For example, inhibition of 14171 expression can result from the presence of siRNAs which target the sequence AAGAACATCCTG-CACATCATG, SEQ ID NO:21, beginning at residue 679 of SEQ ID NO:3, AAGAAGATGGAGATGGCCAAG, SEQ ID NO:22, beginning at residue 211 of SEQ ID NO:3 or AACCTTCAACCAGCGATCTGG, SEQ ID NO:23, beginning at residue 1181 of SEQ ID NO:3. Examples siRNA molecules which modulate the expression and/or the activity of 14171 protein kinase are represented herein as SEQ ID NOs:24, 25, 26, 27, 28, and 29.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) *Proc. Natl. Acad. Sci. USA* 93:14670.

PNAs of a kinase molecule can be used in therapeutic and diagnostic applications. For example, PNAs can be used as antisense or antigen agents for sequencespecific modulation of gene expression by, e.g., inducing transcription or translation arrest or inhibiting replication. PNAs of the invention can also be used, e.g., in the analysis of single base pair mutations in a gene by, e.g., PNA-directed PCR clamping, as artificial restriction enzymes when used in combination with other enzymes, e.g., S1 nucleases (Hyrup (1996), supra, or as probes or primers for DNA sequence and hybridization (Hyrup (1996), supra; Perry-O'Keefe et al. (1996), supra).

In another embodiment, PNAs of a kinase molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357-63; Mag et al. (1989) *Nucleic Acids Res.* 17:5973; and Peterser et al. (1975) *Bioorganic Med. Chem. Lett.* 5:1119.

Isolated Protein Kinase Proteins and Anti-protein Kinase Antibodies

Protein kinase proteins are also encompassed within the present invention. The invention encompasses a protein having the amino acid sequence set forth in SEQ ID NO:2, fragments, and variants thereof that retain the biological activity of the protein kinase. In one embodiment, the protein includes an amino acid sequence at least about 60%, 65%, 70%, 75%, 80%, 85%, 90%, 95%, 98% or more homologous to SEQ ID NO:2. The invention also encompasses variants of SEQ ID NO:2 which specifically alter one or more activities of the 14171 protein kinase.

In a preferred embodiment, a 14171 polypeptide has one or more of the following characteristics:

it has the ability to bind a molecule, e.g., a nucleotide (e.g., adenosine triphosphate);

the ability to bind a protein substrate, e.g., a serine or threonine-containing protein;

the ability to catalyze the transfer of a functional group, e.g., a phosphate, from the nucleotide to the protein, e.g., to a serine or threonine residue on the protein;

the ability to regulate transmission of signals from cellular receptors, e.g., cell growth factor receptors;

it has a molecular weight, e.g., a deduced molecular weight, preferably ignoring any contribution of post translational modifications, amino acid composition or other physical characteristic of an 14171 polypeptide, e.g., a polypeptide of SEQ ID NO:2;

it has an overall sequence similarity of at least 60%, preferably at least 70%, more preferably at least 80, 90, or 95%, with a polypeptide of SEQ ID NO:2;

it is expressed in at least kidney, prostate epithelial cells or lung tumor tissue;

it can activate NF-κB activity;

its expression or activity can be regulated by p53;

it has a protein kinase domain which is preferably about 70%, 80%, 90% or 95% identical to amino acid residues about 22 to 279 of SEQ ID NO:2; and it has an ankyrin repeat domain which is preferably about 70%, 80%, 90% or 95% identical to amino acid residues about 437-469, 470-502, 503-535, 536-568, 569-602, 603-635; 636-668; 669-701; 702-730; and 734-766 of SEQ ID NO:2.

"Fragments" or "biologically active portions" include polypeptide fragments suitable for use as immunogens to raise anti-kinase antibodies. Fragments include peptides comprising amino acid sequences sufficiently identical to or derived from the amino acid sequences of a kinase protein of the invention and exhibiting at least one activity of a kinase protein, but which include fewer amino acids than the full-length kinase protein disclosed herein. Typically, biologically active portions comprise a domain or motif with at least one activity of the kinase protein. A biologically active portion of a kinase protein can be a polypeptide which is, for example, 10, 13, 24, 25, 30, 32, 50, 100, 150, 200, 250, 300, 350, 400, 450, 500 or more amino acids in length. Such biologically active portions can be prepared by recombinant techniques and evaluated for one or more of the functional activities of a native kinase protein.

In one embodiment, the protein includes fragments or regions homologous to fragments, at least about 70%, 80%, 90%, 95%, 96%, 97%, 98%, 99% or more homologous to a fragment of SEQ ID NO:2. A fragment of a 14171 protein kinase can comprise a domain, e.g., a protein kinase domain at about amino acid residues 22 to 279 of SEQ ID NO:2 or a fragment thereof, e.g., about amino acid residues 22 to 160, 161 to 220, or 221 to 279 of SEQ ID NO:2. Alternatively, a fragment can comprise one or more, e.g., two, three, four, five, six, seven, eight, nine or ten, of an ankyrin repeat domain, e.g., about amino acid residues 437-469, 470-502, 503-535, 536-568, 569-602, 603-635; 636-668; 669-701; 702-730; and 734-766 of SEQ ID NO:2. Optionally, a fragment of a 14171 protein kinase can further comprise a spacer region, at about amino acid residues 289 to 437 of SEQ ID NO:2, or a portion thereof, e.g., about amino acid residues 289 to 350, 289 to 437 of SEQ ID NO:2. Preferred fragments of a 14171 protein kinase have the sequence of amino acids 1 to 350 or 1 to 450 of SEQ ID NO:2.

By "variants" is intended proteins or polypeptides having an amino acid sequence that is at least about 60%, 65%, 70%, preferably about 75%, 85%, 95%, or 98% identical to the amino acid sequence of SEQ ID NO:2. Variants also include polypeptides encoded by a nucleic acid molecule that hybridizes to the nucleic acid molecule of SEQ ID NO:1, SEQ ID NO:3, or a complement thereof, under stringent conditions. Variants can retain the biological activity (e.g., the protein kinase activity) of the polypeptide set forth in SEQ ID NO:2. In another embodiment, a variant of an isolated polypeptide of the present invention differs, by at least 1, but less than 5, 10, 20, 50, or 100 amino acid residues from the sequence shown in SEQ ID NO:2. In another it differs from the corresponding sequence in SEQ ID NO:2 by at least one residue but less than 20%, 15%, 10% or 5% of the residues in it differ from the corresponding sequence in SEQ ID NO:2. If alignment is needed for this comparison the sequences should be aligned for maximum identity. "Looped" out sequences from deletions or insertions, or mismatches, are considered differences. Such variants retain the functional activity of the kinase proteins of the invention. Variants include polypeptides that differ in amino acid sequence due to natural allelic variation or mutagenesis.

Other variants can alter, eliminate or inhibit the biological activity (e.g., the protein kinase activity) of the polypeptide set forth in SEQ ID NO:2. For example, a variant of a 14171 polypeptide can have an amino acid other than K at position 51 or a variant can have an amino acid other than D at position 143 of SEQ ID NO:2 such that the resulting polypeptide does not have protein kinase activity.

The invention also provides kinase chimeric or fusion proteins. As used herein, a kinase "chimeric protein" or "fusion protein" comprises a kinase polypeptide operably linked to a non-kinase polypeptide. A "kinase polypeptide" refers to a polypeptide having an amino acid sequence corresponding to a kinase protein, whereas a "non-kinase polypeptide" refers to a polypeptide having an amino acid sequence corresponding to a protein that is not substantially identical to the kinase protein, e.g., a protein that is different from the kinase protein and which is derived from the same or a different organism. Within a kinase fusion protein, the kinase polypeptide can correspond to all or a portion of a kinase protein, preferably at least one biologically active portion of a kinase protein. Within the fusion protein, the term "operably linked" is intended to indicate that the kinase polypeptide and the non-kinase polypeptide are fused in-frame to each other. The non-kinase polypeptide can be fused to the N-terminus or C-terminus of the kinase polypeptide.

One useful fusion protein is a GST-kinase fusion protein in which the kinase sequences are fused to the C-terminus of the GST sequences. Such fusion proteins can facilitate the purification of recombinant kinase proteins. Another useful fusion protein is a V5-kinase fusion protein. Such a fusion protein can facilitate the identification of a 14171 polypeptide in a mixture of polypeptides.

In yet another embodiment, the fusion protein is a kinase-immunoglobulin fusion protein in which all or part of a kinase protein is fused to sequences derived from a member of the immunoglobulin protein family. The kinase-immunoglobulin fusion proteins of the invention can be incorporated into pharmaceutical compositions and administered to a subject to inhibit an interaction between a kinase ligand and a kinase protein on the surface of a cell, thereby suppressing kinase-mediated signal transduction in vivo. The kinase-immunoglobulin fusion proteins can be used to affect the bioavailability of a kinase cognate ligand. Inhibition of the kinase ligand/kinase interaction may be useful therapeutically, both for treating proliferative and differentiative disorders and for modulating (e.g., promoting or inhibiting) cell survival. Moreover, the kinase-immunoglobulin fusion proteins of the invention can be used as immunogens to produce anti-kinase antibodies in a subject, to purify kinase ligands, and in screening assays to identify molecules that inhibit the interaction of a kinase protein with a kinase ligand.

Preferably, a kinase chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, a kinase-encoding nucleic acid can be cloned into a commercially available expression vector such that it is linked in-frame to an existing fusion moiety. Variants of the kinase proteins can function as either kinase agonists (mimetics) or as kinase antagonists. Variants of the kinase protein can be generated by mutagenesis, e.g., discrete point mutation or truncation of the kinase protein. An agonist of the kinase protein can retain substantially the same or a subset of the biological activities of the naturally-occurring form of the kinase protein. An antagonist of the kinase protein can inhibit one or more of the activities of the naturally-occurring form of the kinase protein by, for example, competitively binding to a downstream or upstream member of a cellular signaling cascade that includes the kinase protein. Thus, specific biological effects can be elicited by treatment with a variant of limited function. Treatment of a subject with a variant having a subset of the biological activities of the naturally-occurring form of the protein can have fewer side effects in a subject relative to treatment with the naturally occurring form of the kinase proteins.

Variants of the kinase protein that function as either kinase agonists or as kinase antagonists can be identified by screening combinatorial libraries of mutants, e.g., truncation mutants, of the kinase protein for kinase protein agonist or antagonist activity. In one embodiment, a variegated library of kinase variants is generated by combinatorial mutagenesis at the nucleic acid level and is encoded by a variegated gene library. A variegated library of kinase variants can be produced by, for example, enzymatically ligating a mixture of synthetic oligonucleotides into gene sequences such that a degenerate set of potential kinase sequences is expressible as individual polypeptides, or alternatively, as a set of larger fusion proteins (e.g., for phage display) containing the set of kinase sequences therein. There are a variety of methods that can be used to produce libraries of potential kinase variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential kinase sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) Nucleic Acid Res. 11:477).

In addition, libraries of fragments of the kinase protein coding sequence can be used to generate a variegated population of kinase fragments for screening and subsequent selection of variants of a kinase protein. In one embodiment, a library of coding sequence fragments can be generated by treating a double-stranded PCR fragment of a kinase coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the kinase protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of kinase proteins. The most widely used techniques, which are amenable to high through-put analysis for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify kinase variants (Arkin and Yourvan (1992) *Proc. Natl. Acad. Sci. USA* 89:78117815; Delgrave et al. (1993) *Protein Engineering* 6(3):327-331).

Figure 2:
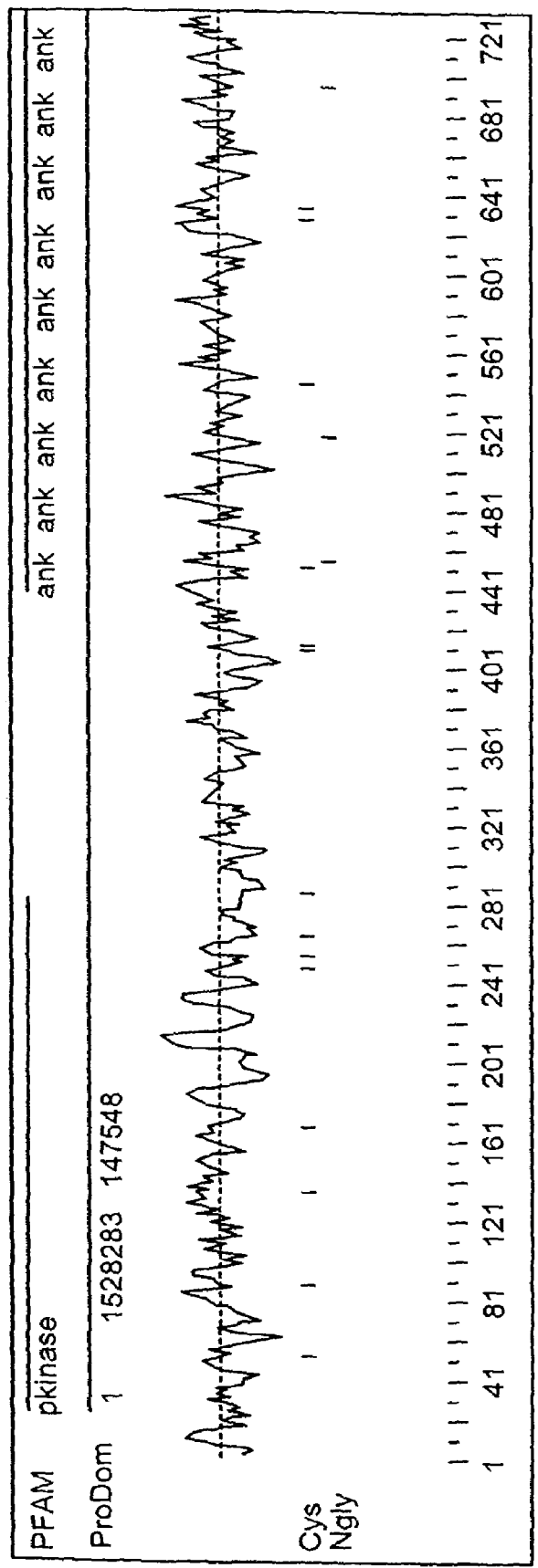
FIG. 2 shows a 14171 hydrophobicity plot. The plot shows that the 14171 protein kinase contains a kinase domain at the 5' end and 6 ankyrin repeats at the 3' end. Relative hydrophobic residues are shown above the dashed horizontal line, and relative hydrophilic residues are below the dashed horizontal line. The cysteine residues (cys) and N glycosylation sites (Ngly) are indicated by short vertical lines just below the hydropathy trace. The numbers corresponding to the amino acid sequence (shown in SEQ ID NO:2) of human 14171 protein kinase are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or an N-glycosylation site.

An isolated kinase polypeptide of the invention can be used as an immunogen to generate antibodies that bind kinase proteins using standard techniques for polyclonal and monoclonal antibody preparation. The full-length kinase protein can be used or, alternatively, the invention provides antigenic fragments of the kinase protein for use as immunogens. The immunogens can be produced by recombinant DNA techniques or synthesized chemically. The antigenic fragment of the kinase protein comprises at least 8, preferably 10, 15, 20, or 30 amino acid residues of the amino acid sequence shown in SEQ ID NO:2 and encompasses an epitope of the kinase protein such that an antibody raised against the antigenic fragment forms a specific immune complex with the kinase protein. Preferred epitopes encompassed by the antigenic peptide fragment are regions of a kinase protein that are located on the surface of the protein, e.g., hydrophilic regions (e.g., about amino acid residues 189 to 198, about residues 282 to 296, or about residues 348 to 361 of SEQ ID NO:2; see FIGS. 1 and 2). Embodiments of antigenic fragments can be antigenic peptides e.g., synthetic peptides having an amino acid sequence of SEQ ID NO:17, SEQ ID NO:18, or SEQ ID NO:19.

Accordingly, another aspect of the invention pertains to anti-kinase polyclonal and monoclonal antibodies that bind a kinase protein. Polyclonal anti-kinase antibodies can be prepared by immunizing a suitable subject (e.g., rabbit, goat, mouse, or other mammal) with a kinase immunogen. The anti-kinase antibody titer in the immunized subject can be monitored over time by standard techniques, such as with an enzyme linked immunosorbent assay (ELISA) using immobilized kinase protein. At an appropriate time after immunization, e.g., when the anti-kinase antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B-cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77-96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.,* 54:387-402).

Alternative to preparing monoclonal antibody-secreting hybridomas, a monoclonal anti-kinase antibody can be identified and isolated by screening a recombinant combinatorial immunoglobulin library (e.g., an antibody phage display library) with a kinase protein to thereby isolate immunoglobulin library members that bind the kinase protein. Kits for generating and screening phage display libraries are commercially available (e.g., the ZAP Express Phage Display Kit (Stratagene, La Jolla, Calif.)). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) Bio/Technology 9:1370-1372; Hay et al. (1992) *Hum. Antibod. Hybridomas* 3:81-85; Huse et al. (1989) *Science* 246:12751281; Griffiths et al. (1993) *EMBO J.* 12:725-734.

Additionally, recombinant anti-kinase antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86101533 and WO 87/02671; European Patent Application Nos. 184,187, 171, 496, 125,023, and 173,494; U.S. Pat. Nos. 4,816,567 and 5,225,539; European Patent Application 125,023; Better et al. (1988) Science 240:1041-1043; Liu et al. (1987) Proc. Natl. Acad. Sci. USA 84:3439-3443; Liu et al. (1987) J. Immunol. 139:35213526; Sun et al. (1987) Proc. Natl. Acad. Sci. USA 84:214-218; Nishimura et al. (1987) Canc. Res. 47:999-1005; Wood et al. (1985) Nature 314:446-449; Shaw et al. (1988) J. Natl. Cancer Inst. 80:1553-1559); Morrison (1985) Science 229:1202-1207; Oi et al. (1986) Bio/Techniques 4:214; Jones et al. (1986) Nature 321:552-525; Verhoeyan et al. (1988) Science 239:1534; and Beidler et al. (1988) J. Immunol. 141:4053-4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) Int. Rev. Immunol. 13:65-93); and U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) Bio/Technology 12:899-903).

An anti-kinase antibody (e.g., monoclonal antibody) can be used to isolate kinase proteins by standard techniques, such as affinity chromatography or immunoprecipitation. An anti-kinase antibody can facilitate the purification of natural kinase protein from cells and of recombinantly produced kinase protein expressed in host cells. Moreover, an anti-kinase antibody can be used to detect kinase protein (e.g., in a cellular lysate or cell supernatant) in order to evaluate the abundance and pattern of expression of the kinase protein. Anti-kinase antibodies can be used diagnostically to monitor protein levels in tissue as part of a clinical testing procedure to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^3$H.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium. The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha.-interferon, beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84:Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982). Alternatively, an antibody can be conjugated to a second antibody to form an antibody heteroconjugate as described by Segal in U.S. Pat. No. 4,676,980.

Recombinant Expression Vectors and Host Cells

Another aspect of the invention pertains to vectors, preferably expression vectors, containing a nucleic acid encoding a kinase protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g.; nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication-defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or polypeptides, including fusion proteins or polypeptides, encoded by nucleic acids as described herein (e.g., kinase proteins, mutant forms of kinase proteins, fusion proteins, etc.). It is further recognized that the nucleic acid sequences of the invention can be altered to contain codons, which are preferred, or non-preferred, for a particular expression system. For example, the nucleic acid can be one in which at least one altered codon, and preferably at least 10%, or 20% of the codons have been altered such that the sequence is optimized for expression in *E. coli*, yeast, human, insect or CHO cells. Methods for determining codon usage are well known in the art.

The recombinant expression vectors of the invention can be designed for expression of kinase protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31-40), pMAL (New England Biolabs, Beverly, Mass.), and pRIT5 (Pharmacia, Piscataway, N.J.) which fuse glutathione Stransferase (GST), maltose E binding protein, or protein A, respectively, to the target recombinant protein. Examples of suitable inducible nonfusion *E. coli* expression vectors include pTrc (Amann et al. (1988) *Gene* 69:301-315) and pET 1d (Studier et al. (1990) in *Gene Expression Technology: Methods in Enzymology* 185 (Academic Press, San Diego, Calif.), pp. 60-89). Strategies to maximize recombinant protein expression in *E. coli* can be found in Gottesman (1990) in *Gene Expression Technology: Methods in Enzymology* 185 (Academic Press, CA), pp. 119-128 and Wada et al. (1992) *Nucleic Acids Res.* 20:2111-2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39)); yeast cells (examples of vectors for expression in yeast *S. cerevisiae* include pYepSec1 (Baldari et al. (1987) *EMBO J.* 6:229-234), pMFa (Kurjan and Herskowitz (1982) *Cell* 30:933-943), pJRY88 (Schultz et al. (1987) *Gene* 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular Cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein. A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), particular promoters of T-cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873, 316 and European Application Patent Publication No. 264, 166). Developmentally-regulated promoters are also encompassed, for example the murine hox promoters (Kessel and Gruss (1990) *Science* 249:374-379), the α-fetoprotein promoter (Campes and Tilghman (1989) *Genes Dev.* 3:537-546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to kinase mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics*, Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboratory Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding a kinase protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) kinase protein. Accordingly, the invention further provides methods for producing kinase protein using the host cells of the invention. In one embodiment, the method comprises culturing the host cell of the invention, into which a recombinant expression vector encoding a kinase protein has been introduced, in a suitable medium such that kinase protein is produced. In another embodiment, the method further comprises isolating kinase protein from the medium or the host cell.

The host cells of the invention can also be used to produce nonhuman transgenic animals. For example, in one embodiment, a host cell of the invention is a fertilized oocyte or an embryonic stem cell into which a kinase-coding sequence has been introduced. Such host cells can then be used to create nonhuman transgenic animals in which exogenous kinase sequences have been introduced into their genome or homologous recombinant animals in which endogenous kinase sequences have been altered. Such animals are useful for studying the function and/or activity of kinase genes and proteins and for identifying and/or evaluating modulators of kinase activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous kinase gene has been altered by homologous recombination between the endogenous gene and an exogenous DNA molecule introduced into a cell of the animal, e.g., an embryonic cell of the animal, prior to development of the animal.

A transgenic animal of the invention can be created by introducing kinaseencoding nucleic acid into the male pronuclei of a fertilized oocyte, e.g., by microinjection, retroviral infection, and allowing the oocyte to develop in a pseudopregnant female foster animal. The kinase cDNA sequence can be introduced as a transgene into the genome of a nonhuman animal. Alternatively, a homolog of the kinase gene can be isolated based on hybridization and used as a transgene. Intronic sequences and polyadenylation signals can also be included in the transgene to increase the efficiency of expression of the transgene. A tissue-specific regulatory sequence(s) can be operably linked to the kinase transgene to direct expression of kinase protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the kinase transgene in its genome and/or expression of kinase mRNA in tissues or cells of the animals. A transgenic founder animal can then be used to breed additional animals carrying the transgene. Moreover, transgenic animals carrying a transgene encoding kinase gene can further be bred to other transgenic animals carrying other transgenes.

To create a homologous recombinant animal, one prepares a vector containing at least a portion of a kinase gene or a homolog of the gene into which a deletion, addition, or substitution has been introduced to thereby alter, e.g., functionally disrupt, the kinase gene. In a preferred embodiment, the vector is designed such that, upon homologous recombination, the endogenous kinase gene is functionally disrupted (i.e., no longer encodes a functional protein; such vectors are also referred to as "knock out" vectors). Alternatively, the vector can be designed such that, upon homologous recombination, the endogenous kinase gene is mutated or otherwise altered but still encodes functional protein (e.g., the upstream regulatory region can be altered to thereby alter the expression of the endogenous kinase protein). In the homologous recombination vector, the altered portion of the kinase gene is flanked at its 5′ and 3′ ends by additional nucleic acid of the kinase gene to allow for homologous recombination to occur between the exogenous kinase gene carried by the vector and an endogenous kinase gene in an embryonic stem cell. The additional flanking kinase nucleic acid is of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation), and cells in which the introduced kinase gene has homologously recombined with the endogenous kinase gene are selected (see, e.g., Li et al. (1992) Cell 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford), pp. 113-152). A chimeric embryo can then be implanted into a suitable pseudopregnant female foster animal and the embryo brought to term. Progeny harboring the homologously-recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823-829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810-813 and PCT Publication Nos. WO 97/07668 and WO 97/07669.

Pharmaceutical Compositions

The kinase nucleic acid molecules, kinase proteins, and anti-kinase antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides (e.g., siRNAs), polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, CREMOPHOR EL (emulsifying agent, BASF; Mount Olive, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., a kinase protein, anti-kinase antibody or siRNA) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds (e.g. a composition including an siRNA and a delivery reagent (e.g., a transfection reagent)) are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1µ/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Uses and Methods of the Invention

The nucleic acid molecules, proteins, protein homologs, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express kinase protein (e.g., via a recombinant expression vector in a host cell in gene therapy applications), to detect kinase mRNA (e.g., in a biological sample) or a genetic lesion in a kinase gene, and to modulate kinase activity, as described further below. The 14171 proteins can be used to treat disorders characterized by insufficient or excessive production of a 14171 substrate or production of 14171 inhibitors. In addition, the kinase proteins can be used to screen for naturally occurring 14171 substrates, to screen drugs or compounds that modulate cellular growth and/or metabolism as well as to treat disorders characterized by insufficient or excessive production of kinase protein or production of kinase protein forms that have decreased, aberrant or unwanted activity compared to kinase wild type protein (e.g., protein kinase activity). In addition, the anti-kinase antibodies of the invention can be used to detect and isolate kinase proteins and modulate kinase activity.

A method of evaluating a compound for the ability to interact with, e.g., bind, a subject 14171 polypeptide is provided. The method includes: contacting the compound with the subject 14171 polypeptide; and evaluating ability of the compound to interact with, e.g., to bind or form a complex with the subject 14171 polypeptide. This method can be performed in vitro, e.g., in a cell free system, or in vivo, e.g., in a two-hybrid interaction trap assay. This method can be used to identify naturally occurring molecules which interact with subject 14171 polypeptide. It can also be used to find natural or synthetic inhibitors of subject 14171 polypeptide. Screening methods are discussed in more detail below.

Screening Assays

The invention provides a method (also referred to herein as a "screening assay") for identifying modulators, i.e., candidate or test compounds or agents (e.g., proteins, peptides, peptidomimetics, peptoids, small molecules, or other drugs) that bind to kinase proteins or have a stimulatory or inhibitory effect on, for example, kinase expression or kinase activity, or have a stimulatory or inhibitory effect on, for example, the expression or activity of a 14171 substrate. Compounds thus identified can be used to modulate the activity of target gene products (e.g., 14171 genes) in a therapeutic protocol, to elaborate the biological function of the target gene product, or to identify compounds that disrupt normal target gene interactions.

In one embodiment, the invention provides assays for screening candidate or test compounds which are substrates of a 14171 protein or polypeptide or a biologically active portion thereof. In another embodiment, the invention provides assays for screening candidate or test compounds which bind to or modulate the activity of a 14171 protein or polypeptide or a biologically active portion thereof.

The test compounds of the present invention can be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. Nos. 5,571,698; 5,403,484; and 5,223, 409), plasmids (Cull et al. (1992) *Proc. Natl. Acad. Sci. USA* 89:1865-1869), or phage (Scott and Smith (1990) *Science*

249:386-390; Devlin (1990) *Science* 249:404-406; Cwirla et al. (1990) *Proc. Natl. Acad. Sci. USA* 87:6378-6382; and Felici (1991) *J. Mol. Biol.* 222:301-310).

Determining the ability of the test compound to bind to the kinase protein can be accomplished, for example, by coupling the test compound with a radioisotope or enzymatic label such that binding of the test compound to the kinase protein or biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the kinase protein to bind to or interact with a kinase target molecule. By "target molecule" is intended a molecule with which a kinase protein binds or interacts in nature. In one embodiment, a target molecule can be identified through a two-hybrid assay in yeast. In a preferred embodiment, the ability of the kinase protein to bind to or interact with a kinase target molecule can be determined by monitoring the activity of the target molecule. For example, the activity of the target molecule can be monitored by detecting induction of a cellular second messenger of the target (e.g., intracellular Ca$^{2+}$, diacylglycerol, IP3, etc.), detecting catalytic/enzymatic activity of the target on an appropriate substrate, detecting the induction of a reporter gene (e.g., a kinase-responsive regulatory element operably linked to a nucleic acid encoding a detectable marker, e.g., luciferase), for example, detecting the activity of NF-κB in a reporter gene assay, or detecting a cellular response, for example, cellular differentiation, cell proliferation, apoptosis, or programmed cell death. Biochemical events, substrates, and effector molecules, include, but are not limited to, those discussed above with reference to the functions described above, ankyrin related functions, and RIP, RIPlike, and CARDIAK-like functions.

In yet another embodiment, an assay of the present invention is a cell-free assay comprising contacting a kinase protein or biologically active portion thereof, e.g., a domain (e.g., a protein kinase domain from about amino acids 22 to 279 of SEQ ID NO:2, or a portion of 14171 protein kinase comprising the protein kinase domain, e.g., residues 1 to 350 or 1-450 of SEQ ID NO:2) alone or fused with heterologous sequences, e.g., 25, 50, 75, 100 or more amino acids from a non-14171 polypeptide) with a test compound and determining the ability of the test compound to bind to the kinase protein or biologically active portion thereof. Binding of the test compound to the kinase protein can be determined either directly or indirectly as described above. In a preferred embodiment, the assay includes contacting the kinase protein or biologically active portion thereof with a known compound that binds kinase protein to form an assay mixture, contacting the assay mixture with a test compound, and determining the ability of the test compound to preferentially bind to kinase protein or biologically active portion thereof as compared to the known compound.

In another embodiment, an assay is a cell-free assay comprising contacting kinase protein or biologically active portion thereof, e.g., a domain (e.g., a protein kinase domain from about amino acids 22 to 279 of SEQ ID NO:2, alone or fused with heterologous sequences, e.g., 6, 25, 50, 75, 100 or more amino acids from a non-14171 polypeptide) with a test compound and determining the ability of the test compound to modulate (e.g., stimulate or inhibit) the activity of the kinase protein or biologically active portion thereof. Determining the ability of the test compound to modulate the activity of a kinase protein can be accomplished, for example, by determining the ability of the kinase protein to bind to a kinase target molecule as described above for determining direct binding. In an alternative embodiment, determining the ability of the test compound to modulate the activity of a kinase protein can be accomplished by determining the ability of the kinase protein to further modulate, e.g., phosphorylate, a kinase target molecule. For example, the catalytic/enzymatic activity of the target molecule on an appropriate substrate, e.g., a protein or a peptide containing a residue capable of being phosphorylated, e.g., a serine or threonine (e.g., a threonine in a T-P motif), can be determined as previously described.

In yet another embodiment, the cell-free assay comprises contacting the kinase protein or biologically active portion thereof with a known compound that binds a kinase protein to form an assay mixture, contacting the assay mixture with a test compound, and determining the ability of the test compound to preferentially bind to or modulate the activity of a kinase target molecule.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 14171 protein to bind to a target molecule can be accomplished using real-time Biomolecular Interaction Analysis (BIA) (see, e.g., Sjolander and Urbaniczky (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

In the above-mentioned assays, it may be desirable to immobilize either a kinase protein or its target molecule to facilitate separation of complexed from uncomplexed forms of one or both of the proteins, as well as to accommodate automation of the assay. In one embodiment, a fusion protein can be provided that adds a domain, e.g., GST, as described below or the Fc region of immunoglobulins, which can bind to protein A or protein G; amino acid residues, e.g., two, three, four, five, preferably six histidine residues; or a cofactor, e.g., biotin; that allow one or both of the proteins to be bound to a matrix. For example, glutathione-S-transferase/kinase (GST) fusion proteins or glutathione-Stransferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or kinase protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of kinase binding or activity determined using standard techniques.

Other techniques for immobilizing proteins on matrices can also be used in the screening assays of the invention. For example, either kinase protein or its target molecule can be immobilized utilizing conjugation of biotin and streptavidin. Biotinylated kinase molecules or target molecules can be prepared from biotin-N-HS (N-hydroxysuccinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with a kinase protein or target molecules but which do not interfere with binding of the kinase protein to its target molecule can be derivatized to the wells of the plate, and unbound target or kinase protein trapped in the wells by antibody conjugation. Methods for detecting such complexes, in addition to those described above for the GST-immobilized complexes, include immunodetection of complexes using antibodies reactive with the kinase protein or target molecule, as well as enzyme-linked assays that rely on detecting an enzymatic activity associated with the kinase protein or target molecule.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific or selective for the immobilized component (the antibody, in turn, can be directly labeled or indirectly labeled with, e.g., a labeled anti-Ig antibody).

In one embodiment, this assay is performed utilizing antibodies reactive with 14171 protein or target molecules but which do not interfere with binding of the 14171 protein to its target molecule. Such antibodies can be derivatized to the wells of the plate, and unbound target or 14171 protein trapped in the wells by antibody conjugation. Methods for detecting such complexes, in addition to those described above for the GST-immobilized complexes, include immunodetection of complexes using antibodies reactive with the 14171 protein or target molecule, as well as enzyme-linked assays which rely on detecting an enzymatic activity associated with the 14171 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas and Minton (1993) *Trends Biochem Sci* 18:284-7); chromatography (gel filtration chromatography, ion-exchange chromatography); electrophoresis (see, e.g., Ausubel et al., eds. (1999) *Current Protocols in Molecular Biology*, J. Wiley, New York.); and immunoprecipitation (see, for example, Ausubel et al., eds. (1999) *Current Protocols in Molecular Biology*, J. Wiley, New York). Such resins and chromatographic techniques are known to one skilled in the art (see, e.g., Heegaard (1998) *J Mol Recognit* 11:141-8; Hage and Tweed (1997) *J Chromatogr B Biomed Sci Appl.* 699:499-525). Further, fluorescence energy transfer can also be conveniently utilized, as described herein, to detect binding without further purification of the complex from solution.

In a preferred embodiment, the assay includes contacting the 14171 protein or biologically active portion thereof with a known compound which binds 14171 to form an assay mixture, contacting the assay mixture with a test compound, and determining the ability of the test compound to interact with a 14171 protein, wherein determining the ability of the test compound to interact with a 14171 protein includes determining the ability of the test compound to preferentially bind to 14171 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 14171 genes herein identified. In an alternative embodiment, the invention provides methods for determining the ability of the test compound to modulate the activity of a 14171 protein through modulation of the activity of a downstream effector of a 14171 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific or selective for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is prelabeled, the detection of label immobilized on the surface indicates that complexes were formed. Where the non-immobilized species is not pre-labeled, an indirect label can be used to detect complexes anchored on the surface; e.g., using a labeled antibody specific or selective for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific or selective for one of the binding components to anchor any complexes formed in solution, and a labeled antibody specific or selective for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In another embodiment, modulators of kinase expression are identified in a method in which a cell is contacted with a candidate compound and the expression of kinase mRNA or protein in the cell is determined relative to expression of kinase mRNA or protein in a cell in the absence of the candidate compound. When expression is greater (statistically significantly greater) in the presence of the candidate compound than in its absence, the candidate compound is identified as a stimulator of kinase mRNA or protein expression. Alternatively, when expression is less (statistically significantly less) in the presence of the candidate compound than in its absence, the candidate compound is identified as an inhibitor of kinase mRNA or protein expression. The level of kinase mRNA or protein expression in the cells can be determined by methods described herein for detecting kinase mRNA or protein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Bio/Techniques* 14:920-924; Iwabuchi et al. (1993) *Oncogene* 8:1693-1696; and PCT Publication No. WO 94/10300), to identify other proteins, which bind to or interact with kinase protein ("kinase-binding proteins" or "kinase-bp") and modulate kinase activity. Such kinase-binding proteins are also likely to be involved in the propagation of signals by the kinase proteins as, for example, upstream or downstream elements of a signaling pathway.

The two-hybrid system is based on the modular nature of most transcription factors, which consist of separable DNA-binding and activation domains. Briefly, the assay utilizes two different DNA constructs. In one construct, the gene that codes for a 14171 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 14171 protein can be the fused to the activator domain.) If the "bait" and the "prey" proteins are able to interact, in vivo, forming a 14171-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 14171 protein.

In another aspect, the invention pertains to a combination of two or more of the assays described herein. For example, a modulating agent can be identified using a cell-based or a cell free assay, and the ability of the agent to modulate the activity of a 14171 protein can be confirmed in vivo, e.g., in an animal such as an animal model for aberrant or deficient kinase function or expression This invention further pertains to novel agents identified by the above-described screening assays Accordingly, it is within the scope of this invention to further use an agent identified as described herein (e.g., a 14171 modulating agent, an antisense 14171 nucleic acid molecule, a 14171-specific antibody, or a 14171-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

Chromosome Mapping

The isolated complete or partial kinase gene sequences of the invention can be used to map their respective kinase genes on a chromosome, thereby facilitating the location of gene regions associated with genetic disease. Computer analysis of kinase sequences can be used to rapidly select PCR primers (preferably 15-25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the kinase sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919-924). Somatic cell hybrids containing only fragments of human chromosomes can also be produced by using human chromosomes with translocations and deletions.

Other mapping strategies that can similarly be used to map a kinase sequence to its chromosome include in situ hybridization (described in Fan et al. (1990) *Proc. Natl. Acad. Sci. USA* 87:6223-27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma et al. (1988) *Human Chromosomes: A Manual of Basic Techniques* (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783-787.

Moreover, differences in the DNA sequences between individuals affected and unaffected with a disease associated with the kinase gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The kinase sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described in U.S. Pat. No. 5,272,057).

Furthermore, the sequences of the present invention can be used to provide an alternative technique for determining the actual base-by-base DNA sequence of selected portions of an individual's genome. Thus, the kinase sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The kinase sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequence of SEQ ID NO:1 can comfortably provide positive individual identification with a panel of perhaps 10 to 1,000 primers that each yield a noncoding amplified sequence of 100 bases. If predicted coding sequences, such as in SEQ ID NO:1 are used, a more appropriate number of primers for positive individual identification would be 500 to 2,000.

Use of Partial Kinase Sequences in Forensic Biology

DNA-based identification techniques can also be used in forensic biology. In this manner, PCR technology can be used to amplify DNA sequences taken from very small biological samples such as tissues, e.g., hair, skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to the noncoding region of SEQ ID NO:1 are particularly appropriate for this use as greater numbers of polymorphisms occur in the noncoding region, making it easier to differentiate individuals using this technique. Examples of polynucleotide reagents include the kinase sequence or portions thereof, e.g., fragments derived from the noncoding region of SEQ ID NO:1 having a length of at least 20 or 30 bases.

The kinase sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such kinase probes, can be used to identify tissue by species and/or by organ type.

In a similar fashion, these reagents, e.g., kinase primers or probes can be used to screen tissue culture for contamination (i.e., screen for the presence of a mixture of different types of cells in a culture).

Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

Diagnostic Assays

One aspect of the present invention relates to diagnostic assays for detecting kinase protein and/or nucleic acid expression as well as kinase activity, in the context of a biological sample. An exemplary method for detecting the presence or absence of kinase proteins in a biological sample involves obtaining a biological sample from a test subject and contacting the biological sample with a compound or an agent capable of detecting kinase protein or nucleic acid (e.g., mRNA, genomic DNA) that encodes kinase protein such that the presence of kinase protein is detected in the biological sample. Results obtained with a biological sample from the test subject may be compared to results obtained with a biological sample from a control subject.

"Misexpression or aberrant expression", as used herein, refers to a non-wild type pattern of gene expression, at the RNA or protein level. It includes: expression at nonwild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, posttransitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

A preferred agent for detecting kinase mRNA or genomic DNA is a labeled nucleic acid probe capable of hybridizing to kinase mRNA or genomic DNA. The nucleic acid probe can be, for example, a full-length or partial kinase nucleic acid, such as the nucleic acid of SEQ ID NO:1, or a portion thereof, such as a nucleic acid molecule of at least 15, 30, 50, 100, 250, or 500 nucleotides in length and sufficient to specifically hybridize under stringent conditions to kinase mRNA or genomic DNA. Other suitable probes for use in the diagnostic assays of the invention are described herein.

A preferred agent for detecting kinase protein is an antibody capable of binding to kinase protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect kinase mRNA, protein, or genomic DNA in a biological sample in vitro as well as in vivo. For example, in vitro techniques for detection of kinase mRNA include Northern hybridizations and in situ hybridizations. In vitro techniques for detection of kinase protein include enzyme linked immunosorbent assays (ELISAs), Western blots, immunoprecipitations, and immunofluorescence. In vitro techniques for detection of kinase genomic DNA include Southern hybridizations. Furthermore, in vivo techniques for detection of kinase protein include introducing into a subject a labeled anti-kinase antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. Biological samples may be obtained from blood, serum, cells, or tissue of a subject.

The invention also encompasses kits for detecting the presence of kinase proteins in a biological sample (a test sample). Such kits can be used to determine if a subject is suffering from or is at increased risk of developing a disorder associated with aberrant expression of kinase protein. For example, the kit can comprise a labeled compound or agent capable of detecting kinase protein or mRNA in a biological sample and means for determining the amount of a kinase protein in the sample (e.g., an anti-kinase antibody or an oligonucleotide probe that binds to DNA encoding the kinase protein, e.g., SEQ ID NO:2). Kits can also include instructions for observing that the tested subject is suffering from or is at risk of developing a disorder associated with aberrant expression of kinase sequences if the amount of kinase protein or mRNA is above or below a normal level.

For antibody-based kits, the kit can comprise, for example: (1) a first antibody (e.g., attached to a solid support) that binds to kinase protein; and, optionally, (2) a second, different antibody that binds to kinase protein or the first antibody and is conjugated to a detectable agent. For oligonucleotide-based kits, the kit can comprise, for example: (1) an oligonucleotide, e.g., a detectably labeled oligonucleotide, that hybridizes to a kinase nucleic acid sequence or (2) a pair of primers useful for amplifying a kinase nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of kinase proteins.

Prognostic Assays

The methods described herein can furthermore be utilized as diagnostic or prognostic assays to identify subjects having or at risk of developing a disease or disorder associated with kinase protein, kinase nucleic acid expression, or kinase activity. Prognostic assays can be used for prognostic or predictive purposes to thereby prophylactically treat an individual prior to the onset of a disorder characterized by or associated with kinase protein, kinase nucleic acid expression, or kinase activity.

Thus, the present invention provides a method in which a test sample is obtained from a subject, and kinase protein or nucleic acid (e.g., mRNA, genomic DNA) is detected, wherein the presence of kinase protein or nucleic acid is diagnostic for a subject having or at risk of developing a disease or disorder associated with aberrant kinase expression or activity. As used herein, a "test sample" refers to a biological sample obtained from a subject of interest. For example, a test sample can be a biological fluid cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease kinase activity) to effectively treat a disease or disorder associated with aberrant kinase expression or activity. In this manner, a test sample is obtained and kinase protein or nucleic acid is detected. The presence of kinase protein or nucleic acid is diagnostic for a subject that can be administered the agent to treat a disorder associated with aberrant kinase expression or activity.

The methods of the invention can also be used to detect genetic lesions or mutations in a kinase gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion or mutation characterized by at least one of an alteration affecting the integrity of a gene encoding a kinase-protein, or the misexpression of the kinase gene. For example, such genetic lesions or mutations can be detected by ascertaining the existence of at least one of: (1) a deletion of one or more nucleotides from a kinase gene; (2) an addition of one or more nucleotides to a kinase gene; (3) a substitution of one or more nucleotides of a kinase gene; (4) a chromosomal rearrangement of a kinase gene; (5) an alteration in the level of a messenger RNA transcript of a kinase gene; (6) an aberrant modification of a kinase gene, such as of the methylation pattern of the genomic DNA; (7) the presence of a non-wild-type splicing pattern of a messenger RNA transcript of a kinase gene; (8) a non-wild-type level of a kinase-protein; (9) an allelic loss of a kinase gene; and (10) an inappropriate post-translational modification of a kinase-protein. As described herein, there are a large number of assay techniques known in the art that can be used for detecting lesions in a kinase gene. Any cell type or tissue in which kinase proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the kinase-gene (see, e.g., Abravaya et al. (1995) *Nucleic Acids Res.* 23:675-682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a kinase gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in a kinase molecule can be identified by hybridizing a sample and control nucleic acids, e.g., DNA or RNA, to high density arrays containing hundreds or thousands of oligonucleotides probes (Cronin et al. (1996) *Human Mutation* 7:244-255; Kozal et al. (1996) *Nature Medicine* 2:753-759). In yet another embodiment, any of a variety of sequencing reactions known in the art can be used to directly sequence the kinase gene and detect mutations by comparing the sequence of the sample kinase gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the kinase gene include methods in which protection from cleavage agents is used to detect mismatched bases in RNA/RNA or RNA/DNA heteroduplexes (Myers et al. (1985) *Science* 230: 1242). See, also Cotton et al. (1988) *Proc. Natl. Acad. Sci. USA* 85:4397; Saleeba et al. (1992) *Methods Enzymol.* 217:286-295. In a preferred embodiment, the control DNA or RNA can be labeled for detection.

In still another embodiment, the mismatch cleavage reaction employs one or more "DNA mismatch repair" enzymes that recognize mismatched base pairs in doublestranded DNA in defined systems for detecting and mapping point mutations in kinase cDNAs obtained from samples of cells. See, e.g., Hsu et al. (1994) *Carcinogenesis* 15:1657-1662. According to an exemplary embodiment, a probe based on a kinase sequence, e.g., a wild-type kinase sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in kinase genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125-144; Hayashi (1992) *Genet. Anal. Tech. Appl.* 9:73-79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437-2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnose patients exhibiting symptoms or family history of a disease or illness involving a kinase gene.

Pharmacogenomics

Agents or modulators that have a stimulatory or inhibitory effect on kinase activity (e.g., kinase gene expression) as identified by a screening assay described herein, can be administered to individuals to treat (prophylactically or therapeutically) disorders associated with aberrant kinase activity as well as to modulate the cellular growth, differentiation and/or metabolism. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of kinase protein, expression of kinase nucleic acid, or mutation content of kinase genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254-266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of kinase protein, expression of kinase nucleic acid, or mutation content of kinase genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a kinase modulator, such as a modulator identified by one of the exemplary screening assays described herein.

Monitoring of Effects During Clinical Trials

Monitoring the influence of agents (e.g., drugs, compounds) on the expression or activity of kinase genes (e.g., the ability to modulate aberrant cell proliferation and/or differentiation) can be applied not only in basic drug screening but also in clinical trials. For example, the effectiveness of an agent, as determined by a screening assay as described herein, to increase or decrease kinase gene expression, protein levels, or protein activity, can be monitored in clinical trials of subjects exhibiting decreased or increased kinase gene expression, protein levels, or protein activity. In such clinical trials, kinase expression or activity and preferably that of other genes that have been implicated in for example, a cellular proliferation disorder, can be used as a marker of cellular growth and differentiation.

For example, and not by way of limitation, genes that are modulated in cells by treatment with an agent (e.g., compound, drug, or small molecule) that modulates kinase activity (e.g., as identified in a screening assay described herein) can be identified. Thus, to study the effect of agents on cellular proliferation disorders, for example, in a clinical trial, cells can be isolated and RNA prepared and analyzed for the levels of expression of kinase genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of kinase genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of a kinase protein, mRNA, or genomic DNA in the preadministration sample; (3) obtaining one or more postadministration samples from the subject; (4) detecting the level of expression or activity of the kinase protein, mRNA, or genomic DNA in the postadministration samples; (5) comparing the level of expression or activity of the kinase protein, mRNA, or genomic DNA in the preadministration sample with the kinase protein, mRNA, or genomic DNA in the postadministration sample or samples; and (vi) altering the administration of the agent to the subject accordingly to bring about the desired effect, i.e., for example, an increase or a decrease in the expression or activity of a kinase protein.

Methods of Treatment

The present invention provides for both prophylactic and therapeutic methods of treating a subject at risk of (or susceptible to) a disorder or having a disorder associated with aberrant kinase expression or activity. Additionally, the compositions of the invention find use in the treatment of disorders described herein, especially viral infections. Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. "Subject," as used herein, can refer to a mammal, e.g., a human, or to an experimental or animal or disease model. The subject can also be a non-human animal, e.g., a horse, cow, goat, or other domestic animal. A therapeutic agent includes, but is not limited to, small molecules, peptides, antibodies, ribozymes, antisense oligonucleotides and siRNAs.

With regard to both prophylactic and therapeutic methods of treatment, such treatments can be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 14171 molecules of the present invention or 14171 modulators according to that individual's drug response genotype. Pharmacogenomics allows a clinician or physician to target prophylactic or therapeutic treatments to patients who will most benefit from the treatment and not to provide this treatment to patients who will experience toxic drug-related side effects.

Prophylactic Methods

In one aspect, the invention provides a method for preventing in a subject a disease or condition associated with an aberrant kinase expression or activity by administering to the subject an agent that modulates kinase expression or at least one kinase gene activity. Subjects at risk for a disease that is caused, or contributed to, by aberrant kinase expression or activity can be identified by, for example, any or a combination of diagnostic or prognostic assays as described herein. Administration of a prophylactic agent can occur prior to the manifestation of symptoms characteristic of the kinase aberrancy, such that a disease or disorder is prevented or, alternatively, delayed in its progression. Depending on the type of kinase aberrancy, for example, a kinase agonist or kinase antagonist agent can be used for treating the subject. The appropriate agent can be determined based on screening assays described herein.

Therapeutic Methods

Another aspect of the invention pertains to methods of modulating kinase expression or activity for therapeutic purposes. The modulatory method of the invention involves contacting a cell with an agent that modulates one or more of the activities of kinase protein activity associated with the cell. An agent that modulates kinase protein activity can be an agent as described herein, such as a nucleic acid or a protein, a naturally-occurring cognate ligand of a kinase protein, a peptide, a kinase peptidomimetic, or other small molecule. In one embodiment, the agent stimulates one or more of the biological activities of kinase protein. Examples of such stimulatory agents include active kinase protein and a nucleic acid molecule encoding a kinase protein that has been introduced into the cell. In another embodiment, the agent inhibits one or more of the biological activities of kinase protein. Examples of such inhibitory agents include agents which target the expression or activity of nucleic acids encoding 14171 protein kinase, e.g., antisense kinase nucleic acid molecules, anti-kinase antibodies and siRNAs.

These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a kinase protein or nucleic acid molecule. In one embodiment, the method involves administering an agent (e.g., an agent identified by a screening assay described herein), or a combination of agents, that modulates (e.g., upregulates or downregulates) kinase expression or activity. In another embodiment, the method involves administering a kinase protein or nucleic acid molecule as therapy to compensate for reduced or aberrant kinase expression or activity.

Stimulation of kinase activity is desirable in situations in which a kinase protein is abnormally downregulated and/or in which increased kinase activity is likely to have a beneficial effect. Conversely, inhibition of kinase activity is desirable in situations in which kinase activity is abnormally upregulated and/or in which decreased kinase activity is likely to have a beneficial effect.

The 14171 molecules can act as novel diagnostic targets and therapeutic agents for controlling one or more of a cell growth or differentiation disorder, an apoptotic disorder, a viral disorder, an inflammatory disorder, a kidney disorder, or a prostate disorder, all of which are described above.

As discussed, successful treatment of 14171 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 14171 disorders. Such molecules can include, but are not limited to peptides, phosphopeptides, small organic or inorganic molecules, or antibodies (including, for example, polyclonal, monoclonal, humanized, human, antiidiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules can be utilized in treating or preventing a disease characterized by 14171 expression is through the use of aptamer molecules specific for 14171 protein. Aptamers are nucleic acid molecules having a tertiary structure which permits them to specifically or selectively bind to protein ligands (see, e.g., Osborne et al. (1997) *Curr. Opin. Chem Biol.* 1:5-9; and Patel (1997) *Curr Opin Chem Biol* 1:32-46). Since nucleic acid molecules can in many cases be more conveniently introduced into target cells than therapeutic protein molecules can be, aptamers offer a method by which 14171 protein activity can be specifically decreased without the introduction of drugs or other molecules which can have pluripotent effects.

Antibodies can be generated that are both specific for target gene product and that reduce target gene product activity. Such antibodies can, therefore, by administered in instances whereby negative modulatory techniques are appropriate for the treatment of 14171 disorders. For a description of antibodies, see the Antibody section above.

In circumstances wherein injection of an animal or a human subject with a 14171 protein or epitope for stimulating antibody production is harmful to the subject, it is possible to generate an immune response against 14171 through the use of anti-idiotypic antibodies (see, for example, Herlyn (1999) *Ann Med* 31:66-78; and Bhattacharya-Chatterjee and Foon (1998) *Cancer Treat Res.* 94:51-68). If an anti-idiotypic antibody is introduced into a mammal or human subject, it should stimulate the production of anti-anti-idiotypic antibodies, which should be specific to the 14171 protein. Vaccines directed to a disease characterized by 14171 expression can also be generated in this fashion.

In instances where the target antigen is intracellular and whole antibodies are used, internalizing antibodies can be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889-7893).

The identified compounds that inhibit target gene expression, synthesis and/or activity can be administered to a patient at therapeutically effective doses to prevent, treat or ameliorate 14171 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays can utilize antibody mimics and/or "biosensors" that have been created through molecular imprinting techniques. The compound which is able to modulate 14171 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell et al (1996) *Current Opinion in Biotechnology* 7:89-94 and in Shea (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis et al (1993) *Nature* 361:645-647. Through the use of isotope-labeling, the "free" concentration of compound which modulates the expression or activity of 14171 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz et al (1995) *Analytical Chemistry* 67:2142-2144.

Another aspect of the invention pertains to methods of modulating 14171 expression or activity for therapeutic purposes. Accordingly, in an exemplary embodiment, the modulatory method of the invention involves contacting a cell with a 14171 or agent that modulates one or more of the activities of 14171 protein activity associated with the cell. An agent that modulates 14171 protein activity can be an agent as described herein, such as a nucleic acid or a protein, a naturally-occurring target molecule of a 14171 protein (e.g., a 14171 substrate or receptor), a 14171 antibody, a 14171 agonist or antagonist, a peptidomimetic of a 14171 agonist or antagonist, or other small molecule.

In one embodiment, the agent stimulates one or 14171 activities. Examples of such stimulatory agents include active 14171 protein and a nucleic acid molecule encoding 14171. In another embodiment, the agent inhibits one or more 14171 activities. Examples of such inhibitory agents include antisense 14171 nucleic acid molecules, anti14171 antibodies, and 14171 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 14171 protein or nucleic acid molecule. In one embodiment, the method involves administering an agent (e.g., an agent identified by a screening assay described herein), or combination of agents that modulates (e.g., up regulates or down regulates) 14171 expression or activity. In another embodiment, the method involves administering a 14171 protein or nucleic acid molecule as therapy to compensate for reduced, aberrant, or unwanted 14171 expression or activity.

Stimulation of 14171 activity is desirable in situations in which 14171 is abnormally downregulated and/or in which increased 14171 activity is likely to have a beneficial effect. For example, stimulation of 14171 activity is desirable in situations in which a 14171 is downregulated and/or in which increased 14171 activity is likely to have a beneficial effect. Likewise, inhibition of 14171 activity is desirable in situations in which 14171 is abnormally upregulated and/or in which decreased 14171 activity is likely to have a beneficial effect.

Other Embodiments

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a 14171 protein kinase, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 14171 protein kinase nucleic acid, polypeptide, or antibody.

The capture probes can be a set of nucleic acids from a selected sample, e.g., a sample of nucleic acids derived from a control or non-stimulated tissue or cell.

The method can include contacting the 14171 protein kinase nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 14171. Such methods can be used to diagnose a subject, e.g., to evaluate risk for a disease or disorder, to evaluate suitability of a selected treatment for a subject, to evaluate whether a subject has a disease or disorder. 14171 is associated with protein kinase activity, thus it is useful for disorders associated with abnormal protein kinase activity.

The method can be used to detect SNPs.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express or misexpress 14171 or from a cell or subject in which a 14171 mediated response has been elicited, e.g., by contact of the cell with 14171 nucleic acid or protein, or administration to the cell or subject 14171 nucleic acid or protein; contacting the array with one or more inquiry probe, wherein an inquiry probe can be a nucleic acid, polypeptide, or antibody (which is preferably other than 14171 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 14171 protein kinase (or does not express as highly as in the case of the 14171 protein kinase positive plurality of capture probes) or from a cell or subject which in which a 14171 protein kinase mediated response has not been elicited (or has been elicited to a lesser extent than in the first sample); contacting the array with one or more inquiry probes (which is preferably other than a 14171 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing 14171, e.g., analyzing structure, function, or relatedness to other nucleic acid or amino acid sequences. The method includes: providing a 14171 nucleic acid or amino acid sequence; comparing the 14171 sequence with one or more preferably a plurality of sequences from a collection of sequences, e.g., a nucleic acid or protein sequence database; to thereby analyze 14171.

Preferred databases include GenBank™. The method can include evaluating the sequence identity between a 14171 sequence and a database sequence. The method can be performed by accessing the database at a second site, e.g., over the internet.

In another aspect, the invention features, a set of oligonucleotides, useful, e.g., for identifying SNP's, or identifying specific alleles of 14171. The set includes a plurality of oligonucleotides, each of which has a different nucleotide at an interrogation position, e.g., an SNP or the site of a mutation. In a preferred embodiment, the oligonucleotides of the plurality are identical in sequence with one another (except for differences in length). The oligonucleotides can be provided with different labels, such that an oligonucleotide that hybridizes to one allele provides a signal that is distinguishable from an oligonucleotide that hybridizes to a second allele.

The invention also includes an array comprising a 14171 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be 14171. This allows a profile to be developed showing a battery of genes specifically expressed in one or more tissues.

In addition to such qualitative information, the invention allows the quantitation of gene expression. Thus, not only tissue specificity, but also the level of expression of a battery of genes in the tissue if ascertainable. Thus, genes can be grouped on the basis of their tissue expression per se and level of expression in that tissue. This is useful, for example, in ascertaining the relationship of gene expression in that tissue. Thus, one tissue can be perturbed and the effect on gene expression in a second tissue can be determined. In this context, the effect of one cell type on another cell type in response to a biological stimulus can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a kinase-associated or another 14171associated disease or disorder, progression of kinase-associated or another 14171-associated disease or disorder, and processes, such a cellular transformation associated with the kinaseassociated or another 14171-associated disease or disorder.

The array is also useful for ascertaining the effect of the expression of a gene on the expression of other genes in the same cell or in different cells (e.g., acertaining the effect of 14171 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including 14171) that could serve as a molecular target for diagnosis or therapeutic intervention.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 14171 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features a method of analyzing a sequence. The method includes: providing a 14171 sequence, or record, in computer readable form; comparing a second sequence to the 14171 sequence; thereby analyzing a sequence. Comparison can include comparing to sequences for sequence identity or determining if one sequence is included within the other, e.g., determining if the 14171 sequence includes a sequence being compared. In a preferred embodiment the 14171 or second sequence is stored on a first computer, e.g., at a first site and the comparison is performed, read, or recorded on a second computer, e.g., at a second site. E.g., the 14171 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

This invention is further illustrated by the following examples that should not be construed as limiting. The contents of all references, patents, and published patent applications cited throughout this application are incorporated herein by reference.

EXPERIMENTAL

Example 1

Tissue Distribution of 14171 Protein Kinase mRNA

Expression levels of 14171 in various tissues and cell lines were determined by quantitative RT-PCR (Taqman® brand quantitative PCR kit, Applied Biosystems). Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using β-2 microglobulin as an internal amplicon reference. The integrity of the RNA samples following DNase I treatment was confirmed by agarose gel electrophoresis and ethidium bromide staining. After phenol extraction cDNA was prepared from the sample using the SUPERSCRIPT™ Choice System following the manufacturer's instructions (GibcoBRL). A negative control of RNA without reverse transcriptase was mock reverse transcribed for each RNA sample.

Human 14171 expression was measured by TaqMan® quantitative PCR (Perkin Elmer Applied Biosystems) in cDNA prepared from a variety of normal and diseased (e.g., cancerous) human tissues or cell lines.

Probes were designed by PrimerExpress software (PE Biosystems) based on the sequence of the human 14171 gene. Each human 14171 gene probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both β2-microglobulin and target gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers (examples of primers for some experiments, forward: GGCACGGAA-GATCAGTGTCA, SEQ ID NO:9, reverse: CGAGGCGT-TCTTCTCCAACA, SEQ ID NO:10) plus 200 nM probe (examples of probe for some experiments: AGGGCTGTC- CACTGGTCCTCATCCTT, SEQ ID NO:11) for the target gene. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate human 14171 gene expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the human 14171 gene is normalized by subtracting the Ct value of the β-2 microglobulin gene to obtain a ACt value using the following formula: $_\Delta Ct = Ct_{human\ 59914\ and\ 59921} - Ct_{\beta-2\ microglobulin}$. Expression is then calibrated against a cDNA sample showing a comparatively low level of expression of the human 14171 gene. The $_\Delta Ct$ value for the calibrator sample is then subtracted from $_\Delta Ct$ for each tissue sample according to the following formula: $_{\Delta\Delta} Ct = _\Delta Ct_{sample} - _\Delta Ct_{calibrator}$. Relative expression $$ is then calculated using the arithmetic formula given by $2^{-\Delta\Delta Ct}$. Expression of the target human 14171 gene in each of the tissues tested is then graphically represented as discussed in more detail below.

In a general tissue survey, 14171 nucleic acid was found to be expressed at a high level in kidney and in epithelial cells from the prostate, at medium levels in liver and pancreas, at low levels in normal skin, fibrotic liver tissue, diseased aorta, pituitary gland, and normal tonsil and at trace levels in normal vein, normal artery, normal human umbilical vein endothelial cells, normal heart, coronary smooth muscle cells, human umbilical endothelial cells undergoing shear stress, primary osteoblasts, normal bladder, tissue from chronic obstructive pulmonary-diseased lung, tissue from inflammatory bowel-diseased colon, normal small intestine, tissue from a decubitus skin ulcer, and resting peripheral blood monocytes.

Experiments on a liver and hepatocyte-derived cells demonstrated expression of 14171 in HepG2 (immortalized human hepatocyte) cells and elevated expression in HepG2.2.15 (HepG2 stably transfected with a HBV genome) cells.

Northern blot hybridizations with various RNA samples are performed under standard conditions and washed under stringent conditions, i.e., 0.2×SSC at 65° C. A DNA probe corresponding to all or a portion of the 14171 cDNA (SEQ ID NO:3) can be used. The DNA is radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) are probed in ExpressHyb hybridization solution (Clontech) and washed at high stringency according to manufacturer's recommendations.

RNA was isolated from HepG2 (immortalized human hepatocyte cells) and HepG2.2.15 (HepG2 stably transfected with the HBV genome). The RNA was labeled by synthesizing P$^{33}$-labeled cDNA and hybridized to a gene array containing novel human genes identified by the inventors. 14171 RNA is 3.6 fold more abundant in HBV-infected HepG2 cells than in uninfected HepG2 cells.

Example 2

Recombinant Expression of 14171 in Bacterial Cells

In this example, 14171 is expressed as a recombinant glutathione-S-transferase (GST) fusion polypeptide in E. coli and the fusion polypeptide is isolated and characterized. Specifically, 14171 is fused to GST and this fusion polypeptide is expressed in E. coli, e.g., strain PEB199. Expression of the GST-14171 fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 3

Effect of 14171 on the NF-kappaB Reporter in HeLa Cells

HeLa cells were transfected with wt and kinase dead (KD) 14171 at two different concentrations in combination with 4 different reporters (Nuclear Factor-kappa B (NF-κB), serum-response elements (SRE), activator protein 1 (AP1) and cAMP response element (CRE)). Following overnight incubation the medium was changed and fresh medium was added. The cells were harvested after a further 36 to 40 hours and luciferase assays performed on the extracts. Following normalization, the fold activation was calculated relative to the empty expression vector control.

Construct Generation: The full length (FL) clone for 14171 was PCR amplified using the pfu enzyme (Stratagene, catalog # 600159) from plasmid DNA using 5' and 3' primers 5'GATGTGGTTGAATTCATGGAGGGCGACG-GCGGGACC3' (SEQ ID NO:12) and 5'GATGCTG-GCTCTAGAGGTCTTGCTTCGCCGCAGGAGTGT3' (SEQ ID NO:13) which contain EcoRI and XbaI sites, respectively. All PCR reactions were carried out in a volume of 200%1 (2 µl of the plasmid template at a concentration of 10 ng/µg, 20 µl DMSO, 20 µl 10×pfu enzyme buffer, 10 µl each of the 5' and 3' PCR primers at a concentration of 10 µM, 2 µl of 20 mM dNTP stock, 411 of enzyme and 132 µl of H$_2$O). The PCR parameters used were an initial denaturation step at 95° C. for 5 min, followed by 35 cycles of 95° C. for 45 sec, 62° C. for 45 sec and 72° C. for 4.5 min, and a final $$ extension step at 72° C. for 8 min. Following amplification an aliquot of the DNA was electrophoresed on an 0.8% agarose gel to verify correct size. The remainder of the DNA was purified using nucleo-spin columns (Clontech, catalog # K3051-2). Following purification, the DNA was digested with EcoRI and XbaI restriction enzymes (New England BioLab, catalog #'s 101L and 145L) and cloned into the expression vector pTracer-EF/V5-His (Invitrogen, catalog # v887-20), using T4 DNA ligase (New England BioLab, catalog # 202L). All targets are thereby tagged at the C terminus with the V5 and 6×His tags. The kinase dead (KD) mutant containing a single K to A substitution at position 51 which renders the enzyme inactive was generated by site-directed mutagenesis (AAG to GCG). Both wt and KD constructs were sequence verified. These constructs were used for this example and for Example 4.

Transient Transfection Assays: HeLa cells were maintained in DMEM medium (GiBco, catalog # 12378-022) containing 10% fetal bovine serum (FBS) (GiBco, catalog #

12477), 10 uM Non Essential Amino Acids (GiBco, catalog# 12383-014), 1 mM sodium pyruvate (GiBco, catalog# 12454-013) and 100 units/ml penicillin-streptomycin (GiBco, catalog# 15140-122). All transient transfection assays were carried out in 96-well plates (Falcon, catalog # 353072). Approximately 24 hr prior to transfection, HeLa cells were seeded at a density of 8,000 cells per well. The following day the DNA-transfection reagent mixture was prepared in a master 96-well plate. A total of 100 ng DNA (50 ng of reporter DNA, a dose response of the 14171 kinase from 0 to 50 ng, plus empty vector to the final total of 100 ng) was added to each well of this plate in a total volume of 4 µl. The reporter DNAs used were all obtained from Stratagene (pNFKB-Luc, catalog # 219078; pSRE-Luc, catalog # 219080; pCRE-Luc, catalog # 219076; pAP1-Luc, catalog # 219074). A scaled-up volume of transfection reagent Fugene 6 (Roche, catalog # 1814 443) was prepared. This consisted of diluting the Fugene to a ratio of 0.3 µl: 9.7 µl DMEM per well in a conical tube. The Fugene was added in a drop wise fashion to the DMEM and the mixture was allowed to equilibrate for 10 min at room temperature (RT). 10 µl of the diluted Fugene was then added to each well of the transfection cocktail master plate and gently pipetted 3× to mix the DNA and transfection reagent. After allowing the plate to equilibrate at RT for 45 min, the 14 µl of DNA-Fugene mix was taken from each well of the master plate and transferred to the appropriate wells of the 96-well plate of HeLa cells. Following overnight incubation the media was aspirated and fresh media was added to all plates; 100 µl of 10% FBS in DMEM (serum-containing) to plate 1 or 0.5% FBS in DMEM (serum-free) to identical transfection plate 2. Cells were harvested at 36 to 40 hours posttransfection. Again the media was aspirated and the cells were washed by adding 100 µl of cold PBS to each well. Following aspiration of the cold PBS the plates were either stored at −80° C. for subsequent assay or the luciferase assay was carried out immediately. All experiments were carried out in duplicate or triplicate and all experiments were repeated.

Luciferase Assays: A dual luciferase kit purchased from Promega (catalog # E1960, VWR) was used to measure luciferase values. The 5× luciferase assay lysis buffer was diluted to 1× in sterile water and 60 µl of the 1× buffer was added to each well. The plates were rocked gently at RT for 45 min to 1 hr to allow the cells to lyse. The lysis buffer-cell suspension was gently mixed by pipetting (5×), and 20 µl of the lysis mixture was added into a luminometer 96 well plate. Sufficient luciferase substrate was prepared according to the manufacturers recommendations and the plates were read on a Tropix machine. Samples were normalized using the empty expression vector control and the fold activation relative to the empty expression vector was calculated.

In these studies, cells transfected with 50 ng of the 14171 full length clone and maintained in serum-free conditions induced a 35-fold activation of the luciferase signal for the NF-κB reporter construct, but not the SRE, API or CRE construct. Additional studies failed to demonstrate activation of other reporter constructs (e.g., nuclear factor of activated T cells (NFAT), p53 tumor suppressor, interferon-gamma activation site (GAS), interferon gamma response element (ISRE), interleukin-6-response element (IL6-RE), or haematopoietin receptor response element (HRRE). Cells transfected with the construct containing the kinase dead mutant of 14171 only induced a 4-fold activation of the NF-κB luciferase signal. The results were similar for serum-containing conditions, with the 14171 clone inducing 31-fold activation NF-κB luciferase signal, with no activation of the SRE, AP1 or CRE signals and only 4-fold activation by the kinase dead mutant. Similar results were obtained from cotransfection of 14171 protein kinase constructs with the NF-κB reporter construct in Jurkat cells (human acute T cell leukemia cell line). This result was in contrast to the results with other RIP kinases. For example, while transfection with wild type RIP2 (CARD3) kinase causes a dose-dependent activation of NF-κB, the mutation to kinase-dead form of RIP2 does not abolish the activation of NF-κB in kinase-dead RIP2-transfected cells.

Further co-transfection studies using activators of the NF-κB pathway determined that the inactive 14171 protein kinase mutant blocked activation by phorbol myristate acetate (PMA, 10 ng/ml), but not the activation by tumor necrosis factor (TNF)-alpha (10 ng/ml) nor the activation by sorbitol (200 mM). This result suggests that 14171 participates in the pathway leading from PMA stimulation to NF-κB activity.

The 14171 protein was dissected to confirm the portions of the molecule responsible for the ability to activate NF-κB. In addition to the wild type and K51A kinase dead mutant (KD) described above, three deletion mutants were constructed: "K" having the kinase domain and few other residues (amino acid residues 1-289 of SEQ ID NO:2), "KS" having all the residues of the "K" plus the adjacent spacer region (amino acid residues 1-486 of SEQ ID NO:2), and "ANK" having only the ankyrin repeat domains (amino acid residues 437-784 of SEQ ID NO:2). After confirmation of their expression, the activity of the five constructs was tested. Only the KS construct activated as much of the NF-κB reporter as wild type 14171 (the K and ANK constructs stimulated near-zero activity, same as the KD mutant).

Example 4

Determination of Kinase Activity of 14171 Protein Kinase

In-vitro kinase assays were carried out in 6 well plates (Falcon catalog # 353046). Again, the transfection procedure is the same as given above except that everything was scaled up from the 96 well to the 6 well plate system. Following transfection, cells were washed as before and 300 µl of lysis buffer (50 mM HEPES, pH 7.5, 150 mM NaCl, 10% glycerol, 1% Triton X-100, 1.5 mM MgCl$_2$, 1 mM EDTA, 100 mM NaF, 1 mM Na$_3$VO$_4$, proteinase inhibitors (2 ug/ml leupeptin; 2 ug/ml aprotinin; 2 ug/ml pepstatin; 200 uM PMSF; 1mMDTT)) was added to each well and cells were placed on ice for 10 min. The cells were scraped off the plate and the cell lysate was transferred to eppendorf tubes, vortexed and spun at 14,000 rpm for 10 min. The supernatant was transferred to a fresh tube and 20 µl of protein G plus agarose (Calbiochem., catalog # 80000-744) was added to each tube and tubes were placed on a rotator at 4° C. for 15 min. After spinning for 5 min at 14,000 rpm the supernatant was transferred to a fresh tube. 2 µl of the anti-V5 antibody (Invitrogen, catalog # R960-25) was added and the tubes were again placed on a rotator at 4° C. for 2 hr. 25 µl of protein G beads were added and the tubes were allowed to rotate for a further 30 mins at 4° C. Following a quick spin for 30 seconds the supernatant was removed and discarded and the beads were washed twice in 750 µl lysis buffer. This was followed by two further washes in 300 µl kinase assay buffer (without hot ATP). The kinase assay buffer consists of 20 mM HEPES, pH 7.5, 5 mM MgCl$_2$, 5 mM MnCl$_2$, 20 mM NaCl, 0.01% Tween-20, 2 mM DTT, 100 µM ATP, 500

μM Na₃VO₄, 10 μCi rP³² ATP. After the final wash, the tubes were spun again to ensure that as much of the supernatant as possible could be removed. The beads were resuspended in 30 μl of the fresh radioactive kinase buffer, gently mixed by inverting tubes and incubated at 30° C. for 30 min. Easy Tide ATP was obtained from NEN (catalog # BLU502A250UC). Following centrifugation at 14,000 rpm for 1 min, the supernatant was carefully removed, again incorporating an additional spin step and the beads were resuspended in 25 μl of 1.5×loading buffer. The loading dye-beads solution was placed at 100° C. for 5 min and then loaded onto a NuPAGE 4-12% Bis-Tris gel (Invitrogen, catalog # NPO₃₂₁) and the gel was run at 100 V until the dye front reached 5 mm from the bottom of the gel (approx. 60 min). The dye front was then removed and the gel was transferred to nitrocellulose membrane (Invitrogen, catalog # LC2001) using a Mini Trans-Blot Cell apparatus (BioRad) for 1 hr at 150 V. The gel was dried and exposed to Kodak film at −70° C. for 30 min to 24 hrs.

The resulting film showed 14171 protein had kinase activity as manifested in autophosphorylation of the wt kinase. However, the KD mutant is inactive and showed no autophosphorylation. To determine that equivalent levels of wt and KD versions of each kinase were being expressed in the cell, western blot assays were performed as described using the antibody which recognizes the α-V5 tag. Again, the positions of the protein bands relative to marker controls are shown on the left side of the gel. The resulting blot showed that wt and KD 14171 are expressed at approximately equivalent levels in the cell.

Further studies identified truncated forms of 14171 protein kinase having kinase activity on standard kinase substrates. Truncated 14171 protein kinase molecules were cloned in SF-9 insect cells as glutathione S-transferase (GST) fusion proteins to aid their identification and purification. Insoluble fusion proteins (including the GST-fusion with full length 14171 protein kinase) were disqualified from the analysis. The soluble GST-14171 protein kinase fusion proteins were tested for their ability to phosphorylate biotinylated myelin basic protein (MBP, Amersham Biosciences, Piscataway, N.J.). A construct of GST fused to the N-terminus of a partial 14171 molecule amino acid residues 1-350 of SEQ ID NO:2 (the kinase domain plus a portion of the spacer region) phosphorylated MBP.

Example 5

Expression of 14171 in Respiratory Cells and Tissues

Respiratory-related tissues and cultured cells were examined for evidence of 14171 expression by the TaqMan® quantitative PCR method described above for Example 1. Some differences in the methodology lie in the use of b2-microglobulin amplicon reference control and cycles which hold for 2 min at 50° C. and 10 min at 95° C., followed by two-step PCR for 40 cycles of 95° C. for 15 sec followed by 60° C. for 1 min. These respiratory-related expression experiments demonstrated no expression in normal lung tissue, low expression of 14171 nucleic acid in samples of chronic obstructive pulmonary disease tissue, medium levels of 14171 nucleic acid in idiopathic pulmonary fibrosis, medium to high levels of expression of 14171 nucleic acid in nasal polyp tissue from an asthmatic patient, high expression of 14171 nucleic acid in a bronchial biopsy typical of bronchitis and cystic fibrosis and high expression of 14171 nucleic acid in a asthma bronchial biopsy.

Experiments on 14171 nucleic acid expression on cultured cells demonstrated a medium level of expression in resting normal human bronchial epithelial cells and a high level of expression in human bronchial epithelial cells 4 hours after activation with IL-4 or IL-3 at 100 ng/ml typically seen in Th2-mediated diseases such as asthma and allergic rhinitis.

In mouse lungs, the expression of the orthologous mouse 14171 nucleic acid was examined in a disease model of allergic airway disease. The probes for this study were derived from the sequence of PKC-regulated kinase (PKK), GenBank Accession No. AF302127: forward: TCCGAGT-TGCTGTCACAGTTG (SEQ ID NO:14); reverse: CGATGGGAGCTTGCATTCA(SEQ ID NO:15); probe: TCCCAGACTCTTGAAGGCCCCGA(SEQ ID NO:16). PKK (mouse ortholog of 14171) is expressed at low levels in normal mice, but is expressed at higher levels 3 hours after ovalbumin challenge in mice 8 days after sensitization by ovalbumin. A degree of stimulation of PKK (mouse ortholog of 14171) expression after ovalbumin challenge remains at 21 days after sensitization.

Example 6

Expression of 14171 in Tumors

The expression of 14171 was studied in tumor-related conditions by the TaqMan® quantitative PCR method described above in Example 1. In a general survey, 14171 expression was found to be at higher levels in tumor tissues compared to the corresponding normal tissues from those organs. For example, 14171 expression was found at a high level in lung tumor, but only at a trace level in normal lung; 14171 expression was found at a medium level in colon tumor tissue, but a low level in normal colon; 14171 expression was found at a medium level in normal prostate, at a low level in prostate tumor tissue, but at a trace level in tissue from a benign hypertrophied prostate; 14171 expression was found at a medium level in breast tumor tissue, but a low level in normal breast tissue; and 14171 expression was found at a trace level in ovary tumor tissue, but was not found in normal ovary tissue.

Further examination of 14171 expression in tumor-related tissues involved TaqMan® quantitative PCR analysis on several normal tissues, e.g., lung, colon, breast and ovary, and corresponding tumor tissues. This experiment confirmed the general tissue survey, with the tumor tissues showing higher 14171 expression than the corresponding normal tissue from the same organ.

A more detailed study of tumor-related 14171 expression involved TaqMan® quantitative PCR analysis on ovary and ovarian cancers. Again, no expression was found in normal ovary, but 14171 expression was found at medium to trace levels in a variety of primary serous ovarian cancer tissues, and 14171 expression was found at low to high levels in clear cell ovarian tumor tissues. This pattern of 14171 tumor expression was not repeated in peripheral tissues, such as omentum and fallopian tube tissues.

Example 7

Expression in Cell Models of Tumor and Tumor Suppression

Tumor cell lines induced to express p53, a tumor suppressor gene, reduce their expression of 14171. For example, 14171 expression was examined in H125 lung cancer cells. A p53/estrogen receptor fusion protein (p53ER) was introduced into the p53 null cell line H125 and p53 activity was induced by addition of the estrogen analogue tamoxifen (4HT) to the cell culture medium. RNA was isolated from the cells and underwent TaqMan® quantitative PCR analysis by the method in Example 1. Control H125 cells have medium levels of 14171 expression. When these cells are transfected with the p53ER vector, and induced with tamoxifen the 14171 expression drops to low levels. This drop does not occur in induced H125 cells transfected with a control vector.

14171 expression also was examined by the TaqMan® quantitative PCR analysis method from Example 1 in the ovarian cancer cell line, SKOV3, in the presence or absence of p53 expression. A tetracycline-inducible expression vector with or without the p53 protein-coding sequence was introduced into the p53 null cell line SKOV3. Due to leaky expression from this vector, even in the absence of tetracycline, the SKOV3/p53 cells express less 14171 than vector controls. SKOV3 cells with the p53-containing vector or the control vector were induced by the addition of tetracycline. At 6 and 15 hr time points posttetracycline induction, there was an increase in 14171 in both the vector control and SKOV3/p53 cells, suggesting that the increase is an effect of the tetracycline itself, and not due to p53 expression. At all time points, the level of 14171 expression is lower in the SKOV3/p53 cells in comparison to the respective time points for vector control SKOV3 cells.

Example 8

Generation of Antibodies to 14171

Portions of the 14171 sequence were selected to generate antibodies. The peptides described below were synthesized and chemically coupled to keyhole limpet hemocyanin or bovine serum albumin using a maleimide linkage kit from Pierce Chemical Company (Rockford, Ill.). The conjugate was mixed with Freund's adjuvant and injected into New Zealand White rabbits on day zero and day 21. Serum from immunized rabbits was obtained and compared to preimmune serum for binding to the 14171 peptide in an ELISA assay. The peptides used as immunogens are: amino acids 764 to 784 of SEQ ID NO:2 (QSLKFQGGHGPAATLLRR-SKT, SEQ ID NO:17), amino acids 349 to 368 of SEQ ID NO:2 (GPEELSRSSSESKLPSSGSG, SEQ ID NO:18), and amino acids 281 to 300 of SEQ ID NO:2 (SETEDLCEKP-DDEVKETAHD, SEQ ID NO:19). An affinity-purified rabbit polyclonal antibody against SEQ ID NO:17 recognized recombinant 14171 protein in transfected 293T cells as well as endogenous 14171 in A549 (lung adenocarcinoma) cells, NC1-H292 (bronchiolar epithelial cells) and HeLa (cervical adenocarcinoma) cells.

Example 9

Identification of 14171 Substrate

Antibodies directed to epitopes on phosphorylated molecules but not nonphosphorylated versions of these molecules were employed for these studies. These antibodies (Phospho-(Ser/Thr) Kinase Substrate Antibody Sampler Kit, Cell Signaling Technology, Beverly, Mass.) recognize phosphorylated serine or threonine within the context of a protein motif that is phosphorylated by Akt kinase (Akt), protein kinase C (PKC), protein kinase A (PKA), mitogen activated protein kinase (MAPK)/cyclin dependent kinase (CDK), phosphoinositide dependent kinase-1 (PDK1) or ataxia telangiectasia mutated protein kinase (ATM)/ataxia telangiectasia and Rad3 related protein (ATR). Cells were transfected with empty vector, vector having wild type 14171 or the K51A KD mutant, then lysed in a solution of 50 mM HEPES, pH 7.5, 150 mM NaCl, 10% glycerol, 1% TRITON X-100 (t-Octylphenoxypolyethoxyethanol, nonionic detergent, Union Carbide subsidiary of Dow Chemical Co., Midland Mich.), 1.5 mM $MgCl_2$, 1 mM EDTA, 100 mM NaF, 1 mM $NA_3VO_4$, and 1 mM dithiothreitol (DTT). Cell lysates (expected to contain total protein soluble in the nonionic detergent-containing buffer) were analyzed with the phosphor antibodies on western blots. The blot stained by the phospho-(Thr) MAPK/CDK substrate antibody recognized a protein of about 42-45 kDa in the lysate of the cells transfected with the wild type 14171-containing vector, but not in the lysate of the cells transfected with the empty vector or the KD-containing vector. (The anti-V5 antibody stained the 14171 wild type protein and 14171 KD protein at about 80 kDa to confirm protein synthesis in nonempty vector transfectants.) The phospho-(Thr) MAPK/CDK substrate antibody recognizes phosphothreonine residues only when they are followed by proline residues (T*P). The conclusion to this study is that the intracellular substrate for 14171 protein kinase can be a MAPK/CDK substrate of 42-45 kDa with a T-P motif. This molecular weight range suggests that the target molecule has between about 350 amino acid residues and about 409 amino acid residues (using a range of 110 to 120 Da per residue), although proteins outside this range could also be substrates and just migrate at 42-45 kDa on SDS-PAGE. A brief survey of some human signaling pathway proteins which fit these criteria identifies some candidate molecules, e.g., Interferon Regulatory Factor (IRF)-2 (349 amino acid residues, has at least one T-P motif, GenPept Accession No. NP_002190) Early Growth Response Protein-3 (387 amino acid residues, has at least two T-P motifs, GenPept Accession No. Q06889), cyclic AMP-dependent protein kinase A (PKA) regulatory subunit 1A (381 amino acid residues, has at least one T-P motif, GenPept Accession No. NP_002725) and G1/S specific cyclin E1 (410 amino acid residues, has at least two T-P motifs, one of which, having T395, is known to be phosphorylated, GenPept Accession No. P24864).

Example 10

Identification of Alternative Substrates 14171 Protein Kinase

This study tested direct phosphorylation by 14171 protein kinase on a panel of phosphorylatable peptides and other serine/threonine kinase substrates. Substrate phosphorylation over time at room temperature was tested using various concentrations of the 14171 protein kinase (a GST-14171 fusion protein (glutathione S-transferase (GST) fused to the N-terminus of a partial 14171 molecule (amino acid residues 1-350 of SEQ ID NO:2)). The 70 μl reaction mixture contained 0.5 μM ATP, 0.01 μCi [γ-$^{33}$P]ATP, 50 mM HEPES, pH 7.5, 2.5 mM $MgCl_2$, 62.5 μM $MnCl_2$, 2 mM DTT, 0.1% BSA, 0.1% TWEEN 20 (Polyoxyethylenesorbitan monolaurate, Uniqema, a business unit of ICI Americas Inc., Newcastle, Del.) and 0.5 μM substrate. At each timepoint, the stop solution (50 mM EDTA, 1×PBS, 0.1% TRITON X-100 (t-Octylphenoxypolyethoxyethanol, nonionic detergent, Union Carbide subsidiary of Dow Chemical Co., Midland Mich.), and 0.3 mg streptavidin PVT scintillation proximity assay (SPA) beads (Amersham Biosciences Corp, Piscataway, N.J.) were added to each well to stop the reaction. The beads were allowed to settle overnight. The sample was counted in Trilux beta counter (Perkin Elmer Life Sciences Inc., Boston, Mass.).

This study identified strong phosphorylation of bovine myelin basic protein (biotinylated MBP, Amersham Biosciences, Piscataway, N.J.), a standard kinase substrate and weak phosphorylation of the following peptide, named peptide 3: BiotinKKRFSFKKSFKLSGFSFK-COOH (SEQ ID NO:20, synthesized by New England Peptide, Inc., Fitchburg, Mass.). For example, at the two hour timepoint, the counts per minute for 10 nM of the GST-14171 protein kinase fusion protein to phosphorylate MBP was about 21,000 cpm with a signal-to-noise ratio of 13; the cpm for 10 nM GST-14171 protein kinase fusion protein to phosphorylate peptide 3 was about 11,000 cpm with a signal-to-noise ratio of 9.

At least one version of bovine MBP (GenPept Accession No. MBBOB) has two T-P motifs. Interestingly, peptide 3 has no T-P motif, however, its parent molecule, Myristoylated Alanine-Rich C-kinase Substrate (331 amino acid residues, GenPept Accession No. P29966) has at least two T-P motifs just prior to this peptide in the protein sequence. Phosphorylation of peptide 3 by 14171 protein kinase could be due to recognition of the peptide sequence and non-specific phosphorylation of the peptide as a secondary site adjacent to the neighboring T-P substrate site.

Example 11

Effect of 14171 Protein Kinase on Interleukin-8 Reporter

An Interleukin (IL)-8 luciferase reporter construct was cotransfected with 14171 protein kinase constructs in 293T cells (transformed human renal epithelial line expressing two viral oncogenes, adenovirus E1a and SV40 large T antigen) and assayed essentially as described in Example 3. Cotransfection of neither the empty vector nor the vector with the 14171 protein kinase dead (K51A KD) mutant activated the IL-8 reporter. However, cotransfection of the wild type 14171 protein kinase vector strongly activated the IL-8 reporter.

Example 12

Use of RNAi Technology to Affect 14171 Activity

RNA interference (RNAi) is the process by which small double stranded RNA molecules introduced or transcribed in cells can inhibit gene expression of homologous genes in that cell by post-transcriptional degradation of mRNA. Studies were undertaken to apply this technology to both endogenous and overexpressed 14171 protein kinase. Expression studies revealed that 14171 protein kinase is expressed in 293T cells. Therefore, all the RNAi studies (method from Elbashir et al. (2001) *Nature* 411:494-498) were performed in 293T cells.

Several RNAi target sequences were identified and siRNAs were produced based on these sequences (Dharmacon, Lafayette, Colo.) and tested. In NF-κB luciferase co-transfection experiments performed as in Example 3 above, scrambled siRNA sequences had little effect on the NF-κB activity induced by co-transfected 14171 protein kinase. However, siRNA duplexes introduced for three target sequences, had efficacy in reducing (by 3- to 8-fold) 14171-induced NF-κB activity. These target sequences and the sense strands of their double stranded siRNAs are:

9, targeting AAGAACATCCTGCACATCATG, SEQ ID NO:21, beginning at residue 679 of SEQ ID NO:3, with the following structure:

```
                                           SEQ ID NO:24
    Sense            5'AAGAACAUCCUGCACAUCAUGdTdT3'

SEQ ID NO:25
    anti-Sense       3' dTdTUUCUUGUAGGACGUGUAGUAC5'
```

10, targeting AAGAAGATGGAGATGGCCAAG, SEQ ID NO:22, beginning at residue 211 of SEQ ID NO:3, with the following structure:

```
                                           SEQ ID NO:26
    Sense            5'AAGAAGAUGGAGAUGGCCAAGdTdT3'

SEQ ID NO:27
    anti-Sense       3' dTdTUUCUUCUACCUCUACCGGUUC5'
``` and #11 targeting AACCTTCAACCAGCGATCTGG, SEQ ID NO:23, beginning at residue 1181 of SEQ ID NO:3, with the following structure:

```
                                           SEQ ID NO:28
    Sense            5'AACCUUCAACCAGCGAUCUGGdTdT3'

SEQ ID NO:29
    anti-Sense       3' dTdTUUGGAAGUUGGUCGCUAGACC5'
```

These siRNAs had no inhibitory effect on the NF-κB activity induced by a non-14171 co-transfectant (RIP2). Western blots detecting the in-frame fused tag (V5 in 14171 constructs) in the transfected cell lysates confirmed that the siRNAs #9, 10, and 11 suppressed 14171 protein kinase expression, not the expression of a marker alpha tubulin gene nor the transfected RIP2 gene.

Further studies examined the effect of the siRNAs #9, 10, and 11 on endogenous 14171 protein kinase activity. Only the NF-κB reporter was transfected into 293T cells (which express endogenous 14171 protein kinase, as described above), which then were stimulated with activators of NF-κB activity in the presence of no siRNA, scrambled siRNA or siRNA #9, #10 or #11. NF-κB activity in untreated transfectants was minimal. Both PMA and TNFα stimulated transfected NF-κB activity, which was undiminished by scrambled siRNA. However, NF-κB activity was significantly reduced by siRNA #9 and #10 in PMA-treated cells, but not TNFαα-treated cells. siRNA #11 did not affect either PMA-nor TNFα-stimulated NF-κB activity, although an effect on PMA-stimulated activity would have been expected based on the experiments with transfected 14171 protein kinase. Nevertheless, expression studies in these cells showed that endogenous 14171 expresion was suppressed by the siRNAs #9, 10 and 11 in both the PMA- and the TNFα-treated cells. This result confirms the result in Example 3 that 14171 protein kinase is not involved in the TNFα pathway of NF-κB activity.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

Those skilled in the art will recognize, or be able to ascertain using no more than routine experimentation, many equivalents to the specific embodiments of the invention described herein. Such equivalents are intended to be encompassed by the following claims.

---

The invention claimed is:

1. An isolated polypeptide selected from the group consisting of:
   a) a polypeptide which is encoded by a nucleic acid molecule comprising a nucleotide sequence selected from the group consisting of the nucleotide sequence of SEQ ID NO:1 and SEQ ID NO:3;
   b) a polypeptide comprising amino acid residues 1 to 350 of SEQ ID NO:2, wherein the polypeptide has kinase activity; and
   c) a polypeptide comprising an amino acid sequence at least 95% identical to SEQ ID NO:2, wherein the polypeptide has kinase activity.

2. The polypeptide of claim 1 further comprising heterologous amino acid sequences.

3. A method for identifying a compound which binds to a polypeptide comprising the steps of:
   a) contacting the polypeptide of claim 1 with a test compound; and
   b) determining whether the polypeptide binds to the test compound.

4. The method of claim 3, wherein the binding of the test compound to the polypeptide is detected by a method selected from the group consisting of:
   a) detection of binding by direct detecting of test compound/polypeptide binding;
   b) detection of binding using a competition binding assay; and
   c) detection of binding using an assay for protein kinase-mediated phosphorylation.

5. A method for identifying a compound which modulates the activity of a polypeptide, comprising:
   a) contacting the polypeptide of claim 1 with a test compound; and
   b) determining the effect of the test compound on the activity of the polypeptide to thereby identify a compound that modulates the activity of the polypeptide.

6. The method of claim 5, wherein the activity of the polypeptide is determined in a kinase assay using a protein or peptide capable of being phosphorylated.

7. The polypeptide of claim 1, wherein the polypeptide comprises SEQ ID NO:2.

8. The method of claim 3, wherein the polypeptide comprises the amino acid sequence of SEQ ID NO:2.

9. The method of claim 3, wherein the polypeptide is immobilized on a solid surface.

10. The method of claim 3, wherein the test compound is directly or indirectly labeled.

11. The method of claim 4, wherein the method comprises ATP binding to the polypeptide.

12. The method of claim 5, wherein the polypeptide comprises the amino acid sequence of SEQ ID NO:2.

13. The method of claim 6, wherein the protein or peptide capable of being phosphorylated has a T-P motif.

14. An isolated polypeptide consisting of the amino acid sequence of SEQ ID NO:2.

* * * * *

SEQUENCE LISTING

```
<160> NUMBER OF SEQ ID NOS: 29

<210> SEQ ID NO 1
<211> LENGTH: 3860
<212> TYPE: DNA
<213> ORGANISM: H. sapiens
<220> FEATURE:
<221> NAME/KEY: CDS
<222> LOCATION: (17)...(2371)
<223> OTHER INFORMATION:
<220> FEATURE:
<221> NAME/KEY: misc_feature
<222> LOCATION: (1)...(3860)
<223> OTHER INFORMATION: n = A,T,C or G

<400> SEQUENCE: 1
ccacgcgtcc ggcgcg atg gag ggc gac ggc ggg acc cca tgg gcc ctg gcg        52
               Met Glu Gly Asp Gly Gly Thr Pro Trp Ala Leu Ala
                 1               5                  10 ctg ctg cgc acc ttc gac gcg ggc gag ttc acg ggc tgg gag aag gtg         100
Leu Leu Arg Thr Phe Asp Ala Gly Glu Phe Thr Gly Trp Glu Lys Val
            15                  20                  25 ggc tcg ggc ggc ttc ggg cag gtg tac aag gtg cgc cat gtc cac tgg         148
Gly Ser Gly Gly Phe Gly Gln Val Tyr Lys Val Arg His Val His Trp
        30                  35                  40 aag acc tgg ctg gcc atc aag tgc tcg ccc agc ctg cac gtc gac gac         196
Lys Thr Trp Leu Ala Ile Lys Cys Ser Pro Ser Leu His Val Asp Asp
 45                  50                  55                  60 agg gag cgc atg gag ctt ttg gaa gaa gcc aag aag atg gag atg gcc         244
Arg Glu Arg Met Glu Leu Leu Glu Glu Ala Lys Lys Met Glu Met Ala
                65                  70                  75 aag ttt cgc tac atc ctg cct gtg tat ggc atc tgc cgc gaa cct gtc         292
Lys Phe Arg Tyr Ile Leu Pro Val Tyr Gly Ile Cys Arg Glu Pro Val
            80                  85                  90 ggc ctg gtc atg gag tac atg gag acg ggc tcc ctg gaa aag ctg ctg         340
Gly Leu Val Met Glu Tyr Met Glu Thr Gly Ser Leu Glu Lys Leu Leu
        95                 100                 105 gct tcg gag cca ttg cca tgg gat ctc cgg ttc cga atc atc cac gag         388
Ala Ser Glu Pro Leu Pro Trp Asp Leu Arg Phe Arg Ile Ile His Glu
    110                 115                 120 acg gcg gtg ggc atg aac ttc ctg cac tgc atg gcc ccg cca ctc ctg         436
Thr Ala Val Gly Met Asn Phe Leu His Cys Met Ala Pro Pro Leu Leu
125                 130                 135                 140 cac ctg gac ctc aag ccc gcg aac atc ctg ctg gat gcc cac tac cac         484
His Leu Asp Leu Lys Pro Ala Asn Ile Leu Leu Asp Ala His Tyr His
                145                 150                 155 gtc aag att tct gat ttt ggt ctg gcc aag tgc aac ggg ctg tcc cac         532
Val Lys Ile Ser Asp Phe Gly Leu Ala Lys Cys Asn Gly Leu Ser His
            160                 165                 170 tcg cat gac ctc agc atg gat ggc ctg ttt ggc aca atc gcc tac ctc         580
Ser His Asp Leu Ser Met Asp Gly Leu Phe Gly Thr Ile Ala Tyr Leu
        175                 180                 185 cct cca gag cgc atc agg gag aag agc cgg ctc ttc gac acc aag cac         628
Pro Pro Glu Arg Ile Arg Glu Lys Ser Arg Leu Phe Asp Thr Lys His
    190                 195                 200
```

-continued

| | | |
|---|---|---|
| gat gta tac agc ttt gcg atc gtc atc tgg ggc gtg ctc aca cag aag<br>Asp Val Tyr Ser Phe Ala Ile Val Ile Trp Gly Val Leu Thr Gln Lys<br>205                            210                            215                      220 | 676 |
| aag ccg ttt gca gat gag aag aac atc ctg cac atc atg gtg aag gtg<br>Lys Pro Phe Ala Asp Glu Lys Asn Ile Leu His Ile Met Val Lys Val<br>                        225                            230                            235 | 724 |
| gtg aag ggc cac cgc ccc gag ctg ccg ccc gtg tgc aga gcc cgg ccg<br>Val Lys Gly His Arg Pro Glu Leu Pro Pro Val Cys Arg Ala Arg Pro<br>                      240                            245                            250 | 772 |
| cgc gcc tgc agc cac ctg ata cgc ctc atg cag cgg tgc tgg cag ggg<br>Arg Ala Cys Ser His Leu Ile Arg Leu Met Gln Arg Cys Trp Gln Gly<br>                        255                            260                            265 | 820 |
| gat ccg cga gtt agg ccc acc ttc caa gaa att act tct gaa acc gag<br>Asp Pro Arg Val Arg Pro Thr Phe Gln Glu Ile Thr Ser Glu Thr Glu<br>270                            275                            280 | 868 |
| gac ctg tgt gaa aag cct gat gac gaa gtg aaa gaa act gct cat gat<br>Asp Leu Cys Glu Lys Pro Asp Asp Glu Val Lys Glu Thr Ala His Asp<br>285                            290                            295                            300 | 916 |
| ctg gac gtg aaa agc ccc ccg gag ccc agg agc gag gtg gtg cct gcg<br>Leu Asp Val Lys Ser Pro Pro Glu Pro Arg Ser Glu Val Val Pro Ala<br>                            305                            310                            315 | 964 |
| agg ctc aag cgg gcc tct gcc ccc acc ttc gat aac gac tac agc ctc<br>Arg Leu Lys Arg Ala Ser Ala Pro Thr Phe Asp Asn Asp Tyr Ser Leu<br>                      320                            325                            330 | 1012 |
| tcc gag ctt ctc tca cag ctg gac tct gga gtt tcc cag gct gtc gag<br>Ser Glu Leu Leu Ser Gln Leu Asp Ser Gly Val Ser Gln Ala Val Glu<br>                        335                            340                            345 | 1060 |
| ggc ccc gag gag ctc agc cgc agc tcc tct gag tcc aag ctg cca tcg<br>Gly Pro Glu Glu Leu Ser Arg Ser Ser Ser Glu Ser Lys Leu Pro Ser<br>350                            355                            360 | 1108 |
| tcc ggc agt ggg aag agg ctc tcg ggg gtg tcc tcg gtg gac tcc gcc<br>Ser Gly Ser Gly Lys Arg Leu Ser Gly Val Ser Ser Val Asp Ser Ala<br>365                            370                            375                            380 | 1156 |
| ttc tct tcc aga gga tca ctg tcg ctg tcc ttt gag cgg gaa cct tca<br>Phe Ser Ser Arg Gly Ser Leu Ser Leu Ser Phe Glu Arg Glu Pro Ser<br>                      385                            390                            395 | 1204 |
| acc agc gat ctg ggt acc aca aga cgt cca gaa gaa gaa gct tgt gga<br>Thr Ser Asp Leu Gly Thr Thr Arg Arg Pro Glu Glu Glu Ala Cys Gly<br>                        400                            405                            410 | 1252 |
| tgc cat cgt gtc cgg gac acc agc aaa ctg atg aag atc ctg cag ccg<br>Cys His Arg Val Arg Asp Thr Ser Lys Leu Met Lys Ile Leu Gln Pro<br>                      415                            420                            425 | 1300 |
| cag gac gtg gac ctg gca ctg gac agc ggt gcc agc ctg ctg cac ctg<br>Gln Asp Val Asp Leu Ala Leu Asp Ser Gly Ala Ser Leu Leu His Leu<br>430                            435                            440 | 1348 |
| gcg gtg gag gcc ggg caa gag gag tgc gcc aag tgg ctg ctg ctc aac<br>Ala Val Glu Ala Gly Gln Glu Glu Cys Ala Lys Trp Leu Leu Leu Asn<br>445                            450                            455                            460 | 1396 |
| aat gcc aac ccc aac ctg agc aac cgt agg ggc tcc acc ccg ttg cac<br>Asn Ala Asn Pro Asn Leu Ser Asn Arg Arg Gly Ser Thr Pro Leu His<br>                      465                            470                            475 | 1444 |
| atg gcc gtg gag agg agg gtg cgg ggt gtc gtg gag ctc ctg ctg gca<br>Met Ala Val Glu Arg Arg Val Arg Gly Val Val Glu Leu Leu Leu Ala<br>                        480                            485                            490 | 1492 |
| cgg aag atc agt gtc aac gcc aag gat gag gac cag tgg aca gcc ctc<br>Arg Lys Ile Ser Val Asn Ala Lys Asp Glu Asp Gln Trp Thr Ala Leu<br>                      495                            500                            505 | 1540 |
| cac ttt gca gcc cag aac ggg gat gag tct agc aca cgg ctg ctg ttg<br>His Phe Ala Ala Gln Asn Gly Asp Glu Ser Ser Thr Arg Leu Leu Leu<br>510                            515                            520 | 1588 |

-continued

| | |
|---|---|
| gag aag aac gcc tcg gtc aac gag gtg gac ttt gag ggc cgg acg ccc<br>Glu Lys Asn Ala Ser Val Asn Glu Val Asp Phe Glu Gly Arg Thr Pro<br>525                              530                         535                     540 | 1636 |
| atg cac gtg gcc tgc cag cac ggg cag gag aat atc gtg cgc atc ctg<br>Met His Val Ala Cys Gln His Gly Gln Glu Asn Ile Val Arg Ile Leu<br>                        545                         550                         555 | 1684 |
| ctg cgc cga ggc gtg gac gtg agc ctg cag ggc aag gat gcc tgg ctg<br>Leu Arg Arg Gly Val Asp Val Ser Leu Gln Gly Lys Asp Ala Trp Leu<br>                 560                         565                         570 | 1732 |
| cca ctg cac tac gct gcc tgg cag ggc cac ctg ccc atc gtc aag ctg<br>Pro Leu His Tyr Ala Ala Trp Gln Gly His Leu Pro Ile Val Lys Leu<br>             575                         580                         585 | 1780 |
| ctg gcc aag cag ccg ggg gtg agt gtg aac gcc cag acg ctg gat ggg<br>Leu Ala Lys Gln Pro Gly Val Ser Val Asn Ala Gln Thr Leu Asp Gly<br>590                              595                         600 | 1828 |
| agg acg cca ttg cac ctg gcc gca cag cgc ggg cac tac cgc gtg gcc<br>Arg Thr Pro Leu His Leu Ala Ala Gln Arg Gly His Tyr Arg Val Ala<br>605                              610                         615                     620 | 1876 |
| cgc atc ctc atc gac ctg tgc tcc gac gtc aac gtc tgc agc ctg ctg<br>Arg Ile Leu Ile Asp Leu Cys Ser Asp Val Asn Val Cys Ser Leu Leu<br>                        625                         630                         635 | 1924 |
| gca cag aca ccc ctg cac gtg gcc gcg gag acg ggg cac acg agc act<br>Ala Gln Thr Pro Leu His Val Ala Ala Glu Thr Gly His Thr Ser Thr<br>             640                         645                         650 | 1972 |
| gcc agg ctg ctc ctg cat cgg ggc gct ggc aag gag gcc gtg acc tca<br>Ala Arg Leu Leu Leu His Arg Gly Ala Gly Lys Glu Ala Val Thr Ser<br>                 655                         660                         665 | 2020 |
| gac ggc tac acc gct ctg cac ctg gct gcc cgc aac gga cac ctg gcc<br>Asp Gly Tyr Thr Ala Leu His Leu Ala Ala Arg Asn Gly His Leu Ala<br>         670                         675                         680 | 2068 |
| act gtc aag ctg ctt gtc gag gag aag gcc gat gtg ctg gcc cgg gga<br>Thr Val Lys Leu Leu Val Glu Glu Lys Ala Asp Val Leu Ala Arg Gly<br>685                              690                         695                     700 | 2116 |
| ccc ctg aac cag acg gcg ctg cac ctg gct gcc gcc cac ggg cac tcg<br>Pro Leu Asn Gln Thr Ala Leu His Leu Ala Ala Ala His Gly His Ser<br>                        705                         710                         715 | 2164 |
| gag gtg gtg gag gag ttg gtc agc gcc gat gtc att gac ctg ttc gac<br>Glu Val Val Glu Glu Leu Val Ser Ala Asp Val Ile Asp Leu Phe Asp<br>             720                         725                         730 | 2212 |
| gag cag ggg ctc agc gcg ctg cac ctg gcc gcc cag ggc cgg cac gca<br>Glu Gln Gly Leu Ser Ala Leu His Leu Ala Ala Gln Gly Arg His Ala<br>                 735                         740                         745 | 2260 |
| cag acg gtg gag act ctg ctc agg cat ggg gcc cac atc aac ctg cag<br>Gln Thr Val Glu Thr Leu Leu Arg His Gly Ala His Ile Asn Leu Gln<br>         750                         755                         760 | 2308 |
| agc ctc aag ttc cag ggc ggc cat ggc ccc gcc gcc aca ctc ctg cgg<br>Ser Leu Lys Phe Gln Gly Gly His Gly Pro Ala Ala Thr Leu Leu Arg<br>765                              770                         775                     780 | 2356 |
| cga agc aag acc tag ctggctgcct gcggagaccg ggggtccacg tggggctctt<br>Arg Ser Lys Thr  * | 2411 |
| gtcctgtcct gtgttcctcg tggggatgga acgatcctgc gtggggcccc gttgtggctt | 2471 |
| acctaaatgt taaccaagca gaggtgacat ggtgccatca ggaggcggct gctgctgacc | 2531 |
| ggagtgtccc ctccaggtga agctggctca ggtgcacatg cccgctccat catcgatcta | 2591 |
| ggcacctgct gtctgaaggg accgtgggtc agaatcattt cgttgtgctc ctaatgggtc | 2651 |
| gctgaggctg gtctctcagt gatgaagccc caggcgtgga agcatccact ctctcctgag | 2711 |
| gcgagccacc ttgggttgct ggagctcacc agtcttgagg gaggtgcagg ggaaactgtg | 2771 |

-continued

```
tttttatct tcatacatga cggtgggcag agaggcctgt cttaaagttt ccatggaatt     2831
gttttataaa atatcttaag agatgaatac cttatcagct gttgcttgaa acctgttaaa     2891
aatgttcata acattggata gtctagtctc taaatgatgg ctaagtagtg gggttggctt     2951
tgaaaacaat gttttatgca acaaggaacg aatggtagca gccagctttg cggggcgtat     3011
gtgtggccag ctcttaacca ttccagtcta ttacttgggt gagtccttgt ggacaaccac     3071
acacacgtgc ccacatggta ctagctgccg ttcgtttctc gttgcctaag atgttttggc     3131
aactctagag ccacaggcct aagagtcatt aaaaaattct ccctttgtaa cctcagtgct     3191
ggggactgag gcgagccccc tcaggtcgct ggagtgcacc agtcttgggg aagaggtgca     3251
ggagaagctg tgtttttat ctccacacgc agtatgaaga taaaattaca tagtattacc      3311
tagacataga cagtattacc taggtagatg cactgctcac ctgcacccctt cccagctctc    3371 attttttgtta ggtgatttgg gatagggata gtgttttggg gtatgggggg agtgtttctg    3431
acctgctttg cagacgtgcc tccgcacctc agcagtttgg ggtgtggccc cagggcggtt    3491
cttggatgta aaagatgtgg ccatctagcc tcgtaacttc actgtcacct gtgtcccata    3551
gggtgccttc tgaatactgt tattagaata agtttgttgc agaacgtgac cctgcgtgca    3611
aacatgtacc gtggcctggt atatgataga gattgatatt aatgtaccat gtatgttaat    3671
gtgaatctgt gggcaggata cttttccatg gcaggaaata tccaagctgt tgaaactggc    3731
tatgttttaa tatgcctcat tgtgccttta ctgttgtgtg gactgcgtga gggacaagaa    3791
gttccatttg atgtcaataa agcaaagtac ttgcctactt ttttgaanct gaaaaaaaaa    3851
aaaaaaagg                                                             3860
```

<210> SEQ ID NO 2
<211> LENGTH: 784
<212> TYPE: PRT
<213> ORGANISM: H. sapiens

<400> SEQUENCE: 2

```
Met Glu Gly Asp Gly Gly Thr Pro Trp Ala Leu Ala Leu Leu Arg Thr
  1               5                  10                  15

Phe Asp Ala Gly Glu Phe Thr Gly Trp Glu Lys Val Gly Ser Gly Gly
                 20                  25                  30

Phe Gly Gln Val Tyr Lys Val Arg His Val His Trp Lys Thr Trp Leu
             35                  40                  45

Ala Ile Lys Cys Ser Pro Ser Leu His Val Asp Asp Arg Glu Arg Met
         50                  55                  60

Glu Leu Leu Glu Glu Ala Lys Lys Met Glu Met Ala Lys Phe Arg Tyr
 65                  70                  75                  80

Ile Leu Pro Val Tyr Gly Ile Cys Arg Glu Pro Val Gly Leu Val Met
                     85                  90                  95

Glu Tyr Met Glu Thr Gly Ser Leu Glu Lys Leu Leu Ala Ser Glu Pro
                100                 105                 110

Leu Pro Trp Asp Leu Arg Phe Arg Ile Ile His Glu Thr Ala Val Gly
            115                 120                 125

Met Asn Phe Leu His Cys Met Ala Pro Pro Leu Leu His Leu Asp Leu
        130                 135                 140

Lys Pro Ala Asn Ile Leu Leu Asp Ala His Tyr His Val Lys Ile Ser
145                 150                 155                 160

Asp Phe Gly Leu Ala Lys Cys Asn Gly Leu Ser His Ser His Asp Leu
                    165                 170                 175
```

-continued

```
Ser Met Asp Gly Leu Phe Gly Thr Ile Ala Tyr Leu Pro Pro Glu Arg
            180                 185                 190

Ile Arg Glu Lys Ser Arg Leu Phe Asp Thr Lys His Asp Val Tyr Ser
        195                 200                 205

Phe Ala Ile Val Ile Trp Gly Val Leu Thr Gln Lys Lys Pro Phe Ala
    210                 215                 220

Asp Glu Lys Asn Ile Leu His Ile Met Val Lys Val Lys Gly His
225                 230                 235                 240

Arg Pro Glu Leu Pro Pro Val Cys Arg Ala Arg Pro Arg Ala Cys Ser
                245                 250                 255

His Leu Ile Arg Leu Met Gln Arg Cys Trp Gln Gly Asp Pro Arg Val
            260                 265                 270

Arg Pro Thr Phe Gln Glu Ile Thr Ser Glu Thr Glu Asp Leu Cys Glu
        275                 280                 285

Lys Pro Asp Asp Glu Val Lys Glu Thr Ala His Asp Leu Asp Val Lys
    290                 295                 300

Ser Pro Pro Glu Pro Arg Ser Glu Val Val Pro Ala Arg Leu Lys Arg
305                 310                 315                 320

Ala Ser Ala Pro Thr Phe Asp Asn Asp Tyr Ser Leu Ser Glu Leu Leu
                325                 330                 335

Ser Gln Leu Asp Ser Gly Val Ser Gln Ala Val Glu Gly Pro Glu Glu
            340                 345                 350

Leu Ser Arg Ser Ser Ser Glu Ser Lys Leu Pro Ser Ser Gly Ser Gly
        355                 360                 365

Lys Arg Leu Ser Gly Val Ser Ser Val Asp Ser Ala Phe Ser Ser Arg
    370                 375                 380

Gly Ser Leu Ser Leu Ser Phe Glu Arg Glu Pro Ser Thr Ser Asp Leu
385                 390                 395                 400

Gly Thr Thr Arg Arg Pro Glu Glu Ala Cys Gly Cys His Arg Val
                405                 410                 415

Arg Asp Thr Ser Lys Leu Met Lys Ile Leu Gln Pro Gln Asp Val Asp
            420                 425                 430

Leu Ala Leu Asp Ser Gly Ala Ser Leu Leu His Leu Ala Val Glu Ala
        435                 440                 445

Gly Gln Glu Glu Cys Ala Lys Trp Leu Leu Leu Asn Asn Ala Asn Pro
    450                 455                 460

Asn Leu Ser Asn Arg Arg Gly Ser Thr Pro Leu His Met Ala Val Glu
465                 470                 475                 480

Arg Arg Val Arg Gly Val Val Glu Leu Leu Leu Ala Arg Lys Ile Ser
                485                 490                 495

Val Asn Ala Lys Asp Glu Asp Gln Trp Thr Ala Leu His Phe Ala Ala
            500                 505                 510

Gln Asn Gly Asp Glu Ser Ser Thr Arg Leu Leu Leu Glu Lys Asn Ala
        515                 520                 525

Ser Val Asn Glu Val Asp Phe Glu Gly Arg Thr Pro Met His Val Ala
    530                 535                 540

Cys Gln His Gly Gln Glu Asn Ile Val Arg Ile Leu Leu Arg Arg Gly
545                 550                 555                 560

Val Asp Val Ser Leu Gln Gly Lys Asp Ala Trp Leu Pro Leu His Tyr
                565                 570                 575

Ala Ala Trp Gln Gly His Leu Pro Ile Val Lys Leu Leu Ala Lys Gln
            580                 585                 590
```

-continued

```
Pro Gly Val Ser Val Asn Ala Gln Thr Leu Asp Gly Arg Thr Pro Leu
            595                 600                 605
His Leu Ala Ala Gln Arg Gly His Tyr Arg Val Ala Arg Ile Leu Ile
        610                 615                 620
Asp Leu Cys Ser Asp Val Asn Val Cys Ser Leu Ala Gln Thr Pro
625                 630                 635                 640
Leu His Val Ala Ala Glu Thr Gly His Thr Ser Thr Ala Arg Leu Leu
                645                 650                 655
Leu His Arg Gly Ala Gly Lys Glu Ala Val Thr Ser Asp Gly Tyr Thr
            660                 665                 670
Ala Leu His Leu Ala Ala Arg Asn Gly His Leu Ala Thr Val Lys Leu
        675                 680                 685
Leu Val Glu Glu Lys Ala Asp Val Leu Ala Arg Gly Pro Leu Asn Gln
    690                 695                 700
Thr Ala Leu His Leu Ala Ala Ala His Gly His Ser Glu Val Val Glu
705                 710                 715                 720
Glu Leu Val Ser Ala Asp Val Ile Asp Leu Phe Asp Glu Gln Gly Leu
                725                 730                 735
Ser Ala Leu His Leu Ala Ala Gln Gly Arg His Ala Gln Thr Val Glu
            740                 745                 750
Thr Leu Leu Arg His Gly Ala His Ile Asn Leu Gln Ser Leu Lys Phe
        755                 760                 765
Gln Gly Gly His Gly Pro Ala Ala Thr Leu Leu Arg Arg Ser Lys Thr
    770                 775                 780
```

<210> SEQ ID NO 3
<211> LENGTH: 2355
<212> TYPE: DNA
<213> ORGANISM: H. sapiens

<400> SEQUENCE: 3

```
atggagggcg acggcgggac cccatgggcc ctggcgctgc tgcgcacctt cgacgcgggc      60
gagttcacgg gctgggagaa ggtgggctcg gcggcttcg ggcaggtgta caaggtgcgc     120
catgtccact ggaagacctg gctggccatc aagtgctcgc ccagcctgca cgtcgacgac     180
agggagcgca tggagctttt ggaagaagcc aagaagatgg agatggccaa gtttcgctac     240
atcctgcctg tgtatggcat ctgccgcgaa cctgtcggcc tggtcatgga gtacatggag     300
acgggctccc tggaaaagct gctggcttcg gagccattgc catgggatct ccggttccga     360
atcatccacg agacggcggt gggcatgaac ttcctgcact gcatggcccc gccactcctg     420
cacctggacc tcaagcccgc gaacatcctg ctggatgccc actaccacgt caagatttct     480
gattttggtc tggccaagtg caacgggctg tcccactcgc atgacctcag catggatggc     540
ctgtttggca caatcgccta cctccctcca gagcgcatca gggagaagag ccggctcttc     600
gacaccaagc acgatgtata cagctttgcg atcgtcatct ggggcgtgct cacacagaag     660
aagccgtttg cagatgagaa gaacatcctg cacatcatgg tgaaggtggt gaagggccac     720
cgccccgagc tgccgcccgt gtgcagagcc ggccgcgcg cctgcagcca cctgatacgc     780
ctcatgcagc ggtgctggca gggggatccg cgagttaggc ccaccttcca agaaattact     840
tctgaaaccg aggacctgtg tgaaaagcct gatgacgaag tgaaagaaac tgctcatgat     900
ctggacgtga aaagcccccc ggagcccagg agcgaggtgg tgcctgcgag gctcaagcgg     960
gcctctgccc ccaccttcga taacgactac agcctctccg agcttctctc acagctggac    1020
tctggagttt cccaggctgt cgagggcccc gaggagctca gccgcagctc ctctgagtcc    1080
```

```
aagctgccat cgtccggcag tgggaagagg ctctcggggg tgtcctcggt ggactccgcc   1140
ttctcttcca gaggatcact gtcgctgtcc tttgagcggg aaccttcaac cagcgatctg   1200
ggtaccacaa gacgtccaga agaagaagct tgtggatgcc atcgtgtccg gacaccagc    1260 aaactgatga agatcctgca gccgcaggac gtggacctgg cactggacag cggtgccagc   1320
ctgctgcacc tggcggtgga ggccgggcaa gaggagtgcg ccaagtggct gctgctcaac   1380
aatgccaacc ccaacctgag caaccgtagg ggctccaccc cgttgcacat ggccgtggag   1440
aggagggtgc ggggtgtcgt ggagctcctg ctggcacgga agatcagtgt caacgccaag   1500
gatgaggacc agtggacagc cctccacttt gcagcccaga acggggatga gtctagcaca   1560
cggctgctgt tggagaagaa cgcctcggtc aacgaggtgg actttgaggg ccggacgccc   1620
atgcacgtgg cctgccagca cgggcaggag aatatcgtgc gcatcctgct cgccgaggc    1680 gtggacgtga gcctgcaggg caaggatgcc tggctgccac tgcactacgc tgcctggcag   1740
ggccacctgc ccatcgtcaa gctgctggcc aagcagccgg gggtgagtgt gaacgcccag   1800
acgctggatg ggaggacgcc attgcacctg gccgcacagc gcgggcacta ccgcgtggcc   1860
cgcatcctca tcgacctgtg ctccgacgtc aacgtctgca gcctgctggc acagacaccc   1920
ctgcacgtgg ccgcggagac ggggcacacg agcactgcca ggctgctcct gcatcggggc   1980
gctggcaagg aggccgtgac ctcagacggc tacaccgctc tgcacctggc tgcccgcaac   2040
ggacacctgg ccactgtcaa gctgcttgtc gaggagaagg ccgatgtgct ggcccgggga   2100
cccctgaacc agacggcgct gcacctggct gccgcccacg gcactcgga gtggtggag     2160 gagttggtca gcgccgatgt cattgacctg ttcgacgagc aggggctcag cgcgctgcac   2220
ctggccgccc agggccggca cgcacagacg gtggagactc tgctcaggca tggggcccac   2280
atcaacctgc agagcctcaa gttccagggc ggccatggcc ccgccgccac actcctgcgg   2340
cgaagcaaga cctag                                                   2355
```

<210> SEQ ID NO 4
<211> LENGTH: 272
<212> TYPE: PRT
<213> ORGANISM: Artificial Sequence
<220> FEATURE:
<223> OTHER INFORMATION: Consensus Protein Kinase Domain

<400> SEQUENCE: 4

```
Tyr Glu Leu Leu Glu Lys Leu Gly Glu Gly Ser Phe Gly Lys Val Tyr
 1               5                  10                  15

Lys Ala Lys His Lys Thr Gly Lys Ile Val Ala Val Lys Ile Leu Lys
                20                  25                  30

Lys Glu Ser Leu Ser Leu Arg Glu Ile Gln Ile Leu Lys Arg Leu Ser
            35                  40                  45

His Pro Asn Ile Val Arg Leu Leu Gly Val Phe Glu Asp Thr Asp Asp
        50                  55                  60

His Leu Tyr Leu Val Met Glu Tyr Met Glu Gly Gly Asp Leu Phe Asp
 65                  70                  75                  80

Tyr Leu Arg Arg Asn Gly Pro Leu Ser Glu Lys Glu Ala Lys Lys Ile
                85                  90                  95

Ala Leu Gln Ile Leu Arg Gly Leu Glu Tyr Leu His Ser Asn Gly Ile
           100                 105                 110

Val His Arg Asp Leu Lys Pro Glu Asn Ile Leu Leu Asp Glu Asn Gly
       115                 120                 125
```

```
Thr Val Lys Ile Ala Asp Phe Gly Leu Ala Arg Leu Leu Glu Lys Leu
        130                 135                 140

Thr Thr Phe Val Gly Thr Pro Trp Tyr Met Met Ala Pro Glu Val Ile
145                 150                 155                 160

Leu Glu Gly Arg Gly Tyr Ser Ser Lys Val Asp Val Trp Ser Leu Gly
                165                 170                 175

Val Ile Leu Tyr Glu Leu Leu Thr Gly Gly Pro Leu Phe Pro Gly Ala
                180                 185                 190

Asp Leu Pro Ala Phe Thr Gly Gly Asp Glu Val Asp Gln Leu Ile Ile
            195                 200                 205

Phe Val Leu Lys Leu Pro Phe Ser Asp Glu Leu Pro Lys Thr Arg Ile
        210                 215                 220

Asp Pro Leu Glu Glu Leu Phe Arg Ile Lys Lys Arg Leu Pro Leu
225                 230                 235                 240

Pro Ser Asn Cys Ser Glu Glu Leu Lys Asp Leu Leu Lys Lys Cys Leu
                245                 250                 255

Asn Lys Asp Pro Ser Lys Arg Pro Gly Ser Ala Thr Ala Lys Glu Ile
                260                 265                 270
```

<210> SEQ ID NO 5
<211> LENGTH: 34
<212> TYPE: PRT
<213> ORGANISM: Artificial Sequence
<220> FEATURE:
<223> OTHER INFORMATION: consensus sequence for ATP binding
<220> FEATURE:
<221> NAME/KEY: VARIANT
<222> LOCATION: 1
<223> OTHER INFORMATION: The Xaa at position 1 can be Leu, Ile or Val.
<220> FEATURE:
<221> NAME/KEY: VARIANT
<222> LOCATION: 3, 5
<223> OTHER INFORMATION: The Xaa at positions 3 and 5 can be any amino
      acid residue except Pro.
<220> FEATURE:
<221> NAME/KEY: VARIANT
<222> LOCATION: 6
<223> OTHER INFORMATION: The Xaa at position 6 can be Phe, Tyr, Trp,
      Met, Gly, Ser, Thr, Asn, or His.
<220> FEATURE:
<221> NAME/KEY: VARIANT
<222> LOCATION: 7
<223> OTHER INFORMATION: The Xaa at position 7 can be Ser, Gly or Ala.
<220> FEATURE:
<221> NAME/KEY: VARIANT
<222> LOCATION: 8
<223> OTHER INFORMATION: The Xaa at position 8 can be any amino acid
      except Pro or Trp.
<220> FEATURE:
<221> NAME/KEY: VARIANT
<222> LOCATION: 9
<223> OTHER INFORMATION: The Xaa at position 9 can be Leu, Ile, Val,
      Cys, Ala or Thr.
<220> FEATURE:
<221> NAME/KEY: VARIANT
<222> LOCATION: 10
<223> OTHER INFORMATION: The Xaa at position 10 can be any amino acid
      except Pro or Asp.
<220> FEATURE:
<221> NAME/KEY: VARIANT
<222> LOCATION: 11
<223> OTHER INFORMATION: The Xaa at position 11 can be any amino acid.
<220> FEATURE:
<221> NAME/KEY: VARIANT
<222> LOCATION: 12
<223> OTHER INFORMATION: The Xaa at position 12 can be Gly, Ser, Thr,
      Ala, Cys, Leu, Ile, Val, Met, Phe or Tyr.
<220> FEATURE:
<221> NAME/KEY: VARIANT
<222> LOCATION: (13)...(30)

```
<223> OTHER INFORMATION: The Xaa at positions 13 to 30 can be any amino
      acid.
<220> FEATURE:
<221> NAME/KEY: VARIANT
<222> LOCATION: (13)...(30)
<223> OTHER INFORMATION: The number of Xaa residues in this portion of
      the consensus can vary between 5 residues and 18 residues.
<220> FEATURE:
<221> NAME/KEY: VARIANT
<222> LOCATION: 31
<223> OTHER INFORMATION: The Xaa at position 31 can be Leu, Ile, Val,
      Met, Phe, Tyr, Trp, Cys, Ser, Thr, Ala, or Arg.
<220> FEATURE:
<221> NAME/KEY: VARIANT
<222> LOCATION: 32
<223> OTHER INFORMATION: The Xaa at position 32 can be Ala, Ile, Val or
      Pro.
<220> FEATURE:
<221> NAME/KEY: VARIANT
<222> LOCATION: 33
<223> OTHER INFORMATION: The Xaa at position 33 can be Leu, Ile, Val,
      Met, Phe, Ala, Gly, Cys, Lys, or Arg.

<400> SEQUENCE: 5

Xaa Gly Xaa Gly Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa
            20                  25                  30

Xaa Lys

<210> SEQ ID NO 6
<211> LENGTH: 13
<212> TYPE: PRT
<213> ORGANISM: Artificial Sequence
<220> FEATURE:
<223> OTHER INFORMATION: consensus sequence for serine/threonine kinase
      active site
<220> FEATURE:
<221> NAME/KEY: VARIANT
<222> LOCATION: 1
<223> OTHER INFORMATION: The Xaa at position 1 can be Leu, Ile, Val,
      Met,
      Phe, Tyr or Cys.
<220> FEATURE:
<221> NAME/KEY: VARIANT
<222> LOCATION: 2,4,8,9
<223> OTHER INFORMATION: The Xaa at positions 2, 4, 8 or 9 can be any
      amino
      acid residue.
<220> FEATURE:
<221> NAME/KEY: VARIANT
<222> LOCATION: 3
<223> OTHER INFORMATION: The amino acid residue at position 3 can be
      His or
      Tyr.
<220> FEATURE:
<221> NAME/KEY: VARIANT
<222> LOCATION: 6
<223> OTHER INFORMATION: The amino acid residue at position 6 can be
      Leu,
      Ile, Val, Met, Phe or Tyr.
<220> FEATURE:
<221> NAME/KEY: VARIANT
<222> LOCATION: 11,12,13
<223> OTHER INFORMATION: The Xaa at positions 11, 12, or 13 can be Leu,
      Ile, Val, Met, Phe, Tyr, Cys or Thr.

<400> SEQUENCE: 6

Xaa Xaa Xaa Xaa Asp Xaa Lys Xaa Xaa Asn Xaa Xaa Xaa
 1               5                   10

<210> SEQ ID NO 7
<211> LENGTH: 12
```

```
<212> TYPE: PRT
<213> ORGANISM: Artificial Sequence
<220> FEATURE:
<223> OTHER INFORMATION: consensus sequence for aspartyl protease active
      site
<220> FEATURE:
<221> NAME/KEY: VARIANT
<222> LOCATION: 1
<223> OTHER INFORMATION: The Xaa at position 1 can be Leu, Ile, Val,
      Met,
      Phe, Gly, Ala or Cys.
<220> FEATURE:
<221> NAME/KEY: VARIANT
<222> LOCATION: 2
<223> OTHER INFORMATION: The Xaa at position 2 can be Leu, Ile, Val,
      Met,
      Thr, Ala, Asp or Asn.
<220> FEATURE:
<221> NAME/KEY: VARIANT
<222> LOCATION: 3
<223> OTHER INFORMATION: The Xaa at position 3 can be Leu, Ile, Val,
      Phe,
      Ser or Ala.
<220> FEATURE:
<221> NAME/KEY: VARIANT
<222> LOCATION: 5
<223> OTHER INFORMATION: The Xaa at position 5 can be Ser or Thr.
<220> FEATURE:
<221> NAME/KEY: VARIANT
<222> LOCATION: 7
<223> OTHER INFORMATION: The Xaa at position 7 can be Ser, Thr, Ala or
      Val.
<220> FEATURE:
<221> NAME/KEY: VARIANT
<222> LOCATION: 8
<223> OTHER INFORMATION: The Xaa at position 8 can be Ser, Thr, Ala,
      Pro,
      Asp, Glu, Asn, or Gln.
<220> FEATURE:
<221> NAME/KEY: VARIANT
<222> LOCATION: 9, 11
<223> OTHER INFORMATION: The Xaa at positions 9 and 11 can be any amino
      acid residue.
<220> FEATURE:
<221> NAME/KEY: VARIANT
<222> LOCATION: 10
<223> OTHER INFORMATION: The Xaa at position 10 can be Leu, Ile, Val,
      Met,
      Phe, Ser Thr, Asn, or Cys.
<220> FEATURE:
<221> NAME/KEY: VARIANT
<222> LOCATION: 12
<223> OTHER INFORMATION: The Xaa at position 12 can be Leu, Ile, Val,
      Met,
      Phe, Gly, Thr or Ala.

<400> SEQUENCE: 7

Xaa Xaa Xaa Asp Xaa Gly Xaa Xaa Xaa Xaa Xaa Xaa
 1               5                  10

<210> SEQ ID NO 8
<211> LENGTH: 33
<212> TYPE: PRT
<213> ORGANISM: Artificial Sequence
<220> FEATURE:
<223> OTHER INFORMATION: consensus sequence for ankyrin domain

<400> SEQUENCE: 8

Asp Gly Arg Thr Pro Leu His Leu Ala Ala Arg Asn Gly His Leu Glu
 1               5                  10                  15

Val Val Lys Leu Leu Leu Glu Ala Gly Ala Asp Val Asn Ala Arg Asp
                20                  25                  30

Lys
```

```
<210> SEQ ID NO 9
<211> LENGTH: 20
<212> TYPE: DNA
<213> ORGANISM: Artificial Sequence
<220> FEATURE:
<223> OTHER INFORMATION: forward primer

<400> SEQUENCE: 9
ggcacggaag atcagtgtca                                              20

<210> SEQ ID NO 10
<211> LENGTH: 20
<212> TYPE: DNA
<213> ORGANISM: Artificial Sequence
<220> FEATURE:
<223> OTHER INFORMATION: reverse primer

<400> SEQUENCE: 10
cgaggcgttc ttctccaaca                                              20

<210> SEQ ID NO 11
<211> LENGTH: 26
<212> TYPE: DNA
<213> ORGANISM: Artificial Sequence
<220> FEATURE:
<223> OTHER INFORMATION: probe

<400> SEQUENCE: 11
agggctgtcc actggtcctc atcctt                                       26

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
gatgtggttg aattcatgga gggcgacggc gggacc                            36

<210> SEQ ID NO 13
<211> LENGTH: 39
<212> TYPE: DNA
<213> ORGANISM: Artificial Sequence
<220> FEATURE:
<223> OTHER INFORMATION: primer

<400> SEQUENCE: 13
gatgctggct ctagaggtct tgcttcgccg caggagtgt                         39

<210> SEQ ID NO 14
<211> LENGTH: 21
<212> TYPE: DNA
<213> ORGANISM: Artificial Sequence
<220> FEATURE:
<223> OTHER INFORMATION: forward primer

<400> SEQUENCE: 14
tccgagttgc tgtcacagtt g                                            21

<210> SEQ ID NO 15
<211> LENGTH: 19
<212> TYPE: DNA
<213> ORGANISM: Artificial Sequence
<220> FEATURE:
<223> OTHER INFORMATION: reverse primer
```

```
<400> SEQUENCE: 15
cgatgggagc ttgcattca                                                    19

<210> SEQ ID NO 16
<211> LENGTH: 23
<212> TYPE: DNA
<213> ORGANISM: Artificial Sequence
<220> FEATURE:
<223> OTHER INFORMATION: probe

<400> SEQUENCE: 16
tcccagactc ttgaaggccc cga                                               23

<210> SEQ ID NO 17
<211> LENGTH: 21
<212> TYPE: PRT
<213> ORGANISM: Artificial Sequence
<220> FEATURE:
<223> OTHER INFORMATION: synthetic peptide

<400> SEQUENCE: 17

Gln Ser Leu Lys Phe Gln Gly Gly His Gly Pro Ala Ala Thr Leu Leu
 1               5                  10                  15

Arg Arg Ser Lys Thr
            20

<210> SEQ ID NO 18
<211> LENGTH: 20
<212> TYPE: PRT
<213> ORGANISM: Artificial Sequence
<220> FEATURE:
<223> OTHER INFORMATION: synthetic peptide

<400> SEQUENCE: 18

Gly Pro Glu Glu Leu Ser Arg Ser Ser Glu Ser Lys Leu Pro Ser
 1               5                  10                  15

Ser Gly Ser Gly
            20

<210> SEQ ID NO 19
<211> LENGTH: 20
<212> TYPE: PRT
<213> ORGANISM: Artificial Sequence
<220> FEATURE:
<223> OTHER INFORMATION: synthetic peptide

<400> SEQUENCE: 19

Ser Glu Thr Glu Asp Leu Cys Glu Lys Pro Asp Asp Glu Val Lys Glu
 1               5                  10                  15

Thr Ala His Asp
            20

<210> SEQ ID NO 20
<211> LENGTH: 18
<212> TYPE: PRT
<213> ORGANISM: Artificial Sequence
<220> FEATURE:
<223> OTHER INFORMATION: synthetic peptide
<220> FEATURE:
<221> NAME/KEY: SITE
<222> LOCATION: 1
<223> OTHER INFORMATION: A biotin is covalently attached to the residue
      at
      position 1.
```

-continued

```
<400> SEQUENCE: 20

Lys Lys Arg Phe Ser Phe Lys Lys Ser Phe Lys Leu Ser Gly Phe Ser
 1               5                  10                  15

Phe Lys

<210> SEQ ID NO 21
<211> LENGTH: 21
<212> TYPE: DNA
<213> ORGANISM: Artificial Sequence
<220> FEATURE:
<223> OTHER INFORMATION: siRNA target sequence

<400> SEQUENCE: 21
aagaacatcc tgcacatcat g                                          21

<210> SEQ ID NO 22
<211> LENGTH: 21
<212> TYPE: DNA
<213> ORGANISM: Artificial Sequence
<220> FEATURE:
<223> OTHER INFORMATION: siRNA target sequence

<400> SEQUENCE: 22
aagaagatgg agatggccaa g                                          21

<210> SEQ ID NO 23
<211> LENGTH: 21
<212> TYPE: DNA
<213> ORGANISM: Artificial Sequence
<220> FEATURE:
<223> OTHER INFORMATION: siRNA target sequence

<400> SEQUENCE: 23
aaccttcaac cagcgatctg g                                          21

<210> SEQ ID NO 24
<211> LENGTH: 23
<212> TYPE: DNA
<213> ORGANISM: Artificial Sequence
<220> FEATURE:
<223> OTHER INFORMATION: siRNA sense strand, nucleotides 1-21 are
      ribonucleic acid, nucleotides 22 and 23 are
      deoxyribonucleic acid.

<400> SEQUENCE: 24
aagaacaucc ugcacaucau gtt                                        23

<210> SEQ ID NO 25
<211> LENGTH: 23
<212> TYPE: DNA
<213> ORGANISM: Artificial Sequence
<220> FEATURE:
<223> OTHER INFORMATION: siRNA anti-sense strand, complement of SEQ ID
      NO:24, nucleotides 1-21 are ribonucleic acid,
      nucleotides 22-23 are deoxyribonucleic acid.

<400> SEQUENCE: 25
caugaugugc aggauguucu utt                                        23

<210> SEQ ID NO 26
<211> LENGTH: 23
<212> TYPE: DNA
<213> ORGANISM: Artificial Sequence
<220> FEATURE:
<223> OTHER INFORMATION: siRNA sense strand, nucleotides 1-21 are
      ribonucleic acid, nucleotides 22 and 23 are
```

-continued

```
            deoxyribonucleic acid.

<400> SEQUENCE: 26
aagaagaugg agauggccaa gtt                                            23

<210> SEQ ID NO 27
<211> LENGTH: 23
<212> TYPE: DNA
<213> ORGANISM: Artificial Sequence
<220> FEATURE:
<223> OTHER INFORMATION: siRNA anti-sense strand, complement of SEQ ID
      NO:26, nucleotides 1-21 are ribonucleic acid,
      nucleotides 22 and 23 are deoxyribonucleic acid.

<400> SEQUENCE: 27
cuuggccauc uccaucuucu utt                                            23

<210> SEQ ID NO 28
<211> LENGTH: 23
<212> TYPE: DNA
<213> ORGANISM: Artificial Sequence
<220> FEATURE:
<223> OTHER INFORMATION: siRNA sense strand, nucleotides 1-21 are
      ribonucleic acid, nucleotides 22 and 23 are
      deoxyribonucleic acid.

<400> SEQUENCE: 28
aaccuucaac cagcgaucug gtt                                            23

<210> SEQ ID NO 29
<211> LENGTH: 23
<212> TYPE: DNA
<213> ORGANISM: Artificial Sequence
<220> FEATURE:
<223> OTHER INFORMATION: siRNA anti-sense strand, complement of SEQ ID
      NO:28, nucleotides 1-21 are ribonucleic acid,
      nucleotides 22 and 23 are deoxyribonucleic acid.

<400> SEQUENCE: 29
ccagaucgcu gguugaaggu utt                                            23
```